US005753502A

United States Patent [19]
Kilgannon et al.

[11] Patent Number: 5,753,502
[45] Date of Patent: May 19, 1998

[54] NEURON-SPECIFIC ICAM-4 PROMOTER

[75] Inventors: Patrick D. Kilgannon, Bothell; W. Michael Gallatin, Mercer Island, both of Wash.

[73] Assignee: ICOS Corporation, Bothell, Wash.

[21] Appl. No.: 656,984

[22] Filed: Jun. 6, 1996

Related U.S. Application Data

[63] Continuation-in-part of Ser. No. 481,130, Jun. 7, 1995, Pat. No. 5,702,917, which is a continuation-in-part of Ser. No. 245,295, May 18, 1994, Pat. No. 5,700,658, which is a continuation-in-part of Ser. No. 102,852, Aug. 5, 1993, abandoned.

[51] Int. Cl.$^6$ ................................................. C12N 14/85
[52] U.S. Cl. .................. 435/320.1; 435/325; 536/24.1
[58] Field of Search ................. 536/24.1; 435/320.1, 435/325, 252.3

[56] References Cited

FOREIGN PATENT DOCUMENTS

| 468257 A | 1/1992 | European Pat. Off. |
| WO 89/02922 | 4/1989 | WIPO |
| WO 90/13300 | 11/1990 | WIPO |
| WO 91/10683 | 7/1991 | WIPO |
| WO 91/16928 | 11/1991 | WIPO |
| WO 92/04034 | 3/1992 | WIPO |
| WO 92/06199 | 4/1992 | WIPO |
| WO 93/14776 | 8/1993 | WIPO |

OTHER PUBLICATIONS

Bailly et al. Eur. J. Immunol. 25, 3316–3320, 1995.
Sambrook et al. Molecular Cloning : A Laboratory Manual, Second Ed. New York :Cold Spring Harbor Press, p. 2.43, 1989.
Stratagene Cloning Systems Catalog, p. 296, 1994.
Ashkenazi et al., "Protection against endotoxic shock by tumor necrosis factor receptor immunoadhesin," *Proc.Nat-l.Acad.Sci.* (USA) 88:10535–10539 (1991).
Capecchi, "Altering the genome by homologous recombination," *Science* 244:1288–1292 (1989).
Capon et al., "Designing CD4 immunoadhesins for AIDS therapy," *Nature* 337:525–531 (1989).
Chomesynski and Sacchi, "Single–Step Method of RNA Isolation by Acid Guanidinium Thiocyanate–Phenol–Chloroform Extraction," *Anal.Biochem.* 162:156–159 (1987).
de Fourgerolles et al., "Intercellular adhesion molecule 3, a third adhesion counter–receptor for lymphocyte function associated molecule 1 on resting lymphocytes," *J.Exp.Med.* 175:185–190 (1992).
Dustin et al., "Induction by IL–1 and interferon–γ:tissue distribution, biochemistry, and function of a natural adherence molecule (ICAM–1)," *J.Immunol.* 137:245–254 (1986).
Edwards, "Cell adhesion molecules as a target for therapy," *Curr.Opin.Ther.Pat.* 1:1617–1630 (1991).
Frohman, *PCR Protocols*, "RACE: rapid amplification of cDNA ends," *Innis* (ed), Acedemic Press: New York, pp. 28–38 (1990).

Imamura et al., "Variations by layers and developmental changes in expression of telencephalin in the visual cortex of cats," *Neurosci.Letts.* 119:118–121 (1990).
Kita et al., "Sequence and expression of ratICAM–1," *Biochem.Biophys.Acta.* 1131;108–110 (1992).
Lothman et al., "Kindling with Rapidly Recurring Hippocampal Seizures," *Brain.Res.* 360:83–91 (1985).
Mori et al., "Telencephalon-specific antigen identified by monoclonal antibody," *Proc.Natl.Acad.Sci.* (USA) 84:3921–3925 (1987).
Newman et al., "PECAM-1 (CD31) cloning and relation to adhesion molecules of the immunoglobulin gene superfamily," *Science* 247:1219–1222 (1990).
Oka et al., "Mammalian telencephalic neurons express a segment–specific membrane glycoprotein, telencephalin," *Neuroscience* 35:93–103 (1990).
Sonderegger et al., "Regulation of axonal growth in the vertebrate nervous system by interactions between glycoproteins belonging to two subgroups of the immunoglobulin superfamily," *J. Cell Biol.* 119:1387–1394 (1992).
Springer, "Adhesion receptors of the immune system," *Nature* 346:425–434 (1990).
Staunton et al., "Functional cloning of ICAM-2, a cell adhesion ligand for LFA-1 homologous to ICAM-1," *Nature* 339:61–64 (1989).
Vonderheide et al., "Residues within a conserved amino acid motif of domains 1 and 4 of VCAM-1 are required fir binding to VLA-4," *J.Cell.Biol* 125:215–222 (1994).
Xu et al., "Isolation, characterization, and expression of mouse ICAM-2 complementary and genomic DNA," *J.Immunol.* 149:2650–2655 (1992).
Yoshihara et al., "Immunoglobulin superfamily molecules in the nervous system," *Neurosci.Res.* 10:83–105 (1991).
Yoshihiro et al., "An ICAM–related neuronal glycoprotein, telecephalin, with brain segment-specific expression," *Neuron* 12:541–554 (1994).
Yoshihiro et al., "Primary structure of telencephalon–specific neuronal adhesion molecule telencephalin," *Neuroscience* Supp 18, p. S83 (1994).
Yoshihiro et al., "Telencephanlin, a brain segment–specific dendritic glycoprotein, is a novel member of immunoglobulin superfamily," *Soc.Neurosci.Abstr.* 19 p. 646 (1993).

*Primary Examiner*—John Ulm
*Assistant Examiner*—Karen E. Brown
*Attorney, Agent, or Firm*—Marshall, O'Toole, Gerstein, Murray & Borun

[57] ABSTRACT

DNA sequences, derived from the 5' region of the human neuron-specific cellular adhesion molecule ICAM-4, which promote neuron-specific gene transcription are disclosed along with polynucleotides comprising the promoter DNA operatively linked to heterologous gene-encoding polynucleotides, expression vectors comprising the promoter DNA, and host cells transformed or transfected with DNA comprising the promoter sequences.

9 Claims, No Drawings

NEURON-SPECIFIC ICAM-4 PROMOTER

This application is a continuation-in-part of U.S. patent application Ser. No. 08/481,130, filed Jun. 7, 1995, now U.S. Pat. No. 5,702,917, which is a continuation-in-part of U.S. patent application Ser. No. 08/245,295, filed May 18, 1994, now U.S. Pat. No. 5,700,658 which in turn is a continuation-in-part of U.S. patent application Ser. No. 08/102,852, filed Aug. 5, 1993 now abn.

FIELD OF THE INVENTION

The present invention relates generally to cellular adhesion molecules and more particularly to the cloning and expression of DNA encoding a heretofore unknown polypeptide designated "ICAM-4" which possesses structural relatedness to the intercellular adhesion molecules ICAM-1, ICAM-2, and ICAM-R.

BACKGROUND OF THE INVENTION

Research spanning the last decade has significantly elucidated the molecular events attending cell-cell interactions in the body, especially those events involved in the movement and activation of cells in the immune system, and more recently, those involved in development and normal physiological function of cells in the nervous system. See generally, Springer, *Nature*, 346: 425–434 (1990) regarding cells of the immune system, and Yoshihara, et al. *Neurosci.Res.* 10:83–105 (1991) and Sonderegger and Rathjen, *J.Cell Biol.* 119:1387–1394 (1992) regarding cells of the nervous system. Cell surface proteins, and especially the so-called Cellular Adhesion Molecules ("CAMs") have correspondingly been the subject of pharmaceutical research and development having as its goal intervention in the processes of leukocyte extravasation to sites of inflammation and leukocyte movement to distinct target tissues, as well as neuronal differentiation and formation of complex neuronal circuitry. The isolation and characterization of cellular adhesion molecules, the cloning and expression of DNA sequences encoding such molecules, and the development of therapeutic and diagnostic agents relevant to inflammatory processes and development and function of the nervous system have also been the subject of numerous U.S. and foreign applications for Letters Patent. See Edwards, *Current Opinion in Therapeutic Patents*, 1(11): 1617–1630 (1991) and particularly the published "patent literature references" cited therein.

Of fundamental interest to the background of the present invention are the prior identification and characterization of certain mediators of cell adhesion events, the "leukointegrins," LFA-1, MAC-1 and gp 150.95 (referred to in WHO nomenclature as CD18/CD11a, CD18/CD11b, and CD18/CD11c, respectively) which form a subfamily of heterodimeric "integrin" cell surface proteins present on B lymphocytes, T lymphocytes, monocytes and granulocytes. See, e.g., Table 1 of Springer, supra, at page 429. Also of interest are other single chain adhesion molecules (CAMs) that have been implicated in leukocyte activation, adhesion, motility and the like, which are events attendant to the inflammatory process. For example, it is presently believed that prior to the leukocyte extravasation which characterizes inflammatory processes, activation of integrins constitutively expressed on leukocytes occurs and is followed by a tight ligand/receptor interaction between the integrins (e.g., LFA-1) and one or both of two distinct intercellular adhesion molecules (ICAMs) designated ICAM-1 and ICAM-2 which are expressed on blood vessel endothelial cell surfaces and on other leukocytes.

Like the other CAMs characterized to date, [e.g., vascular adhesion molecule (VCAM-1) as described in PCT WO 90/13300 published Nov. 15, 1990; and platelet endothelial cell adhesion molecule (PECAM-1) as described in Newman et al., *Science*, 247: 1219–1222 (1990) and PCT WO 91/10683 published Jul. 25, 1991], ICAM-1 and ICAM-2 are structurally homologous to other members of the immunoglobulin gene superfamily in that the extracellular portion of each is comprised of a series of domains sharing a similar carboxy terminal motif. A "typical" immunoglobulin-like domain contains a loop structure usually anchored by a disulfide bond between two cysteines at the extremity of each loop. ICAM-1 includes five immunoglobulin-like domains; ICAM-2, which differs from ICAM-1 in terms of cell distribution, includes two such domains; PECAM-1 includes six; VCAM includes six or seven, depending on splice variations, and so on. Moreover, CAMs typically include a hydrophobic "transmembrane" region believed to participate in orientation of the molecule at the cell surface and a carboxy terminal "cytoplasmic" region. Graphic models of the operative disposition of CAMs generally show the molecule anchored in the cell membrane at the transmembrane region with the cytoplasmic "tail" extending into the cell cytoplasm and one or more immunoglobulin-like loops extending outward from the cell surface.

A number of neuronal cells express surface receptors with extracellular Ig-like domains, structurally similarity to the ICAMs. See for example, Yoshihara, et al., supra. In addition to Ig-like domains, many adhesion molecules of the nervous system also contain tandemly repeated fibronectin-like sequences in the extracellular domain.

A variety of therapeutic uses has been projected for intercellular adhesion molecules, including uses premised on the ability of ICAM-1 to bind human rhinovirus. European Patent Application 468 257 A published Jan. 29, 1992, for example, addresses the development of multimeric configurations and forms of ICAM-1 (including full length and truncated molecular forms) proposed to have enhanced ligand/receptor binding activity, especially in binding to viruses, lymphocyte associated antigens and pathogens such as *Plasmodium falciparum*.

In a like manner, a variety of uses has been projected for proteins immunologically related to intercellular adhesion molecules. WO91/16928, published Nov. 14, 1991, for example, addresses humanized chimeric anti-ICAM-1 antibodies and their use in treatment of specific and non-specific inflammation, viral infection and asthma. Anti-ICAM-1 antibodies and fragments thereof are described as useful in treatment of endotoxic shock in WO92/04034, published Mar. 19, 1992. Inhibition of ICAM-1 dependent inflammatory responses with anti-ICAM-1 anti-idiotypic antibodies and antibody fragments is addressed in WO92/06119, published Apr. 16, 1992.

Despite the fundamental insights into cell adhesion phenomena which have been gained by the identification and characterization of intercellular adhesion proteins such as ICAM-1 and lymphocyte interactive integrins such as LFA-1, the picture is far from complete. It is generally believed that numerous other proteins are involved in inflammatory processes and in targeted lymphocyte movement throughout the body. For example, U.S. patent application Ser. Nos. 07/827,689, 07/889,724, 07/894,061 and 08/009,266 all now abn and corresponding published PCT Application WO 93/14776 (published Aug. 5, 1993) disclose the cloning and expression of an ICAM-Related protein, ICAM-R. The disclosures of these applications are specifically incorporated by reference herein and the DNA and amino acid sequences of ICAM-R are set out in SEQ ID NO. 4 herein. This new ligand has been found to be expressed on human lymphocytes, monocytes and granulocytes.

Of particular interest to the present application, still another ICAM-like surface molecule was identified which has a tissue specific expression unlike that of any known ICAM molecule. Mori, et al., [*Proc.Natl.Acad.Sci.(USA)* 84:3921–3925 (1987)] reported identification of a telencephalon-specific antigen in rabbit brain, specifically immunoreactive with monoclonal antibody 271A6. This surface antigen was named telencephalin. Imamura, et al., [*Neurosci.Letts.* 119:118–121 (1990)], using a polyclonal antibody to assess localized expression, asserted that expression of telencephalin in visual cortex of cats showed variation in layers of the tissue, and also reported telencephalin expression was variable as a function of development. Oka, et al., [*Neuroscience* 35:93–103 (1990)] subsequently reported isolation of telencephalin using monoclonal antibody 271A6. The publication reports a molecular weight for the surface molecule of about 500 kD and that the molecule was composed of four subunits, each with a native molecular weight of 130 kD and approximately 100 kD following N-glycanase treatment. Yoshihiro, et al., [*Neuroscience, Research Supplement* 18, p. S83 (1994)], reported the cDNA and amino acid sequences for rabbit telencephalin at the 17th Annual Meeting of the Japan Neuroscience Society in Nagoya, Japan, Dec. 7–9, 1993, and the 23rd Annual Meeting of the Society for Neuroscience in Washington, D.C., Nov. 9, 1993 [Society for Neuroscience Abstracts 19 (1–3) p. 646 (1993)]. The deduced amino acid sequence reported suggested that the 130 kD telencephalon is an integral membrane protein with nine extracellular immunoglobulin (Ig)-like domains. The distal eight of these domains showed homology to other ICAM Ig-like domains. This same information was reported by Yoshihara, et al., in *Neuron* 12:543–553 (1994).

There thus continues to be a need in the art for the discovery of additional proteins participating in human cell-cell interactions and especially a need for information serving to specifically identify and characterize such proteins in terms of their amino acid sequence. Moreover, to the extent that such molecules might form the basis for the development of therapeutic and diagnostic agents, it is essential that the DNA encoding them be elucidated. Such seminal information would inter alia, provide for the large scale production of the proteins, allow for the identification of cells naturally producing them, and permit the preparation of antibody substances or other novel binding proteins specifically reactive therewith and/or inhibitory of ligand/receptor binding reactions in which they are involved.

BRIEF SUMMARY OF THE INVENTION

In one of its aspects, the present invention provides purified and isolated polynucleotides (e.g., DNA sequences, RNA transcripts and anti-sense oligonucleotides thereof) encoding a novel polypeptide, "ICAM-4," as well as polypeptide variants (including fragments and deletion, substitution, and addition analogs) thereof which display one or more ligand/receptor binding biological activities and/or immunological properties specific to ICAM-4. ICAM-4-specific ligand/receptor binding biological activities encompass interactions of both the ICAM-4 extracellular and cytoplasmic domains with other molecules (e.g., in processes of cell-cell adhesion and/or signal transduction). Preferred DNA sequences of the invention include genomic and cDNA sequences as well as wholly or partially chemically synthesized DNA sequences. A presently preferred polynucleotide is set out in SEQ ID NO: 1 and encodes rat species ICAM-4. Biological replicas (i.e., copies of isolated DNA sequences made in vivo or in vitro) of DNA sequences of the invention are contemplated. Also provided are autonomously replicating recombinant constructions such as plasmid and viral DNA vectors incorporating ICAM-4 sequences and especially vectors wherein DNA encoding ICAM-4 or an ICAM-4 variant is operatively linked to an endogenous or exogenous expression control DNA sequence.

According to another aspect of the invention, host cells, especially unicellular host cells such as procaryotic and eucaryotic cells, are stably transformed with DNA sequences of the invention in a manner allowing the desired polypeptides to be expressed therein. Host cells expressing such ICAM-4 and ICAM-4 variant products can serve a variety of useful purposes. To the extent that the expressed products are "displayed" on host cell surfaces, the cells may constitute a valuable immunogen for the development of antibody substances specifically immunoreactive with ICAM-4 and ICAM-4 variants. Host cells of the invention are conspicuously useful in methods for the large scale production of ICAM-4 and ICAM-4 variants wherein the cells are grown in a suitable culture medium and the desired polypeptide products are isolated from the cells or from the medium in which the cells are grown.

Novel ICAM-4 of the invention may be obtained as isolates from natural cell sources, but, along with ICAM-4 variant products, are preferably produced by recombinant procedures involving host cells of the invention. A presently preferred amino acid sequence for an ICAM-4 polypeptide is set out in SEQ ID NO: 2. The products may be obtained in fully or partially glycosylated, partially or wholly de-glycosylated, or non-glycosylated forms, depending on the host cell selected for recombinant production and/or post-isolation processing. ICAM-4 variants of the invention may comprise water soluble or insoluble monomeric, multimeric or cyclic ICAM-4 fragments which include all or part of one or more of the domain regions specified above and having a biological or immunological property of ICAM-4 including, e.g., the ability to bind to a binding partner of ICAM-4 and/or inhibit binding of ICAM-4 to a natural binding partner. ICAM-4 variants of the invention may also comprise polypeptide analogs wherein one or more of the specified amino acids is deleted or replaced: (1) without loss, and preferably with enhancement, of one or more biological activities or immunological characteristics specific for ICAM-4; or (2) with specific disablement of a particular ligand/receptor binding function. Analog polypeptides including additional amino acid (e.g., lysine or cysteine) residues that facilitate multimer formation are contemplated.

Also comprehended by the present invention are antibody substances (e.g., monoclonal and polyclonal antibodies, antibody fragments, single chain antibodies, chimeric antibodies, CDR-grafted antibodies and the like) and other binding proteins (e.g., polypeptides and peptides) which are specific (i.e., non-reactive with the ICAM-1, ICAM-2, and ICAM-R intercellular adhesion molecules to which ICAM-4 is structurally related) for ICAM-4 or ICAM-4 variants. The invention also comprehends hybridoma cell lines which specifically secrete monoclonal antibodies of the invention. Presently preferred hybridomas of the invention include those designated 127A, 127H, 173E, 179I, and 179H. Antibody substances can be developed using isolated natural or recombinant ICAM-4 or ICAM-4 variants or cells expressing such products on their surfaces. Binding proteins of the invention are additionally useful for characterization of binding site structure(s) (e.g., epitopes and/or sensitivity of binding properties to modifications in ICAM-4 amino acid sequence).

Binding proteins are useful, in turn, in compositions for immunization as well as for purifying polypeptides of the invention and identifying cells displaying the polypeptides on their surfaces. They are also manifestly useful in modulating (i.e., blocking, inhibiting or stimulating) ligand/ receptor binding biological activities involving ICAM-4, especially those ICAM-4 effector functions involved in specific and non-specific immune system responses. Anti-idiotypic antibodies specific for anti-ICAM-4 antibody substances and uses of such anti-idiotypic antibody substances in modulating immune responses are also contemplated. Assays for the detection and quantification of ICAM-4 on cell surfaces and in body fluids, such as serum or cerebrospinal fluid, may involve, for example, a single antibody substance or multiple antibody substances in a "sandwich" assay format. In detecting ICAM-4 in a body fluid, antibodies of the invention are also useful for assessing the occurrence of neuropathologies which can be correlated to increased levels of circulating ICAM-4. Such neuropathologies include, but are not limited to, cerebral ischemia (i.e., stroke) resulting from various disorders including, for example, thrombosis, embolism, and the like.

The scientific value of the information contributed through the disclosures of DNA and amino acid sequences of the present invention is manifest. As one series of examples, knowledge of the sequence of a cDNA for ICAM-4 makes possible the isolation by DNA/DNA hybridization of genomic DNA sequences encoding ICAM-4 and specifying ICAM-4 expression control regulatory sequences such as promoters, operators and the like. DNA/DNA hybridization procedures carried out with DNA sequences of the invention and under stringent conditions are likewise expected to allow the isolation of DNAs encoding allelic variants of ICAM-4, other structurally related proteins sharing one or more of the biological and/or immunological properties specific to ICAM-4, and proteins homologous to ICAM-4 from other species. DNAs of the invention are useful in DNA/RNA hybridization assays to detect the capacity of cells to synthesize ICAM-4. Also made available by the invention are anti-sense polynucleotides relevant to regulating expression of ICAM-4 by those cells which ordinarily express the same. As another series of examples, knowledge of the DNA and amino acid sequences of ICAM-4 makes possible the generation by recombinant means of ICAM-4 variants such as hybrid fusion proteins (sometimes referred to as "immuno-adhesions") characterized by the presence of ICAM-4 protein sequences and immunoglobulin heavy chain constant regions and/or hinge regions. See, Capon et al., *Nature*, 337:525-531 (1989); Ashkenazi et al., *P.N.A.S. (USA)*, 88: 10535-10539 (1991); and PCT WO 89/02922, published Apr. 6, 1989. ICAM-4 variant fusion proteins may also include, for example, selected extracellular domains of ICAM-4 and portions of other cell adhesion molecules.

DNA of the invention also permits identification of untranslated DNA sequences which specifically promote expression of polynucleotides operatively linked to the promoter regions. Identification and use of such promoter sequences are particularly desirable in instances, for example gene transfer, which can specifically require heterologous gene expression in a limited neuronal environment. The invention also comprehends vectors comprising promoters of the invention, as well as chimeric gene constructs wherein the promoter of the invention is operatively linked to a heterologous polynucleotide sequence and a transcription termination signal.

The DNA and amino acid sequence information provided by the present invention also makes possible the systematic analysis of the structure and function of ICAM-4 and definition of those molecules with which it will interact on extracellular and intracellular levels. The idiotypes of anti-ICAM-4 monoclonal antibodies of the invention are representative of such molecules and may mimic natural binding proteins (peptides and polypeptides) through which ICAM-4 intercellular and intracellular activities are modulated or by which ICAM-4 modulates intercellular and intracellular events. Alternately, they may represent new classes of modulators of ICAM-4 activities. Anti-idiotypic antibodies, in turn, may represent new classes of biologically active ICAM-4 equivalents. In vitro assays for identifying antibodies or other compounds that modulate the activity of ICAM-4 may involve, for example, immobilizing ICAM-4 or a natural ligand to which ICAM-4 binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of ICAM-4 binding.

The DNA sequence information provided by the present invention also makes possible the development, by homologous recombination or "knockout" strategies [see, e.g., Capecchi, *Science*, 244: 1288-1292 (1989)], of rodents that fail to express a functional ICAM-4 protein or that express a variant ICAM-4 protein. Such rodents are useful as models for studying the activities of ICAM-4 and ICAM-4 modulators in vivo.

DETAILED DESCRIPTION OF THE INVENTION

The disclosures of parent U.S. patent application Ser. No. 08/102,852, filed Aug. 5, 1993, now abn, are specifically incorporated by reference. The examples of that application address, inter alia: design and construction of oligonucleotide probes for PCR amplification of ICAM related DNAs; use of the probes to amplify a human genomic fragment homologous to, but distinct from DNAs encoding ICAM-1 and ICAM-2; screening of cDNA libraries with the genomic fragment to isolate additional ICAM-R coding sequences; screening of cDNA libraries to isolate a full length human cDNA sequence encoding ICAM-R; characterization of DNA and amino acid sequence information for ICAM-R, especially as related to ICAM-1 and ICAM-2; development of mammalian host cells expressing ICAM-R; assessment of indications of ICAM-R participation in adhesion events involving CD18-dependent and CD18-independent pathways; inhibition of cell adhesion to ICAM-R by ICAM-R-derived peptides; expression of variants of ICAM-R; preparation and characterization of anti-ICAM-R antibodies and fragments thereof; mapping of ICAM-R epitopes recognized by anti-ICAM-R monoclonal antibodies; assessment of the distribution and biochemical characterization of ICAM-R and RNA encoding the same; assessment of ICAM-R in homotypic cell-cell adhesion and immune cell activation/ proliferation; characterization of ICAM-R monoclonal antibodies; and assessment of differential phosphorylation and cytoskeletal associations of the cytoplasmic domain of ICAM-R. Also disclosed was the identification of a rodent ICAM-encoding DNA that, at the time, appeared to be the rat homolog of human ICAM-R, and the use of this DNA to construct and express DNAs encoding glutathione-S-transferase fusion proteins. The detailed description of how this rodent DNA was identified can be found in the parent application (U.S. Ser. No. 08/102,852 now abn) in Example 6, and is reproduced herein as Example 1. As more of the rodent ICAM-coding sequence was identified, it became apparent that the rodent ICAM DNA did not encode a rat species homolog of human ICAM-R, but, in fact, encoded a novel ICAM polypeptide, herein named ICAM-4. In order to appreciate the events which led to the identification of ICAM-4, a chronology is provided which is followed by a detailed description of the invention.

A first rodent genomic ICAM-4 sequence was identified which encoded a region homologous to domain 2 (herein SEQ ID NO: 3, and SEQ ID NO: 23 of U.S. Ser. No. 08/102,852 now abn) of human ICAM-R (herein as SEQ ID NO: 4). A second, overlapping genomic DNA (herein SEQ ID NO: 5, and SEQ ID NO: 26 of U.S. Ser. No. 08/102,852 now abn) was also identified which encoded both the domain 2 region of SEQ ID NO: 3, and sequences for ICAM-1. Using SEQ ID NO: 3 as a probe, a rodent spleen cDNA (herein SEQ ID NO: 6, and SEQ ID NO: 25 in U.S. Ser. No. 08/102,852 now abn) was identified which encoded domains 2 through 5 as well as a fifth domain not previously observed as an ICAM domain. At this time, these newly identified rodent DNAs appeared to encode a rodent homolog of human ICAM-R, however alignment of 3' regions of these DNAs with other ICAMs proved difficult.

The subsequent isolation of a 1 kb cDNA clone from a rat spleen library, and amplification of an RT-PCR fragment indicated that a portion of both the cDNA and genomic clones had not been sequenced. Another RT-PCR amplification product (SEQ ID NO: 7) confirmed this omission. It was determined that a fragment of 177 bp was excised from the genomic and cDNA clones by EcoRI digestion of the clones to isolate these sequences from λ phage for DNA sequencing studies. Reanalysis of SEQ ID NOs: 5 and 6 in light of these other sequences permitted identification of more accurate and complete sequences for the originally isolated genomic and cDNA clones, presented in corrected form herein as SEQ ID NOs: 8 and 9.

In order to identify a complete coding sequence for ICAM-4, a rat brain cDNA (SEQ ID NO: 10) was isolated, and 5' end sequence determined by 5' rapid amplification of cDNA ends (5' RACE), the amplification product set forth in SEQ ID NO: 11. Combining information from the RT-PCR clone (SEQ ID NO: 7), the brain cDNA (SEQ ID NO: 10) and the RACE amplification product (SEQ ID NO: 11) permitted identification of the complete coding sequence for ICAM-4 (SEQ ID NO: 1).

The present invention is thus illustrated by the following examples. More particularly, Example 1 addresses cloning of a partial rodent ICAM-4 DNA. Example 2 describes Northern blot analysis of rodent ICAM-4 transcription. Example 3 describes isolation of a full length rodent ICAM-4 cDNA. Example 4 relates the in situ hybridization of rodent ICAM-4 in brain tissue. Example 5 addresses generation of ICAM-4 fusion proteins in prokaryotes. Example 6 describes production of monoclonal antibodies specific for rat ICAM-4/GST fusion proteins. Example 7 describes expression of soluble rat ICAM-4 proteins in a baculovirus expression system. Example 8 addresses production of monoclonal antibodies specific for rat ICAM-4 expressed in a baculovirus system. Example 9 describes immunocytochemical analysis of rat ICAM-4 expression. Example 10 relates cloning of a human genomic ICAM-4-encoding DNA. Example 11 addresses cloning of a human ICAM-4-encoding cDNA. Example 12 describes Northern analysis of human ICAM-4 expression. Example 13 describes generation of human ICAM-4/GST fusion proteins. Example 14 addresses production of monoclonal antibodies immunospecific for human ICAM-4. Example 15 describes development of a capture assay for determining the concentration of soluble ICAM-4 in a particular fluid. Example 16 applies the capture assay method in assessing ICAM-4 concentration in the serum of stroke patients. Example 17 relates to assessment of ICAM-4 transcription in a rat epilepsy model. Example 18 addresses cloning of a promoter region for human ICAM-4.

EXAMPLE 1

Cloning of Rat ICAM-Related DNA

A. Isolation of a Rat Genomic ICAM-Related Domain 2 DNA

A rat genomic library constructed in λ EMBL3 was screened a with [$^{32}$P]-labeled probe generated by PCR from DNA encoding human ICAM-3 domain 2 The sequence of the probe is set forth in SEQ ID NO: 12. Library plaques were transferred to Hybond N+ nylon membranes (Amersham, Arlington Heights, Ill.). Screening of all cDNA and genomic libraries was performed according to standard protocols. Prehybridization and hybridizations were carried out in a solution of 40–50% formamide, 5× Denhardt's, 5× SSPE and 1.0% SDS at 42° C. Probes ([$^{32}$P]-labeled) were added at a concentration of $10^5$–$10^6$ cpm/ml of hybridization solution. Following 16–18 hours of hybridization, nylon membranes were washed extensively at room temperature in 2× SSPE with 0.1% SDS and subsequently exposed to X-ray film at −80° C. overnight. Positive plaques were subjected to one or more rounds of hybridization to obtain clonal phage. DNA prepared from lysate of the positive clones was subcloned into pBS+ and sequenced.

A first genomic clone encoding a rat ICAM-related domain 2 was identified that was determined to be homologous to domain 2 regions in other ICAM family members (see for example, Table 1 of U.S. patent application Ser. No. 08/102,852 now abn), yet was distinct from the previously reported nucleotide sequences for rat ICAM-1 [Kita, et al., Biochem.Biophys.Acta 1131:108–110 (1992)] or mouse ICAM-2 [Xu, et al., J.Immunol. 149:2560–2565 (1992)]. The nucleic acid and deduced amino acid sequences for this clone were disclosed in the co-pending parents to the present application as purportedly variant forms of rat ICAM-R and were set forth as SEQ ID NOs: 23 and 24, respectively, in U.S. Ser. No. 08/102,852 now abn. Herein, these same sequences are set out in SEQ ID NOs: 3 and 13, respectively.

A second, overlapping clone was also identified with the same probes and was determined to contain the ICAM domain 2 sequence of SEQ ID NO: 3 and 5' DNA encoding at least part of rat ICAM-1. The nucleic acid sequence for this clone was set forth in the co-pending parent to the present application as SEQ ID NO: 26 and is set forth herein as SEQ ID NO: 5. This second clone indicated that the ICAM-related gene fragment of the first clone and the gene encoding rat ICAM-1 are located on the same rat chromosome within 5 kb of each other.

B. Isolation of Rat ICAM-Related cDNA

In order to identify a more complete protein coding sequence for the ICAM-related polypeptide, [$^{32}$P]-labeled DNA encoding the domain 2 sequence from the rat genomic clone identified in Section A (SEQ ID NO: 3), supra, was used to screen a number of cDNA libraries from various rat and mouse cell types, including rat macrophage (Clontech, Palo Alto, Calif.), peripheral blood lymphocyte (PBL) (Clontech), T cell (constructed in-house), and spleen (Clontech), and mouse PBL (Clontech), T cell (constructed in-house), and B cell (constructed in-house).

A single clone was identified in a rat spleen cDNA library (Clontech) which contained five Ig-like domains, four of which were homologous to domains 2 through 5 in both ICAM-1 and ICAM-R. Moreover, this clone included 3' DNA encoding an apparent fifth Ig-like domain which had not been previously identified in any other ICAM polypeptide. In addition, the clone contained an unusual 3' sequence subsequently determined to be a partial intron (discussed infra) located between domains 4 and 5, suggesting that the clone was the product of an immature or aberrantly spliced transcript. The presence of the unique domain and the determination that the 3' region did not properly align with other known ICAMs suggested that the ICAM-related DNA potentially encoded a novel rat ICAM polypeptide. The nucleic acid sequence for this clone was set forth in the parent to the present application as SEQ ID NO: 25; herein the nucleic acid sequence for this spleen cDNA clone is set forth in SEQ ID NO: 6.

C. Re-analysis of Rat cDNA and Genomic DNAs

Subsequent to the Aug. 5, 1993 filing of U.S. patent application Ser. No. 08/102,852 now abn, it was determined that the partial rat spleen cDNA clone (SEQ ID NO: 25 in the parent and SEQ ID NO: 6 herein) and the rat liver genomic clone (SEQ ID NO: 26 of the parent and SEQ ID NO: 5 herein) were missing an internal 177 bp EcoRI fragment that was part of each of these clones but lost in a subcloning step when the library inserts were removed from the λ vector with EcoRI digestion and ligated into a sequencing vector. The observation that the cDNA and genomic clones might be missing a coding fragment became apparent upon alignment of the rat genomic and cDNA sequences with various RT-PCR amplification products, including SEQ ID NO: 7, which revealed a gap in the rat sequence.

Subsequent isolation and sequence alignment of a cDNA from a spleen library using the spleen cDNA clone (SEQ ID NO: 6) as a probe provided a first indication that a portion of the spleen cDNA and genomic clones were not sequenced. Further confirmation of this idea became apparent upon amplification of an RT-PCR fragment, spanning domains 3 through 5, using a 5' primer (RRD3 5'Xho, containing a 5' XhoI restriction site to facilitate cloning) set out in SEQ ID NO: 14, and a 3' primer (RRD5 3'Hind, containing a HindIII site to facilitate cloning) set out in SEQ ID NO: 15.

GAACTCGAGGCCATGCCTCCACTTTCC (SEQ ID NO: 14)

CCATAAGCTTTATTCCACCGTGACAGCCAC (SEQ ID NO: 15)

Alignment of these two DNAs clearly revealed that the cDNA and genomic clones had lost a fragment prior to sequencing; this idea was further supported following sequencing of the RT-PCR DNA discussed infra. It was concluded that restriction digestion with EcoRI to remove the cDNA and genomic fragments prior to sequencing resulted in the excision of a 177 bp fragment that was not detected visually in the agarose gel separation of the clones from the λ phage sequences. Subsequent sequence analysis confirmed the location of two EcoRI sites flanking a 177 bp fragment in both of the original clones.

The 177 bp EcoRI fragment is situated between nucleotides 719 and 896 in the rat partial cDNA clone as set out in SEQ ID NO: 9 and between nucleotides 2812 and 2989 in the partial genomic clone as set out in SEQ ID NO: 8.

D. DNA Isolated by RT-PCR Clone

RT-PCR was utilized to generate more complete sequence information for the rat ICAM-related gene. Sequence information from the genomic clone (SEQ ID NO: 3) was used to design sense primers complementary to a region 5' of the protein coding region, as determined from the cDNA clone, and antisense primers designed complementary to coding sequences and regions 3' to the coding sequence in the cDNA clone (SEQ ID NO: 6).

Template cDNA for PCR reactions was prepared as follows. Approximately 2 µg of poly A⁺RNA isolated from rat spleen cells was denatured by heating at 65° C. in a 10 µl volume. Following denaturation, 0.1 µl RNasin (Invitrogen, San Diego, Calif.), 5 µl 5× RTase Buffer (BRL, Bethesda, Md.), 2 µl random hexamer (pd(N)6 at 100 µg/ml) (Pharmacia, Piscataway, N.J.), 6 µl dNTPs (2 mM each) and 2 µl AMV RTase (BRL) were added and the reaction was incubated at 42° C. for 60–90 min. Reactions were stored at −20° C. until needed.

An initial series of experiments was conducted to identify oligonucleotides primer pairs that produced an amplification product in PCR reactions using rat spleen cDNA as the template. Various 5' sense primers were paired in PCR with a 3' primer which was designed to be complementary to an internal, coding sequence; the 3' primer was designated RRD2 3-1 and is set forth in SEQ ID NO: 16.

AACGTGCGGAGCTGTCTG (SEQ ID NO: 16)

(In the ultimately isolated RT-PCR product, SEQ ID NO: 7, infra, primer RRD2 3-1 corresponded to nucleotides 719 through 736.) Similarly, various 3' antisense primers were paired with a 5' primer designed complementary to another internal, coding sequence; the 5' primer in these reactions was designated RGen3900S and is set forth in SEQ ID NO: 17.

ACGGAATTCGAAGCCATCAACGCCAGG (SEQ ID NO: 17)

(In SEQ ID NO: 7, infra, primer RGen3900S corresponded to nucleotides 1719 through 1736.) Based on the size of the amplification products and the ability of these products to hybridize with the partial cDNA clone, one pair of primers was determined to be most efficient and was used in subsequent PCR amplifications. The 5' primer was designated RGen780S (SEQ ID NO: 18) and the 3' primer was designated RGen4550AS (SEQ ID NO: 19).

CATGAATTCCGAATCTTGAGTGGGATG (SEQ ID NO: 18)

ATAGAATTCCTCGGGACACCTGTAGCC (SEQ ID NO: 19)

(In SEQ ID NO: 7, infra, primer RGen780S corresponded to nucleotides 1 through 18, and primer RGen4550AS corresponded to nucleotides 2197 through 2214.)

This primer pair was used in PCR under a variety of conditions to optimize amplification. A total of 15 different PCR buffers that varied in pH and Mg⁺⁺ concentration were used at two different annealing temperatures, and a sample of the product from each reaction was separated on a 1% agarose gel. Because no amplification product could be detected by visual inspection of the ethidium bromide stained gel from any of the reaction conditions, more sensitive Southern hybridization was employed to detect the PCR products.

Aliquots of the amplified DNA were separated by electrophoresis, transferred to a Hybond N+ nylon membrane using conventional Southern blotting wicking techniques, and hybridized with the entire rat cDNA which was [³²P]-labeled. Hybridization conditions were essentially as described for the library screening procedure in Section A, supra. Autoradiography indicated that a small amount of DNA of approximately 2.2 kb had been generated in two of the reactions, and the remainder of the amplification product from the two reactions was separated on an agarose gel. The 2.2 kb region was eluted from the gel, even though no band was evident upon visual inspection, and used as a template in another PCR reaction using the same primers (SEQ ID NOs: 18 and 19), Tris-HCl buffer, pH 8.0, containing 1 mM $Mg^{++}$, and 55° C. annealing temperature. The amplification product from the secondary PCR was visible in the gel and was eluted and cloned into a $pBS^+$ plasmid (Stratagene, La Jolla, Calif.) for sequence analysis.

The resulting RT-PCR clone was determined to contain 2214 bp as set forth in SEQ ID NO: 7. The clone encoded domains 2 through 6 found in the rat spleen cDNA clone, an additional amino terminal domain 1, an additional carboxy terminal domain 7, and 164 bp of what appeared to be a further carboxy terminal domain 8. Immediately 5' to domain 1 was an additional 144 bp sequence presumed to have been derived from an intron between the leader and the first domain. This clone did not contain a 5' leader sequence or 3' transmembrane and cytoplasmic regions. In addition to the previously identified domain 6 in the spleen cDNA clone, the 7th and 8th domains in the RT-PCR clone supported the hypothesis that this clone was a novel rodent ICAM.

EXAMPLE 2

Northern Blot Analysis

In order to further investigate the possibility that the ICAM-related clones identified in Example 1 encoded a novel ICAM polypeptide as suggested by the unique Ig-like domains, tissue specific expression was examined by Northern blot analysis to permit comparison with the previously reported expression patterns of human ICAMs [ICAM-1, Dustin, et al., *J.Immunol.* 137:245–254 (1986); ICAM-2, Staunton, et al., *Nature* 339:61–64 (1989); ICAM-R, de Fourgerolles and Springer, *J.Exp.Med.* 175:185–190 (1992)].

Total cellular RNA from rat lung, brain, spinal cord, liver, digestive tract, thymus, lymph nodes, and spleen was prepared using STAT60 RNA isolation reagents (Tel-test "B", Inc. Friendswood, Tex.) according to the manufacturer's suggested protocol. Poly $A^+$ RNA was purified from total RNA using oligo dT cellulose columns. Approximately 5 μg of RNA derived from each tissue was separated on a 1% formaldehyde agarose gel, and transferred to hybond-C nitrocellulose membranes (Amersham).

A fragment of the rat spleen cDNA from Example 1 corresponding to domains 2 through 4 (nucleotides 1 through 724 in SEQ ID NO: 6) was subcloned into pBluescript $SK^+$ (Stratagene) and an antisense riboprobe was generated by in vitro transcription using $^{32}$P-labeled UTP and approximately 500 ng of linearized template according to a manufacturer's (Boehringer Mannheim, Indianapolis, Ind.) suggested protocol. The membrane-bound RNA was prehybridized in a solution containing 50% formamide, 5× SSC, 1× PE (50 mM Tris-HCl, pH 7.5, 0.1% sodium pyrophosphate, 0.2% polyvinylpyrrolidone, 0.2% ficoll, 5 mM EDTA, 1% SDS) and 150 μg/ml denatured salmon sperm DNA. The radiolabeled probe was denatured by boiling and added to the prehybridization solution to a final concentration of $1\times10^6$ cpm/ml. Hybridization was allowed to proceed for 16–18 hours at 65° C. The membranes were then washed at 65° C. in 2× SSC containing 0.1% SDS and subsequently exposed to X-ray film for 3–16 hours.

The Northern blot analysis indicated that the ICAM-related cDNA identified in Example 1 was expressed only in rat brain, a tissue specificity not previously reported for any other ICAM polypeptides. This expression pattern, in combination with the unique Ig-like domains not known to exist in other ICAM polypeptides, indicated that the ICAM-related clone was a novel member of the ICAM family of proteins, and was named ICAM-4.

The fact that the initially identified cDNA clones were detected in a rat spleen library suggested that a subset of cells in the spleen may express ICAM-4 at low levels. However, a properly spliced clone could not be detected in numerous hemopoietic cDNA libraries which led to doubt if ICAM-4 protein is actually expressed in tissue other than brain. One explanation for the detection of ICAM-4 cDNA in spleen is that the sensitivity of PCR may have amplified a trace amount of transcript even though these tissues do not express the encoded protein.

EXAMPLE 3

Isolation of Full Length Rat ICAM-4 cDNA

A. Identification of a Rat Brain cDNA Clone

In view of the tissue specific expression of ICAM-4, brain tissue mRNA was utilized in an attempt to isolate a full length cDNA encoding ICAM-4. Two probes, one complementary to domains 1 through 2 and a second complementary to domains 3 through 5 of the spleen cDNA clone identified in Example 1 (SEQ ID NO: 7), were radiolabeled and used to screen a rat brain cDNA library in λgt10 which was previously constructed in-house. Hybridization conditions were as described in Example 1, and positive plaques were subjected to one or more rounds of screening to obtain clonal phage.

Nine positive clones were identified, two of which hybridized to both probes. The longest of the two clones, designated clone 7, contained 2550 bp encoding four of the five Ig-like domains found in the probe cDNA. In addition, clone 7 encoded four other Ig-like domains not found in the probe. Putative transmembrane and cytoplasmic domains were identified which were followed by a stop codon, a polyadenylation signal, and a poly A tail. Clone 7 was lacking at least one 5' Ig-like domain as determined by comparison to the RT-PCR clone (SEQ ID NO: 7), and also lacked a leader sequence; re-screening of the library did not yield any longer clones which contained these sequences. The nucleic acid sequence for clone 7 is set forth in SEQ ID NO: 10.

B. Determination of the 5' End

In order to isolate domain 1 and other 5' sequences, a PCR technique termed 5' Rapid Amplification of cDNA Ends (RACE) [*PCR Protocols: A Guide to Methods and Applications*, Innis, et al., (eds) Academic Press: New York (1990) pp:28–38] was employed using a 5' RACE kit (Clontech). This technique utilizes an internal primer paired with a second primer complementary to an adapter sequence ligated to the 5' end of cDNA library molecules. PCR with this primer pair will therefore amplify and facilitate identification of the intervening sequences. Overlapping sequence information can then be used to generate a complete sequence of the gene.

RACE-ready cDNA from rat brain (supplied with kit) was used in a PCR with the kit oligonucleotide and an antisense primer based on an internal ICAM-4 sequence. The 3' antisense primer, designated Spot714AS, was designed according to an ICAM-4 domain 4 sequence and is set forth in SEQ ID NO: 20.

CARGGTGACAAGGGCTCG (SEQ ID NO: 20)

The amplification product resulting from this primer pair was subsequently subjected to a secondary PCR using the same 5' kit primer paired with a 3' primer complementary to a region in ICAM-4 domain 1. The second 3' primer was designated RRACE2 and is set forth in SEQ ID NO: 21.

TATGAATTCAGTTGAGCCACAGCGAGC (SEQ ID NO: 21)

Each primer used in the secondary PCR contained an EcoR1 site to facilitate cloning of the resulting amplification products into pBS⁺ (Stratagene). The resulting plasmid DNA which contained the 5' end of the gene was identified by hybridization to a rat ICAM-4 domains 1 and 2 probe, corresponding to nucleotides 1 through 736 in SEQ ID NO: 7. Partial sequence information for domain 1 and the hydrophobic leader was determined from the resulting amplification product.

The product from the 5' RACE method was a DNA fragment 222 bp long containing 60 bp upstream of the initiating methionine residue, an 82 bp leader sequence, and an 80 bp sequence from domain 1. The amplification product is set forth in SEQ ID NO: 11.

C. Full Length Sequence of Rat ICAM-4

A composite clone of the full length ICAM-4 was constructed from the sequence information derived from the 5' RACE method (SEQ ID NO: 11), the RT-PCR clone (SEQ ID NO: 7) and the brain cDNA clone 7 (SEQ ID NO: 10). The full length gene for rat ICAM-4 was determined to contain 2985 bp with a single open reading frame encoding a deduced 917 amino acid protein. A putative Kozak sequence is located upstream of the methionine residue in the leader sequence. A 27 amino acid hydrophobic leader sequence is followed by nine Ig-like domains, a transmembrane region and a 58 amino acid cytoplasmic tail. The composite ICAM-4 cDNA is set for in SEQ ID NO: 1, and the deduced amino acid sequence is set forth in SEQ ID NO: 2.

Like other ICAM polypeptides, ICAM-4 contains extracellular, transmembrane, and cytoplasmic domains. In the extracellular domain, the amino terminus of ICAM-4 is a leader sequence comprising amino acids 1 through 27 which is followed by nine immunoglobulin (Ig)-like domains, a characteristic unique to ICAM-4 in that ICAM-1, ICAM-2, and ICAM-R contain five, two, and five extracellular Ig-like domain, respectively. In ICAM-4, domain 1 comprises amino acids 28 through 118; domain 2 comprises amino acids 119 through 224; domain 3 comprises amino acids 225 through 321; domain 4 comprises amino acids 322 through 405; domain 5 comprises amino acids 406 through 488; domain 6 comprises amino acids 489 through 569; domain 7 comprises amino acids 570 through 662; domain 8 comprises amino acids 663 through 742; and domain 9 comprises amino acids 743 through 830. Within each domain, a characteristic "loop" structure is formed by a disulfide bond between cysteine residues located generally at opposite ends of the domain amino acid sequence. Other structural features of ICAM-4 include the transmembrane region comprising amino acids 831 through 859 and the cytoplasmic region comprising amino acids 860 through 917.

Comparison of amino acid sequence homology of each domain in rat ICAM-4 with the other members of the ICAM family was limited to the corresponding sequences of human ICAM-1, ICAM-2, and ICAM-R since sequence information for all three rodent homologs has not been previously reported. In the first domain, the rodent ICAM-4 shows 21, 30, and 28 percent identity with human ICAM-1, ICAM-2, and ICAM-R, respectively. The second domain is more conserved, with the amino acid percent identities being 60, 42 and 62 with ICAM-1, -2, and -3, respectively. Domains 3–5 show percent identities of 48, 49, and 40 with ICAM-1 and 60, 59 and 29 respectively for ICAM-R. Interestingly, rat ICAM-4 domains 6 through 8 are most homologous with domain 5 (ranging from 29–42% identical), possibly arising from a gene segment duplication event. The ninth and final extracellular domain aligns poorly with other ICAM domains but has 22% identity with the 3rd and 6th domains of human VCAM-1, another member of the Ig family of protein which participate in cell adhesion. The cytoplasmic tail is 58 amino acids long. This is longer than the other members of the ICAM family wherein human ICAM-1, -2, and -3 contain 28, 26, and 37 amino acids, respectively. As with the ninth domain, rat ICAM-4 cytoplasmic tail is most homologous with the cytoplasmic tail of human VCAM-1, which contains only 19 amino acids. The membrane proximal 19 amino acids of rat ICAM-4 share 7 amino acid residue s with VCAM-1 (37%).

Finally, functional binding to LFA-1 (CD11a/CD18) maps to the first domain in the ICAMs. Vonderheide et al., [*J. Cell. Biol.*, 125:215–222 (1994)] identified a sequence motif purportedly involved in integrin binding. Despite the relatively low homology between rat ICAM-4 and other ICAMs in domain 1, this binding sequence motif is conserved, suggesting that rat ICAM-4 may be a ligand for LFA-1 and perhaps other integrins.

EXAMPLE 4

In situ Hybridization in Brain Tissue

In order to localize the specific brain tissue which expressed ICAM-4, in situ hybridization with ICAM-4 domain 1 and ICAM-4 domains 3 through 4 anti-sense riboprobes was employed. The probes were labeled by in vitro transcription using $^{35}$S-labeled UTP.

Frozen tissue sections of normal rat brain were fixed in 4% paraformaldehyde for 20 minutes, rinsed and dehydrated, and the fixed RNA denatured for 2 minutes in 2× SSC, 70% formamide at 70° C. prior to hybridization. Tissue sections were hybridized overnight at 50° C. in a solution containing 50% formamide, 0.3M NaCl, 20 mM Tris-HCl, pH 7.4, 5 mM EDTA, 10% dextran sulfate, 1× Denhardt, 0.5 mg/ml yeast RNA, 100 mM DTT and a probe concentration of 50,000 cpm/µl. Slides were washed once in 4× SSC, 10 mM DTT at room temperature for 60 minutes, once in 50% formamide, 2× SSC, 10 mM DTT at 60° C. for 40 minutes, and once in each 2× SSC and 1× SSC for 30 minutes each at room temperature. Specificity of hybridization was determined in parallel experiments performed with the same protocol but also including a more stringent wash in 50% formamide, 1× SSC, 10 mM DTT at 60° C. for 40 minutes. After washing, the slides were dipped in NTB2 emulsion (Kodak, Rochester, N.Y.) and exposed from 2 to 21 days before being developed and counter-stained. Negative controls included sense probes generated from ICAM-4 domain 1 and ICAM-4 domain 3 through 4 sense riboprobes, in addition to a human immunodeficiency virus (HIV-1) riboprobe.

The signal detected in brain tissue was primarily localized in the gray matter with the strongest signal in the cerebral cortex and hippocampus. The hybridization profile was consistent with ICAM-4 expression primarily in cerebral neurons.

EXAMPLE 5

Generation of ICAM-4 fusion proteins

Rat ICAM-4/glutathione S-transferase (GST) fusion proteins were generated using the prokaryote expression vector pGEX (Pharnacia, Alameda, Calif.) in order to generate monoclonal antibodies against specific ICAM-4 polypeptide fragments.

PCR primers corresponding to the 5' and 3' ends of domain 1 and the 5' and 3' ends of domain 2 were used to amplify DNA fragments encoding the individual domains. The resulting fragments were separately cloned into an EcoRI site of pGEX-2T; DNA sequence analysis confirmed the correct orientation and reading frame. Transformants were subsequently screened for their ability to produce fusion protein of the appropriate molecular weight.

Both ICAM-4 domain 1/GST and ICAM-4 domain 2/GST fusion proteins remained in the insoluble fraction after the bacteria were lysed by sonication in PBS containing 1% SDS. The insoluble protein fraction from 100 ml cultures were boiled in SDS loading dye and separated on a 10% preparative polyacrylamide-SDS gel. The gel was stained in ice cold 0.4M KCl and the fusion protein bands were excised. Fusion proteins were electroeluted from the gel slices in dialysis tubing in buffer containing 25 mM Tris-HCl and 192 mM glycine. Approximate protein concentration was determined by $OD_{280}$ and purity of the preparation was determined on SDS-PAGE stained with Coomasie blue.

EXAMPLE 6

Production of Monoclonal Antibodies Against Rat ICAM-4/GST Fusion Proteins

Balb/c mice were immunized by subcutaneous injection with 40–50 µg ICAM-4 domain-2/GST fusion protein (described in Example 5) emulsified in Freund's complete adjuvant (FCA). Two weeks later, the mice were again immunized by subcutaneous injection with the same protein, emulsified however in Freund's incomplete adjuvant. Two final intraperitoneal immunizations given two weeks after the second immunization included soluble antigen with no adjuvant given at two week intervals. Serum from each immunized mouse was assayed by ELISA for its ability to specifically react with rat ICAM-4 produced by the baculovirus expression system described infra.

The spleen from mouse #1654 was sterilely removed and placed in 10 ml serum-free RPMI 1640. A single-cell suspension was formed by grinding the spleen tissue between frosted ends of two glass microscope slides submerged in serum free RPMI 1640 (Gibco, Burlington, Ottawa, Canada) supplemented with 2 mM L-glutamine, 1 mM sodium pyruvate, 100 units/ml penicillin, and 100 µg/ml streptomycin. The cell suspension was filtered through a sterile 70-mesh Nitex cell strainer (Becton Dickinson, Parsippany, N.J.), and washed twice with RPMI followed by centrifuging at 200×g for 5 minutes. The resulting pellet from the final wash was resuspended in 20 ml serum-free RPMI. Thymocytes taken from three naive Balb/c mice were prepared in an identical manner.

Prior to fusion, NS-1 myeloma cells were maintained in log phase growth in RPMI with 11% Fetalclone serum (FBS) (Hyclone Laboratories, Logan, Utah) for three days. Once harvested, the cells were centrifuged at 200×g for 5 minutes, and the pellet was washed twice as described in the foregoing paragraph. After washing, the cell suspension was brought to a final volume of 10 ml in serum free RPMI. A 20 µl aliquot was removed and diluted 1:50 with serum free RPMI, and a 20 µl aliquot of this dilution was removed, mixed with 20 µl 0.4% trypan blue stain in 0.85% saline (Gibco), loaded onto a hemacytometer (Baxter Healthcare, Deerfield, Ill.) and the cells counted. Approximately 2.425× $10^8$ spleen cells were combined with 4.85×$10^7$ NS-1 cells, the mixture centrifuged and the supernatant removed. The resulting pellet was dislodged by tapping the tube and 2 ml of 50% PEG 1500 in 75 mM Hepes, pH 8.0, (Boehringer Mannheim, Indianapolis, Ind.) was added with stirring over the course of 1 minute. Subsequently, an additional 14 ml serum free RPMI was added over 7 minutes. The cell suspension was centrifuged at 200×g for 10 minutes and the supernatant discarded. The pellet was resuspended in 200 ml RPMI containing 15% FBS, 100 µM sodium hypoxanthine, 0.4 µM aminopterin, 16 µM thymidine (HAT) (Gibco), 25 units/ml IL-6 (Boehringer Mannheim) and 1.5×$10^6$ thymocytes/ml. The suspension was first placed in a 225 $cm^2$ flask (Corning, Essex, United Kingdom) at 37° C. for four hours before being dispensed into ten 96-well flat bottom tissue culture plates (Corning) at 200 µl/well. Cells in the plates were fed on days 3, 4, 5, and 6 post fusion by aspirating approximately 100 µl from each well with a 20 G needle (Becton Dickinson), and adding 100 µl/well plating medium described above except containing 10 units/ml IL-6 and lacking thymocytes.

The fusion plates were screened initially by antigen capture ELISA as follows. Immulon 4 plates (Dynatech, Cambridge, Mass.) were coated overnight at 4° C. with 100 ng/well of either domain 1-GST or domain 2-GST fusion protein in 50 mM carbonate buffer. The plates were blocked with 100 µl/well 0.5% fish skin gelatin (Sigma, St. Louis, Mo.) in PBS for 30 minutes at 37° C. After blocking, the plates were washed 3× with PBS containing 0.05% Tween 20 (PBST) and 50 µl/well of hybridoma supernatant from each fusion was added. After incubation at 37° C. for 30 minutes, the plates were washed as described above, and 50 µl of a 1:3500 dilution of horseradish peroxidase-conjugated goat anti-mouse IgG (Fc) (Jackson ImmunoResearch, West Grove, Pa.) was added. Plates were again incubated for 30 minutes and washed 4× with PBST. Substrate, 100 µl/well, consisting of 1 mg/ml o-phenylene diamine (Sigma) and 0.1 µl/ml 30% $H_2O_2$ in 100 mM citrate, pH 4.5, was added. The color reaction was allowed to proceed 10 minutes and quenched with the addition of 50 µl/well of 15% $H_2SO_4$. Absorbance at 490 nm was then determined on an automated plate reader (Dynatech).

Wells which were positive for domain 2-GST protein, but not for domain 1-GST protein, were then screened by ELISA against a Baculovirus supernatant (described infra). ELISA was performed as described above except that the Immulon 4 plates were initially coated overnight with Baculovirus supernatant diluted 1:4 in 50 mM carbonate buffer. Three wells (103A, 103B and 103F) were cloned two to three times, successively, by doubling dilution in RPMI, 15% FBS, 100 µM sodium hypoxanthine, 16 µM thymidine, and 10 units/ml IL-6. Wells of clone plates were scored visually after 4 days and the number of colonies in the least dense wells was recorded. Selected wells of each cloning were again assayed by ELISA after 7 to 10 days against either domain 1-GST protein and domain 2-GST protein, or Baculovirus supernatant.

The monoclonal antibodies produced by the hybridomas were isotyped by ELISA. Immulon 4 plates (Dynatech) were coated at 4° C. with 50 µl/well goat anti-mouse IgA, IgG, or IgM (Organon Teknika, Durham, N.C.) diluted 1:5000 in 50 mM carbonate buffer, pH 9.6. Wells were blocked for 30 minutes at 37° C. with 1% BSA in PBS, washed 3× with PBST. A 1:10 dilution of hybridoma culture supernatant (50 µl) was added to each plate, incubated, and washed as above. After removal of the last wash, 50 µl horseradish peroxidase-conjugated rabbit anti-mouse $IgG_1$, $G_{2a}$, $G_{2b}$, or $G_3$ (Zymed, San Francisco, Calif.) (diluted 1:1000 in PBST with 1% normal goat serum) was added. Plates were incubated as above, washed 4× with PBST and 100 μl substrate, was added. The color reaction was quenched after 5 minutes with addition of 50 μl 15% $H_2SO_4$, and absorbance at 490 nm determined on a plate reader (Dynatech).

Results indicated that antibodies 103A, 103B, and 103F were all $IgG_1$ isotype. These antibodies were subsequently used in immunocytochemical analyses, Western blotting, and for purification of protein expressed in baculovirus.

EXAMPLE 7

Baculovirus Expression of Rat ICAM-4

A baculovirus expression system (Invitrogen) was used to generate soluble protein corresponding to domains 1 through 6 of ICAM-4. Because the leader sequence for ICAM-4 was not known at the time, the expression construct was made containing the coding sequence for ICAM-4 fused 3' to the ICAM-1 leader sequence in proper reading frame. Specific details regarding construction of the ICAM-1/ICAM-4 expression plasmid is as follows.

Rat ICAM-1 DNA encoding the five Ig-like domains was amplified by PCR using primers which incorporated several features to facilitate construction of the fusion plasmid. The 5' oligonucleotide primer included HindIII and BglII sites, in addition to a consensus Kozak sequence upstream of the first methionine in the leader sequence. The 3' oligonucleotide primer included a coding sequence for six histidines followed by a stop codon and a HindIII cloning site. The PCR amplification product was cloned into a HindIII-digested pBS⁺ vector and sequence analysis confirmed the appropriate construction. An internal SmaI site in the ICAM-1 leader sequence and another SmaI site in the vector's multiple cloning region (3' to ICAM-1 Ig-like domain 5) were digested which removed most of the ICAM-1 coding sequence. After these manipulations, the linearized, blunt-ended vector contained a portion of the upstream multiple cloning region (those restriction sites 5' of the original HindIII site in the multiple cloning region), the Kozak sequence and most of the ICAM-1 leader sequence.

The coding sequence for rat ICAM-4 domains 1 through 6 was amplified by PCR utilizing primers designed to permit cloning of this sequence into the linearized vector described above. The 5' oligonucleotide primer included an EcoRV site and the codons needed to complete the ICAM-1 leader sequence. The 3' oligonucleotide primer included codons for six histidine residues, a stop codon, and HindIII and EcoRV restriction sites. The amplification product from this PCR was digested with EcoRV to produce a blunt-ended sequence which was then ligated into the blunt-ended SmaI-digested pBS⁺ linearized vector. The entire sequence containing the ICAM-1 leader sequence 5' to the ICAM-4 domains 1 through 6 was removed from the construct with BglII and HindIII digestion and the purified ICAM-1/ICAM-4 fusion sequence cloned directly into a BglII/HindIII-digested pBluesac III vector (Invitrogen).

Protein production by the recombinant virus was assayed for by ELISA, initially using immune sera from mice immunized with rat ICAM-4 domain-2/GST fusion protein described in Example 5. In later work, monoclonal antibodies generated from those mice were used to purify ICAM-4 protein produced by the recombinant baculovirus in SF9 cells.

EXAMPLE 8

Production of Monoclonal Antibodies Against Baculovirus-expressed Rat ICAM-4

Rat ICAM-4 domains 1–6 were expressed in the baculovirus expression system as described in Example 7. The recombinant protein was purified using monoclonal antibody 103A (as described in Example 6).

Briefly, 30 mg of purified monoclonal 103A (in 100 mM sodium borate, 500 mM sodium chloride) were coupled to three grams of Activated Cyanogen Bromide Sepharose 4B (Pharmacia, Piscataway, N.J.). Baculovirus supernatant containing recombinant rat ICAM-4 (domains 1–6) was loaded on the Sepharose column overnight at 4° C. The column was washed in calcium-magnesium-free phosphate buffered saline (CMF-PBS) and bound material was eluted in 50 mM citric acid, 500 mM NaCl pH 4.0. The sample was neutralized with 1/10 volume Tris pH 10 and stored at −20° C. The purified protein separated on SDS-PAGE appeared greater than 90% pure and migrated at approximately 80 kD.

Mice were immunized with the purified recombinant rat ICAM-4 domains 1–6 protein in a similar manner as described in Example 6. The spleen from mouse #1945 was used for fusion #127. The fusion protocol was as described in Example 6. The fusion wells were screened by ELISA on the recombinant ICAM-4 protein. The secondary screen included immunocytochemistry on rat brain sections (as below described in Example 9). Four additional antibodies specific for rat ICAM-4 were cloned out of this fusion: 127A, 127E, 127F and 127H. The immunocytochemical staining pattern of each antibody on rat brain sections was the same as observed with monoclonal antibody 103A (see Example 9). The monoclonal antibodies were tested for their ability to bind the D1/GST and D2/GST fusion proteins (described in Example 5). Monoclonal antibody 127A recognized the D1/GST fusion protein and 127H recognized the D2/GST fusion protein. These two distinct binding specificities along with the others that did not bind either GST protein suggest that at least 3 different epitopes were being recognized by the panel of antibodies. Hybridomas 127A and 127H were deposited May 31, 1995 and Jun. 1, 1995, respectively, with the American Type Culture Collection, 12301 Parklawn Drive, Rockville, Md. 20852, and assigned Accession Numbers HB11905 and HB11911, respectively.

EXAMPLE 9

Imunocytochemistry of Rat ICAM-4 Expression

Immunocytochemistry with monoclonal antibody 103A was performed to localize the protein production within the rat brain.

A brain was harvested from a normal adult female Lewis rat, sagittally sectioned, and washed in RNase-free 1× PBS on ice for 30 min. The brain sections were then placed in Tissue Tek II cryomolds (Miles Laboratories, Inc., Naperville, Ill.) with a small amount of O.C.T. compound (Miles, Inc., Elkhart, Ind.). The brains were centered in the cryomold, the cryomold filled with OCT compound, then placed in a container with 2-methylbutane (Aldrich Chemical Company, Inc., Milwaukee, Wis.) and the container placed in liquid nitrogen. Once the tissue and OCT compound in the cryomold were frozen, the blocks were stored at −80° C. until sectioning.

The tissue was sectioned at 6 μm thickness, adhered to Vectabond (Vector Laboratories, Inc., Burlingame, Calif.) coated slides and allowed to air-dry at room temperature overnight until use. The sections were fixed in ethyl ether (Malinckrodt, Paris, Ky.) for 5 minutes at room temperature. Once the slides were removed from the ether, the reagent was allowed to evaporate. Each tissue section was blocked with 150 μl 50% Normal rat serum (Sigma) and 2% bovine serum albumin (BSA) (Sigma) in 1× PBS (made with sodium phosphates only) for 30 minutes at room temperature. After blocking, the solution was gently blotted from the sections and the purified supernatant antibody 103A (1.65 mg/ml) was diluted 1:10 in the blocking solution and 150 μl applied to each tissue section. The slides were placed in a humidity chamber and incubated at 4° C. overnight.

The next day the antibody solution was blotted gently from the section and the slides washed three times in 1× PBS for four minutes in each wash. The excess PBS was aspirated from the slide and 100 μl of the secondary, rat anti mouse-biotin conjugated antibody (Jackson Immuno-Research Laboratories), diluted 1:100 in a solution of 10% normal rat serum and 2% BSA in 1× PBS, applied to the tissues. Incubation was allowed to proceed for one hour at room temperature. The sections were washed two times in 1× PBS for four minutes in each wash, then 100 μl of ABC reagent from an Elite Rat IgG Vectastain ABC kit (Vector Laboratories, Inc., Burlingame, Calif.), prepared according to the product insert, was applied to each section. Incubation was allowed to proceed for 30 minutes at room temperature. After incubation, the slides were washed two times in 1× PBS (four minutes each wash) and 150 μl of Vector VIP Peroxidase Substrate Solution (Vector Laboratories, Inc., Burlingame, Calif.) applied to each section for approximately ten minutes. After color development, the sections were rinsed under running tap water for five minutes, counterstained with Mayer's hematoxylin (Sigma) for 20 seconds, and rinsed again in gently running tap water for five minutes. The slides were dehydrated across a graded series of ethanols, passed through xylene and mounted with Accumount 60 (Stephens Scientific, Riverdale, N.J.).

Immunohistochemistry of rat brain sections strained with mAb 103A indicated that rat ICAM-4 is expressed in the neuronal cells of the hippocampus. Staining pattern suggested that the protein might be limited to the neuronal processes (dendrites). Brain sections stained in a similar manner with an irrelevant antibody or second step reagent alone do not show the distinct expression pattern seen with MAb 103A.

EXAMPLE 10

Cloning of a Human ICAM-4 Genomic DNA

During the cloning of rat ICAM-4 from genomic DNA, it was discovered that ICAM-4 and ICAM-1 were located within 5 kb of each other and this information was utilized in an attempt to clone the human homologue of ICAM-4.

Genome Systems Inc. (St. Louis, Mo.) amplified fragments in a human P1 library by PCR using human ICAM-1 domain 3 primers, a sense primer designed complementary to human ICAM-1 domain 3 (H-1/D3 S) and an antisense primer designed complementary to human ICAM-1 domain 3 (H-1/D3 AS). These primers are set forth in SEQ ID NOs: 22 and 23, respectively.

CCGGGTCCTAGAGGTGGACACGCA (SEQ ID NO: 22)

TGCAGTGTCTCCTGGCTCTGGTTC (SEQ ID NO: 23)

Two clones, designated 1566 and 1567, were identified and subjected to further analysis. Both P1 clones contained approximately 75–95 kb genomic DNA inserts. The clones were digested with BamH1, separated with agarose gel electrophoresis, and blotted onto nylon membranes. Southern blots hybridization were performed under either low stringency (30% formamide) or high stringency (60% formamide) at 42° C. with human ICAM-1, ICAM-3 or rat ICAM-4 radiolabeled probes; other constituents of the hybridization solution were as described in Example 1. The low stringency hybridization series was washed at room temperature in 2× SSPE containing 0.1% SDS. The high stringency hybridization was washed at 65° C. in 0.2× SSPE containing 0.1% SDS. The washed membranes were exposed to X-ray film for 3.5 hours.

The differential hybridization indicated that human ICAM-1 was contained on a 5.5 kb BamH1 fragment while human ICAM-3 was located on a 4.0 kb and a 1.5 kb BamH1 fragment. The human ICAM-1 and ICAM-R fragments were subcloned into pBS+ and their identity confirmed by limited sequence analysis.

A 7.0 kb BamH1 fragment that hybridized with rat ICAM-4 under high stringency conditions was subcloned and further fragmented with RsaI restriction digestion. Three RsaI fragments that hybridized with rat ICAM-4 were identified and their sequences determined. Based on homology to rat ICAM-4, these fragments appeared to contain domains 2, 3, 4, 5 and part of domain 6.

EXAMPLE 11

Cloning of a Human ICAM-4 cDNA

The fragments of genomic DNA corresponding to domains 2–5 of human ICAM-4 (described in Example 10) were used as probes to screen a λgt10 Human hippocampus cDNA library (Clontech, Palo Alto, Calif.). The library screening protocol was essentially as described in Example 1.

The longest human ICAM-4 clone (#18) that was found in that library was only 992 bp (SEQ ID: 24) and corresponded to roughly the middle of the predicted 3 kb gene. The 992 bp DNA insert from clone 18 (SEQ ID: 24) was used as a probe to screen a λZAPII human hippocampus cDNA library (Stratagene, La Jolla, Calif.). This library yielded a number of positive clones. The longest clone, #34, was 2775 bp (SEQ ID: 25). Based on alignments to the full length rat ICAM-4, it was predicted that this clone was missing the leader sequence and approximately 30 bp at the 5' end of domain 1. The poly A$^+$ tail at the 3' end was missing, but the translation stop codon was present.

A fragment of DNA corresponding to the first 3 domains (nucleotides 1 to 840 in clone #34) was used as a probe to screen a λgt10 cDNA library derived from human cerebral cortex (Clontech, Palo Alto, Calif.). One clone, 16-1 (SEQ ID: 26), was identified as having 1557 bp, and included 39 bp of 5' untranslated DNA, a leader sequence and sequence information through the fifth domain. Overlapping clones #34 (SEQ ID: 25) and 16-1 (SEQ ID: 26) were used to generate a composite of the full length human ICAM-4 sequence (SEQ ID: 27).

The full length gene is 2927 bp long and encodes a 924 amino acid protein. The ICAM-4 nucleotide sequence is set out in SEQ ID NO: 27 and the amino acid sequence is set out in SEQ ID NO: 28. Sequence alignment with the full length rat ICAM-4 gene (SEQ ID: 11) revealed an overall DNA sequence identity of 82% and 85% identity at the amino acid level. The apparent 9 Ig like extracellular domain structure of the protein is conserved between rat and human. The leader sequence extends from amino acid 1 to 28; domain 1 from amino acid 29 to 117; domain 2 from amino acid 118 to 224; domain 3 from amino acid 225 to 320; domain 4 from amino acid 321 to 405; domain 5 from amino acid 406 to 488; domain 6 from amino acid 489 to 570; domain 7 from amino acid 571 to 663; domain 8 from amino acid 664 to 743; domain 9 from amino acid 744 to 837; the transmembrane region from amino acid 838 to 857 and the cytoplasmic tail from amino acid 858 to 924.

Human ICAM-4 (HuICAM-4), in addition to being genetically linked to ICAM-1 and ICAM-R, also showed certain common structural features that group them together as a family of molecules. A domain by domain alignment of HuICAM-4 with the other members of the ICAM family shows varying degrees of homology. Domain 1 amino acid sequence of HuICAM-4 is 21, 30 and 26% identical to domain 1 of ICAMs 1, 2 and 3 respectively. Domain 2 of HuICAM-4 is 61, 39 and 62% identical to ICAMs 1, 2 and 3 respectively. Domain 3 of HuICAM-4 is 50 and 65% identical to ICAMs 1 and 3 respectively. Domain 4 of HuICAM-4 is 54 and 64% identical to ICAMs 1 and 3 respectively. Domains 5-8 of HuICAM-4 are most homologous to the fifth domains of ICAM-1 and 3, with percent identities ranging from 33-47 for ICAM-1 domain 5 and 21-31 for ICAM-R domain 5. The ninth domain of HuICAM-4 aligns poorly with the other members of the ICAM family but is homologous to domains 3 (24% identical) and 6 (23% identical) of HuICAM-1.

EXAMPLE 12

Northern Analysis of Human ICAM-4 Expression

Two human multiple tissue Northern (MTN) blots were purchased from Clontech (Palo Alto, Calif.). These contained at least 2 µg of poly $A^+$ RNA from 16 different human tissues (as shown in Table 1) run on a denaturing formaldehyde 1.2% agarose gel and transferred to nylon membrane. The blots were prehybridized for three hours at 42° C. in 10 ml of a solution containing 5× SSPE, 10× Denhardts solution, 50% formamide, 2% SDS and 100 µg/ml denatured salmon sperm DNA. The blots were hybridized in the above solution with a radiolabeled human ICAM-4 probe (clone #18, SEQ ID: 24) for 16 hours at 42° C. The following day, the blots were washed in a solution of 0.1× SSC/0.1% SDS at room temperature followed by a wash at 50° C. The blots were exposed to x-ray film at −80° C. for 24 hours. Results of the analysis are shown below in Table 1.

Only the lane containing RNA from the brain hybridized to the ICAM-4 probe, giving a single band at approximately 3 kb. Longer exposure (five days) confirmed that only the brain had a detectable level of message. In order to determine if all lanes contained comparable amounts of RNA of comparable quality, the same blot was hybridized with a control β-actin probe. Blots were stripped of the ICAM-4 probe by treatment with a boiling solution of 0.1% SDS for 15 minutes, and subsequently probed in a similar manner with a β actin probe provided by the manufacturer. Except for minor variation in amounts, all lanes were shown to have good quality RNA.

TABLE 1

Northern Tissue Analysis of Human ICAM-4 Expression

| | PROBE | |
|---|---|---|
| Tissue | ICAM-4 | β-Actin |
| Heart | − | +++ |
| Brain | + | ++ |
| Placenta | − | +++ |
| Lung | − | +++ |
| Liver | − | +++ |
| Skeletal muscle | − | ++++ |
| Kidney | − | +++ |
| Pancreas | − | ++ |
| Spleen | − | +++ |
| Thymus | − | +++ |
| Prostate | − | +++ |
| Testis | − | +++ |
| Ovary | − | +++ |
| Small intestine | − | +++ |
| Colon | − | +++ |
| Peripheral blood leukocyte | − | +++ |

Two additional Northern blots were purchased from Clontech that contained poly $A^+$ RNA from 16 different subregions of human brain (as shown in Table 2). Blots were probed in a manner similar to that used for tissue analysis and results are shown in Table 2. RNA quality and quantity loaded was checked by probing the blots with β actin probe.

All of the regions that showed ICAM-4 expression are part of the telencephalon, with the exception of the thalamus which is considered part of the diencephalon. The hippocampus and cerebral cortex appeared to have the highest level of expression. The transcript size in all cases was the same, 3 kb. The exquisite tissue distribution of the ICAM-4 expression suggests that the promoter region may contain elements that confer the observed developmental and spatial expression of the gene product. The utility of such information may provide insight into the understanding of control of neural gene expression in general.

TABLE 2

Northern Brain Cell Type Analysis of Human ICAM-4 Expression

| | PROBE | |
|---|---|---|
| Brain Region | ICAM-4 | β-Actin |
| Amygdala | ++ | +++ |
| Caudate nucleus | ++ | +++ |
| Corpus callosum | + | +++ |
| Hippocampus | ++ | +++ |
| Hypothalamus | − | +++ |
| Substantia nigra | − | +++ |
| Subthalamic nucleus | + | +++ |
| Thalamus | + | +++ |
| Cerebellum | − | +++ |
| Cerebral cortex | +++ | +++ |
| Medulla | − | +++ |
| Spinal cord | − | +++ |
| Occipital pole | ++ | +++ |
| Frontal lobe | ++ | +++ |
| Temporal lobe | ++ | +++ |
| Putamen | ++ | +++ |

EXAMPLE 13

Generation of Human ICAM-4/IgG Fusion Proteins

Human ICAM-4/IgG1 fusion proteins expression plasmids were constructed to produce proteins for generating monoclonal antibodies and for use in adhesion assays to identify potential ICAM-4 ligands. Two constructs were made; the first included DNA encoding domains 1–3 of HuICAM-4 and the second, domains 4–8. Both were linked to the Fc region of human IgG1 in vector pDCS1 that uses the cytomegalovirus (CMV) promoter to drive expression and the signal sequence from IgG4 to facilitate secretion of the molecules.

PCR primers (shown below as SEQ ID NOs: 29–32) were designed to generate the necessary DNA fragments for sub-cloning. The "sense" primer for the 5' end of domain 1 (HI4-D1(s), SEQ ID NO: 29) was designed to fill in 30 base pairs of domain 1 missing in clone #34. Primers HI4-D1(S) (SEQ ID NO: 29) and HI4-D3(AS) (SEQ ID NO: 30) were used to generate a DNA fragment encoding domains 1–3 of human ICAM-4, corresponding to a region in SEQ ID NO: 1 from nucleotide 130 to nucleotide 996. Primers HI4-D3(S) (SEQ ID NO: 31) and HI4-D8(AS) (SEQ ID NO: 32) were used to generate a DNA fragment encoding domains 4–8 of human ICAM-4, corresponding to a region in SEQ ID NO: 30 from nucleotide 997 to nucleotide 2268. Each 5' primer encoded a BamHI restriction site (GGATCC, indicated in bold below) and each 3' (antisense) primer contained a XhoI site (CTCGAG, indicated in bold below) to facilitate sub-cloning 5' to the IgG1 gene. All oligonucleotides contain spacer nucleotides (underlined, below) at the 5' end to permit restriction digestion.

| HI4-D1(S) | (SEQ ID NO: 29) |
|---|---|
| GTACTTACAGGATCCGCGGTCTCGCAG- | |
| GAGCCCTTCTGGGCGGACCTACAGCCTGCGTGGCGTTC | |
| HI4-D3(AS) | (SEQ ID NO: 30) |
| ATTTCTCTCGAGGATGGTCACGTTCTCCCGG | |
| HI4-D4(S) | (SEQ ID NO: 31) |
| ATTTCTGGATCCTACAGCTTCCCGGCACCACTC | |
| HI4-D8(AS) | (SEQ ID NO: 32) |
| ATTTCTCTCGAGTTCCACGCCCACAGTGACGG | |

PCR reactions were carried out in a 50 µl volume using buffers supplied by Perkin Elmer with the AmpliTaq enzyme. Primers were added at a final concentration of 10 µg/ml and all four dNTPs were included at 2 mM. The reactions were continued through 30 cycles of denaturation (94° C. for four minutes), annealing (50° C. for two minutes) and extension (72° C. for one minute). PCR products were visualized on agarose gels and an aliquot of each reaction was used to subclone the PCR products into vector pCRII (Invitrogen, SanDiego, Calif.). Sequence analysis was performed to detect possible errors resulting from the amplification process and to confirm proper orientation. Appropriate clones were digested with BamHI and XhoI and fragments separated with agarose gel electrophoresis. Purified fragments were ligated into a pDCS1 vector previously digested with BamHI and XhoI and the resulting plasmids were sequenced to confirm proper orientation and reading frame.

Human ICAM-4 domains 1–3 and 4–8/IgG1 fusion proteins were obtained following transient transfection of the expression plasmids into COS7 cells and isolation of the secreted protein from the culture media. Transfection was carried out as follows. Adherent COS7 cells at approximately 50–60% confluence were washed with CMF-PBS and subsequently contacted with 10–15 µg of plasmid DNA in 7.5 ml serum-free DMEM media (Gibco, Gaithersburg, Md.) containing 6 µl of 0.25M chloroquine (Sigma, St. Louis, Mo.). An additional 7.5 ml of serum-free media containing 150 µl of DEAE dextran (50 mg/ml) (Sigma, St. Louis, Mo.) were added and the plates incubated 2–3 hours before the media was removed and replaced with 10% DMSO (Mallinckrodt, McGaw Park, Ill.) in PBS. After a one minute incubation, the DMSO solution was removed and replaced with fresh media containing 5% FBS. Each transfection included multiple plates, and media from cells expressing the same protein were pooled for protein isolation.

Media were collected every three days over the course of 3–4 harvests. Proteins were purified using a 0.4–0.8 ml Procep A column (Bioprocessing Ltd, England) pre-equilibrated with 35 mM Tris, 150 mM NaCl, pH 7.5. Culture media was loaded onto the column two times at a flow rate of less than 60 column volumes per hour. The column was washed one time with each of 20 column volumes of Tris/NaCl buffer, 20 column volumes of 0.55M diethanolamine, pH 8.5, and 20 column volumes of 50 mM citric acid, pH 5.0. The fusion proteins were eluted into one ml fractions using 50 mM citric acid pH 3.0 and each fraction was neutralized with 1/10 volume 1M Tris, pH 9.5. Protein concentration was determined by $OD_{280}$, and purity was determined using SDS-PAGE.

A significant contamination from bovine IgG (present in the FBS) was noted. Even though the domains 1–3 fusion protein was predicted to be smaller than the domains 4–8 fusion protein, both migrated at approximately 90 kD. One possible explanation for the observation is that the smaller domains 1–3 fusion protein may be more heavily glycosylated than the larger domains 4–8 fusion protein.

In addition to use of the purified proteins for monoclonal antibody production, described below, the proteins will also be used in adhesion assays to identify ICAM-4 ligands.

EXAMPLE 14

Monoclonal Antibody Production

The purified protein described in Example 13 was utilized to generate monoclonal antibodies using an immunization protocol as described in Example 6.

The spleen from mouse #2250 (immunized with HuICAM-4 D1-3/IgG1) was used for fusion 172 and the spleen from mouse #2272 (immunized with HuICAM-4 D4-8/IgG1) was used for fusion 173. The fusion protocol utilized was as described in Example 6. Fusion plates were screened by ELISA (essentially as described in Example 6) using each HuICAM-4/IgG1 fusion protein. Fusion well supernatants that recognized the immunogen protein, and no other, were considered for cloning. Immunocytochemistry on human hippocampus sections was used as a secondary screen.

One primary clone from each fusion was positive by immunocytochemistry and was cloned. One of the two clones failed to grow upon cloning, leaving only one candidate to pursue, clone 173E which was derived from the HuICAM-4 D4-8/IgG1 immunized mouse. Hybridoma 173E was deposited Jun. 1, 1995 with the American Type Culture Collection, 12301 Parklawn Drive, Rockville, Md. 20852, and assigned Accession Number HB11912.

From another fusion derived from a mouse immunized with a soluble ICAM-4 fragment corresponding to domains 1–3, six clones (179A, 179B, 179D, 179H, 179I, and 179K) were found to be specific for HuICAM4 domains 1 through 3 (D1-3). All six antibodies in the 179 series bound to the dendritic processes in the dentate gyrus, as well as the polymorphic and pyramidal cell layers. The monoclonal antibody 179A stained neuronal cell bodies from these areas in addition to the dendritic processes. The hybridoma cell lines producing antibodies 179I and 179H were deposited on Jun. 6, 1996 with the American Type Culture Collection, 12301 Parklawn Drive, Rockville Md., 20852 and assigned Accession Numbers HB-12123 and HB-12124, respectively.

Additional fusions are similarly performed to generate other antibodies specifically immunoreactive with particular ICAM-4 regions.

EXAMPLE 15
Capture Assay Development

The six monoclonal antibodies from fusion 179 were tested in various combinations for their ability to capture and detect soluble ICAM-4 in solution. The assay, as described below, was established in order to evaluate soluble ICAM-4 levels in human fluids in relation to normal and disease conditions.

Antibody 179I was coated on Immulon 4 (Dynatech) 96 well plates at 3 µg/ml, 125 µl/well for two hours at 37° C. The antibody solution was removed by aspiration and the wells were blocked for 30 minutes at room temperature with 300 µl of blocking solution containing 5% Teleostean gelatin in calcium-free, magnesium-free PBS (CMF-PBS). The blocking solution was removed by aspiration, a 100 µl of sample fluid diluted in Omni Diluent (CMF-PBS, 1% gelatin, and 0.05% Tween 20) was added to each well, and the mixture incubated at 37° C. for 30 minutes. The plates were washed three times with PBST (CMF-PBS, 0.05% Tween 20). Antibody 179H was biotinylated at 1.5 mg/ml using NHS-LC-Biotin (Pierce) following suggested manufacturer's protocol, diluted 1:2000, and added to the wells (100 µl/well). The resulting mixture was incubated for 30 minutes at 37° C. and the plates washed three times with PBST. Streptavidin-HRP (Pierce) was added (100 µl, 0.25 µg/ml) to each well and this mixture incubated at 37° C. for 30 minutes. The plates were washed four times with PBST before addition of 100 µl of Tetramethylbenzidine (Sigma) (10 mg/ml stock in DMSO) diluted 1:100 in buffered substrate (13.6 g/L sodium acetate trihydrate, pH to 5.5 with 1M citric acid, with 150 µl/L 30% hydrogen peroxide added just prior to developing). The reaction was allowed to develop for 30 minutes at room temperature in the dark, after which the reaction was stopped with addition of 50 µl/well 15% $H_2SO_4$. The absorbance was read at 450 nm.

Results indicated that the assay was capable of detecting soluble HuICAM-4 D1-3 recombinant protein at a concentration as low as 5–10 ng/ml with the linear portion of the curve being in the 10–100 ng/ml range. No cross-reactivity to HuICAM4 D4-8 was observed when this protein region was tested at 1 and 10 µg/mL.

EXAMPLE 16
Assessment of Soluble ICAM-4 in Serum from Stroke Patients

In order to assess the role of ICAM-4 in neurologic diseases and conditions, serum from twenty-eight patients suffering from acute stroke and twenty young healthy volunteers (not age matched) was assayed as described above for differences in serum concentration of soluble ICAM-4.

Results indicated that serum from the healthy volunteers had no detectable level of ICAM-4. Twenty out of twenty-eight acute stroke patients, however, had detectable levels of soluble ICAM-4. The signal from the positive stroke patients corresponded to a range of 5–38 ng/ml of the standard (soluble ICAM-4 D1-3 recombinant protein).

EXAMPLE 17
ICAM-4 mRNA Levels in Hippocampus in a Rat Model of Epilepsy

Levels of rat ICAM-4 mRNA expressed were assessed in hippocampus of rats treated in a manner to create a kindling epileptogenesis animal model [Lothman, et al., Brain Res. 360:83–91 (1985)]. In the model, the rat hippocampus is stimulated with a series of subconvulsive electric shocks through an electrode implanted in the region of the brain which gradually elicits severe behavioral seizures. The kindling process involves twelve stimulations per day administered every other day for eight days. Once fully kindled, a single stimulus can elicit behavioral seizures and histologic changes that are similar to human epilepsy. Fully kindled rats received two stimulations per day over a two week period and animals were sacrificed 24 hours after the last stimulation. The hippocampus was removed and dissected for RNA preparation.

Total RNA was prepared from each sample using the guanidinium/phenol/chloroform extraction procedure [Chomezynski and Sacchi, Anal. Biochem. 162:156–159 (1987)]. RNA was separated on denaturing formaldehyde agarose gels, transferred to nylon membranes, and hybridized with radiolabelled rat ICAM-4 and glyceraldehyde-3-phosphate dehydrogenase (GAPDH) specific DNA probes. GAPDH is a basally expressed gene that is commonly used as a control to detect lane to lane variation in the amount of RNA loaded on a gel. Fluctuations in the ratio of the ICAM-4/GAPDH are interpreted as changes in the level of ICAM-4 expression. Hybridizing bands for ICAM-4 and GAPDH were quantitated with a phosphorimager and a ratio of ICAM-4/GAPDH determined.

The ratio of ICAM-4/GAPDH was significantly higher in the control animals that were not kindled (n=5) compared to the kindled test group (n=5), suggesting that ICAM-4 was down regulated as a consequence of the kindling process. It should be noted, however, that the control group did not undergo any sham treatment so the possibility exists that ICAM-4 mRNA levels were modulated in response to the surgical treatment associated with kindling.

EXAMPLE 18
Cloning and Analysis of Human ICAM-4 Upstream Regulatory DNA

ICAM-4 gene expression is spatially and temporally regulated, with expression limited to the most anterior or ventral region of the brain, the telencephalon. In an attempt to identify gene sequences responsible for the restricted transcriptional regulation of ICAM-4, the nucleotide region 5' to human ICAM-4 coding sequences was examined.

A 2607 base pair BamHI/PstI fragment derived from a 7.0 kb genomic BamHI fragment (described in Example 10) was sequenced and found to contain 1684 nucleotides upstream of the ATG start codon. The complete sequence for this upstream region is set out in SEQ ID NO: 33. With respect to the position of the ICAM-4 coding region, the "A" in ATG start codon (numbered in SEQ ID NO: 33 as nucleotides 1685–1687) is designated the +1 nucleotide and the nucleotide immediately 5' to the $A^{+1}$ nucleotide is designated −1. Thus the entire sequence is shown as extending from nucleotide −1684 to nucleotide +3, corresponding to numbering in the Sequence Listing nucleotide 1 to nucleotide 1687.

Based on the genomic HuICAM-4 sequence, oligonucleotides were synthesized and used in PCR to generate DNA molecules of various lengths within the upstream regulatory region. Each oligonucleotide set out in Table 3 contained a spacer region (shown in italics) approximately 6–10 bp to allow enzymatic digestion of the PCR product, an NheI or HindIII restriction site (shown in bold), and a specific hybridization primer sequence (underlined). The oligonucleotide names contain numbers that designate its location within the upstream regulatory region. In the PCR amplifications, oligonucleotides were paired as shown in Table 4 to generate DNA fragments containing specific regions of the upstream regulatory region.

TABLE 3

PCR Primers Used to Amplify HuICAM-4 Upstream Regions

| | |
|---|---|
| HI4-19 (AS) | CAGAACTAAGCTTACAGGAGGCGAGGAGAGCGCGAG (SEQ ID NO: 34) |
| HI4-114 | CAACAATGCTAGCCAAGCGCAACTCTGTCTC (SEQ ID NO: 35) |
| HI4-149 | CAACAATGCTAGCCTTGGAAACCAAGTTACC (SEQ ID NO: 36) |
| HI4-206 | CAACAATGCTAGCAGGAGCTTAGCGCACGCTCG (SEQ ID NO: 37) |
| HI4-270 | CAACAATGCTAGCCATGCCGGCCTCCACGTAG (SEQ ID NO: 38) |
| HI4-408 | CAACAATGCTAGCCGTCCAGCTTATTATCATG (SEQ ID NO: 39) |
| HI4-480 | CAACAATGCTAGCCTTAGTCCCCAAAATGTATC (SEQ ID NO: 40) |
| HI4-560 | CAACAATGCTAGCGGAGAAGGATCAGTGAG (SEQ ID NO: 41) |
| HI4-817 | CAACAATGCTAGCCTCCACCCACCGAGCAGAAG (SEQ ID NO: 42) |

The restriction sites and spacer region generated within each oligonucleotide allowed for enzymatic digestion and subsequent directional cloning of individual PCR products into the pGL3 Basic Vector (Promega, Madison, Wis.) which contains a luciferase reporter gene immediately downstream of a multiple cloning site (MCS). Promoter activity cloned into the MCS region of the vector drives expression of the luciferase reporter gene in transfected cell lines, and light production from expressed luciferase can be measured as an indicator of promoter activity. The pGL3 Basic Vector has no promoter and therefore served as the negative control, while a pGL3 vector containing an SV40 promoter served as a positive control. The sequence of each expression construct was verified by restriction analysis and DNA sequencing.

Plasmids containing each of the amplified sequences described in Table 4 were transfected into mammalian cells using a Transfection MBS Mammalian Transfection Kit (Stratagene, La Jolla, Calif.) according to manufacturer's suggested protocol. Each plasmid was introduced into two different cell lines, COS 7 and NT2 Precursor Cells (Ntera2/D1 from Stratagene). COS 7 cells are a commonly used simian fibroblast-like cell line transformed with SV40 making them well suited for driving expression of a gene under control of the SV40 promoter in cells transfected with the positive control pGL3 Promoter Vector. NT2 precursor cells are a committed neuronal precursor cell line, and while they do not express ICAM-4, they may be more representative of a cell type that does express ICAM-4.

TABLE 4

Primers Paired and Regions Amplified

| Oligonucleotide Pairs | Corresponding Upstream Regulatory Region |
|---|---|
| HI4-19 (AS) with HI4-114 | −19 → −114 |
| HI4-19 (AS) with HI4-149 | −19 → −149 |
| HI4-19 (AS) with HI4-206 | −19 → −206 |

TABLE 4-continued

Primers Paired and Regions Amplified

| Oligonucleotide Pairs | Corresponding Upstream Regulatory Region |
|---|---|
| HI4-19 (AS) with HI4-270 | −19 → −270 |
| HI4-19 (AS) with HI4-408 | −19 → −408 |
| HI4-19 (AS) with HI4-480 | −19 → −480 |
| HI4-19 (AS) with HI4-560 | −19 → −560 |
| HI4-19 (AS) with HI4-817 | −19 → −817 |

Each well of a 6 well flat bottom tissue culture plate (Falcon) was seeded with $2.5 \times 10^5$ cells. Transfections of COS 7 and NT2 cells were done side by side in duplicate using 5 µg of plasmid DNA for each well. The cells were cultured at 37° C. for 48 hours, lysed and assayed for luciferase activity with a Luciferase Assay System (Promega).

Results of the experiment, summarized in Table 5, indicate a high level of promoter activity contained within the −408 through −19 and −480 through −19 regions of the upstream regulatory region of ICAM-4 in NT2 cells. Because NT2 cells are of neuronal origin, they may express certain transcription factors recognizing the ICAM-4 promoter that are not found in other cell types. The highest level of promoter activity in COS cell transfectants was obtained with the plasmid containing nucleotides −560 through −19. While the positive control pGL3 Promoter Vector worked well in COS cells, it showed very low promoter activity in NT2 cells, thus illustrating a cell type specific preference for certain promoter sequences.

TABLE 5

Promoter Activity of 5' ICAM-4 Regions

| | Luminescence | |
|---|---|---|
| Upstream Region | COS | NT2 |
| −114 through −19 | 0.003 | 0.376 |
| −149 through −19 | 0.008 | 0.628 |
| −206 through −19 | 0.443 | 0.622 |
| −270 through −19 | 0.056 | 1.140 |
| −408 through −19 | 0.401 | 7.970 |
| −480 through −19 | 0.274 | 4.630 |
| −560 through −19 | 3.227 | 1.232 |
| −817 through −19 | 0.035 | 4.453 |
| pGL3 Promoter Vector | 29.070 | 0.063 |
| pGL3 Basic Vector | 0.008 | 0.014 |

Since neither COS 7 or NT2 cells normally express ICAM-4, the same experiment will be repeated using primary cultured rat hippocampal neurons which do express ICAM-4 and necessarily express transcriptional machinery required for ICAM-4 promoter activity. By transfecting the individual promoter constructs described herein, as well as others, into the more natural environment, it may be possible to identify more precisely which nucleotides in the upstream regulatory region are responsible for tight regulation of the ICAM-4 gene in the brain.

The foregoing illustrative examples relate to presently preferred embodiments of the invention and numerous modifications and variations thereof will be expected to occur to those skilled in the art. Thus only such limitations as appear in the appended claims should be placed upon the scope of the present invention.

What is claimed is:

1. A purified and isolated DNA comprising a promoter of a mammalian ICAM-4 gene, wherein said promoter is characterized by the ability to specifically promote transcription in a neuronal cell of a polynucleotide operatively linked to said promoter, and said promoter comprises a nucleotide sequence which is 5' to the coding sequence of a mammalian ICAM-4 gene, wherein ICAM-4 is characterized as a neuron-specific cellular adhesion molecule.

2. The DNA according to claim 1 wherein said promoter is from the human ICAM-4 gene.

3. The DNA of claim 2 wherein the promoter is comprised within SEQ ID NO: 33.

4. The DNA according to claim 3 wherein said promoter is comprised within a sequence from about nucleotide 1204 to about nucleotide 1666 in SEQ ID NO: 33.

5. The DNA according to any one of claims 1–4 wherein said neuronal cell is a hippocampal cell.

6. A purified and isolated polynucleotide comprising 1) a promoter of a human ICAM-4 gene, wherein ICAM-4 is characterized as a neuron-specific cellular adhesion molecule, wherein said promoter is characterized by the ability to specifically promote transcription in a neuronal cell of a polynucleotide operatively linked to said promoter, and said promoter comprises a nucleotide sequence which is 5' to the coding sequence of human ICAM-4; and 2) a second nucleotide sequence encoding a heterologous gene which is operatively linked to said promoter.

7. The polynucleotide according to claim 6 wherein said promoter is comprised within a sequence from about nucleotide 1204 to about nucleotide 1666 in SEQ ID NO: 33.

8. An expression vector comprising the DNA according to claim 1 or 6.

9. A host cell transformed with the vector according to claim 8.

* * * * *

UNITED STATES PATENT AND TRADEMARK OFFICE
CERTIFICATE OF CORRECTION

PATENT NO. : 5,753,502
DATED : May 19, 1998
INVENTOR(S) : Kilgannon et al.

It is certified that error appears in the above-identified patent and that said Letters Patent is hereby corrected as shown below:

Title page, item [56], col. 2, line 27, delete "fir" and insert --for--.

Col. 14, line 18: Please delete "residue s", and insert - -residues- -.

Col. 18, line 48: Please delete "Imunocytochemistry", and insert - -Immunocytochemistry--.

Signed and Sealed this

Fourteenth Day of November, 2000

Attest:

Q. TODD DICKINSON

*Attesting Officer*  *Director of Patents and Trademarks*

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 2988 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 61..2814

( x i ) SEQUENCE DESCRIPTION: SEQ ID NO:1:

```
AATTCGATCA CTCGCGCTCC CCTCGCCTTC TGCGCTCTCC CCTCCCTGGC AGCGGCGGCA        60

ATG CCG GGG CCT TCA CCA GGG CTG CGC CGA ACG CTC CTC GGC CTC TGG        108
Met Pro Gly Pro Ser Pro Gly Leu Arg Arg Thr Leu Leu Gly Leu Trp
 1               5                  10                  15

GCT GCC CTG GGC CTG GGG ATC CTA GGC ATC TCA GCG GTC GCG CTA GAA        156
Ala Ala Leu Gly Leu Gly Ile Leu Gly Ile Ser Ala Val Ala Leu Glu
             20                  25                  30

CCT TTC TGG GCG GAC CTT CAG CCC CGC GTG GCG CTC GTG GAG CGC GGG        204
Pro Phe Trp Ala Asp Leu Gln Pro Arg Val Ala Leu Val Glu Arg Gly
         35                  40                  45

GGC TCG CTG TGG CTC AAC TGC AGC ACT AAC TGT CCG AGG CCG GAG CGC        252
Gly Ser Leu Trp Leu Asn Cys Ser Thr Asn Cys Pro Arg Pro Glu Arg
 50                  55                  60

GGT GGC CTG GAG ACC TCG CTA CGC CGA AAC GGG ACC CAG AGG GGT CTG        300
Gly Gly Leu Glu Thr Ser Leu Arg Arg Asn Gly Thr Gln Arg Gly Leu
 65                  70                  75                  80

CGC TGG CTG GCT CGA CAG CTG GTG GAC ATC CGA GAG CCT GAA ACC CAG        348
Arg Trp Leu Ala Arg Gln Leu Val Asp Ile Arg Glu Pro Glu Thr Gln
                 85                  90                  95

CCG GTC TGC TTC TTC CGC TGC GCG CGC CGC ACA CTC CAA GCG CGT GGG        396
Pro Val Cys Phe Phe Arg Cys Ala Arg Arg Thr Leu Gln Ala Arg Gly
             100                 105                 110

CTC ATC CGA ACT TTC CAG CGA CCG GAT CGG GTA GAG CTA GTG CCT CTG        444
Leu Ile Arg Thr Phe Gln Arg Pro Asp Arg Val Glu Leu Val Pro Leu
         115                 120                 125

CCT CCT TGG CAG CCT GTA GGT GAG AAC TTC ACC TTG AGC TGC AGG GTC        492
Pro Pro Trp Gln Pro Val Gly Glu Asn Phe Thr Leu Ser Cys Arg Val
 130                 135                 140

CCG GGG GCA GGA CCC CGA GCG AGC CTC ACA TTG ACC TTG CTG CGA GGC        540
Pro Gly Ala Gly Pro Arg Ala Ser Leu Thr Leu Thr Leu Leu Arg Gly
 145                 150                 155                 160

GGC CAG GAG CTG ATT CGC CGA AGT TTC GTA GGC GAG CCA CCC CGA GCT        588
Gly Gln Glu Leu Ile Arg Arg Ser Phe Val Gly Glu Pro Pro Arg Ala
                 165                 170                 175

CGG GGT GCG ATG CTC ACC GCC ACG GTC CTG GCG CGC AGA GAG GAT CAC        636
Arg Gly Ala Met Leu Thr Ala Thr Val Leu Ala Arg Arg Glu Asp His
             180                 185                 190

AGG GCC AAT TTC TCA TGC CTC GCG GAG CTT GAC CTG CGG CCA CAC GGC        684
Arg Ala Asn Phe Ser Cys Leu Ala Glu Leu Asp Leu Arg Pro His Gly
         195                 200                 205

TTG GGA CTG TTT GCA AAC AGC TCA GCC CCC AGA CAG CTC CGC ACG TTT        732
Leu Gly Leu Phe Ala Asn Ser Ser Ala Pro Arg Gln Leu Arg Thr Phe
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     |     |     | 210 |     |     |     |     | 215 |     |     |     |     | 220 |     |
| GCC | ATG | CCT | CCA | CTT | TCC | CCG | AGC | CTT | ATT | GCC | CCA | CGA | TTC | TTA | GAA | 780 |
| Ala | Met | Pro | Pro | Leu | Ser | Pro | Ser | Leu | Ile | Ala | Pro | Arg | Phe | Leu | Glu |
| 225 |     |     |     |     | 230 |     |     |     |     | 235 |     |     |     |     | 240 |
| GTG | GGC | TCA | GAA | AGG | CCG | GTG | ACT | TGC | ACT | TTG | GAT | GGA | CTG | TTT | CCT | 828 |
| Val | Gly | Ser | Glu | Arg | Pro | Val | Thr | Cys | Thr | Leu | Asp | Gly | Leu | Phe | Pro |
|     |     |     |     | 245 |     |     |     |     | 250 |     |     |     |     | 255 |     |
| GCC | CCA | GAA | GCC | GGG | GTT | TAC | CTC | TCT | CTG | GGA | GAT | CAG | AGG | CTT | CAT | 876 |
| Ala | Pro | Glu | Ala | Gly | Val | Tyr | Leu | Ser | Leu | Gly | Asp | Gln | Arg | Leu | His |
|     |     |     |     | 260 |     |     |     |     | 265 |     |     |     |     | 270 |     |
| CCT | AAT | GTG | ACC | CTC | GAC | GGG | GAG | AGC | CTT | GTG | GCC | ACT | GCC | ACA | GCT | 924 |
| Pro | Asn | Val | Thr | Leu | Asp | Gly | Glu | Ser | Leu | Val | Ala | Thr | Ala | Thr | Ala |
|     |     |     | 275 |     |     |     |     | 280 |     |     |     |     | 285 |     |     |
| ACA | GCA | AGT | GAA | GAA | CAG | GAA | GGC | ACC | AAA | CAG | CTG | ATG | TGC | ATC | GTG | 972 |
| Thr | Ala | Ser | Glu | Glu | Gln | Glu | Gly | Thr | Lys | Gln | Leu | Met | Cys | Ile | Val |
|     | 290 |     |     |     |     | 295 |     |     |     |     | 300 |     |     |     |     |
| ACC | CTC | GGG | GGC | GAA | AGC | AGG | GAG | ACC | CAG | GAA | AAC | CTG | ACT | GTC | TAC | 1020 |
| Thr | Leu | Gly | Gly | Glu | Ser | Arg | Glu | Thr | Gln | Glu | Asn | Leu | Thr | Val | Tyr |
| 305 |     |     |     |     | 310 |     |     |     |     | 315 |     |     |     |     | 320 |
| AGC | TTC | CCG | GCT | CCT | CTT | CTG | ACT | TTA | AGT | GAG | CCA | GAA | GCC | CCC | GAG | 1068 |
| Ser | Phe | Pro | Ala | Pro | Leu | Leu | Thr | Leu | Ser | Glu | Pro | Glu | Ala | Pro | Glu |
|     |     |     |     | 325 |     |     |     |     | 330 |     |     |     |     | 335 |     |
| GGA | AAG | ATG | GTG | ACC | GTA | AGC | TGC | TGG | GCA | GGG | GCC | CGA | GCC | CTT | GTC | 1116 |
| Gly | Lys | Met | Val | Thr | Val | Ser | Cys | Trp | Ala | Gly | Ala | Arg | Ala | Leu | Val |
|     |     |     | 340 |     |     |     |     | 345 |     |     |     |     | 350 |     |     |
| ACC | TTG | GAG | GGA | ATT | CCA | GCT | GCG | GTC | CCT | GGG | CAG | CCC | GCT | GAG | CTC | 1164 |
| Thr | Leu | Glu | Gly | Ile | Pro | Ala | Ala | Val | Pro | Gly | Gln | Pro | Ala | Glu | Leu |
|     |     | 355 |     |     |     |     | 360 |     |     |     |     | 365 |     |     |     |
| CAG | TTA | AAT | GTC | ACA | AAG | AAT | GAC | GAC | AAG | CGG | GGC | TTC | TTC | TGC | GAC | 1212 |
| Gln | Leu | Asn | Val | Thr | Lys | Asn | Asp | Asp | Lys | Arg | Gly | Phe | Phe | Cys | Asp |
|     | 370 |     |     |     |     | 375 |     |     |     |     | 380 |     |     |     |     |
| GCT | GCC | CTC | GAT | GTG | GAC | GGG | GAA | ACT | CTG | AGA | AAG | AAC | CAG | AGC | TCT | 1260 |
| Ala | Ala | Leu | Asp | Val | Asp | Gly | Glu | Thr | Leu | Arg | Lys | Asn | Gln | Ser | Ser |
| 385 |     |     |     |     | 390 |     |     |     |     | 395 |     |     |     |     | 400 |
| GAG | CTT | CGT | GTT | CTG | TAC | GCA | CCT | CGG | CTG | GAT | GAC | TTG | GAC | TGT | CCC | 1308 |
| Glu | Leu | Arg | Val | Leu | Tyr | Ala | Pro | Arg | Leu | Asp | Asp | Leu | Asp | Cys | Pro |
|     |     |     |     | 405 |     |     |     |     | 410 |     |     |     |     | 415 |     |
| AGG | AGC | TGG | ACG | TGG | CCA | GAG | GGT | CCA | GAG | CAG | ACC | CTC | CAC | TGC | GAG | 1356 |
| Arg | Ser | Trp | Thr | Trp | Pro | Glu | Gly | Pro | Glu | Gln | Thr | Leu | His | Cys | Glu |
|     |     |     | 420 |     |     |     |     | 425 |     |     |     |     | 430 |     |     |
| GCC | CGT | GGA | AAC | CCT | GAG | CCC | TCC | GTG | CAC | TGT | GCA | AGG | CCT | GAC | GGT | 1404 |
| Ala | Arg | Gly | Asn | Pro | Glu | Pro | Ser | Val | His | Cys | Ala | Arg | Pro | Asp | Gly |
|     |     | 435 |     |     |     |     | 440 |     |     |     |     | 445 |     |     |     |
| GGG | GCG | GTG | CTA | GCG | CTG | GGC | CTG | TTG | GGT | CCA | GTG | ACC | CGT | GCC | CTC | 1452 |
| Gly | Ala | Val | Leu | Ala | Leu | Gly | Leu | Leu | Gly | Pro | Val | Thr | Arg | Ala | Leu |
|     | 450 |     |     |     |     | 455 |     |     |     |     | 460 |     |     |     |     |
| GCG | GGC | ACT | TAC | CGA | TGT | ACA | GCA | ATC | AAT | GGG | CAA | GGC | CAG | GCG | GTC | 1500 |
| Ala | Gly | Thr | Tyr | Arg | Cys | Thr | Ala | Ile | Asn | Gly | Gln | Gly | Gln | Ala | Val |
| 465 |     |     |     |     | 470 |     |     |     |     | 475 |     |     |     |     | 480 |
| AAG | GAT | GTG | ACC | CTG | ACT | GTG | GAA | TAT | GCC | CCA | GCG | CTG | GAC | AGT | GTA | 1548 |
| Lys | Asp | Val | Thr | Leu | Thr | Val | Glu | Tyr | Ala | Pro | Ala | Leu | Asp | Ser | Val |
|     |     |     |     | 485 |     |     |     |     | 490 |     |     |     |     | 495 |     |
| GGC | TGC | CCA | GAA | CGT | ATT | ACT | TGG | CTG | GAG | GGG | ACA | GAG | GCA | TCG | CTT | 1596 |
| Gly | Cys | Pro | Glu | Arg | Ile | Thr | Trp | Leu | Glu | Gly | Thr | Glu | Ala | Ser | Leu |
|     |     |     | 500 |     |     |     |     | 505 |     |     |     |     | 510 |     |     |
| AGC | TGT | GTG | GCA | CAC | GGG | GTC | CCA | CCA | CCT | AGC | GTG | AGC | TGT | GTG | CGC | 1644 |
| Ser | Cys | Val | Ala | His | Gly | Val | Pro | Pro | Pro | Ser | Val | Ser | Cys | Val | Arg |
|     |     | 515 |     |     |     |     | 520 |     |     |     |     | 525 |     |     |     |
| TCT | GGA | AAG | GAG | GAA | GTC | ATG | GAA | GGG | CCC | CTG | CGT | GTG | GCC | CGG | GAG | 1692 |
| Ser | Gly | Lys | Glu | Glu | Val | Met | Glu | Gly | Pro | Leu | Arg | Val | Ala | Arg | Glu |

```
              530                        535                        540
CAC GCT GGC ACT TAC CGA TGC GAA GCC ATC AAC GCC AGG GGA TCA GCG    1740
His Ala Gly Thr Tyr Arg Cys Glu Ala Ile Asn Ala Arg Gly Ser Ala
545                     550                     555                560

GCC AAA AAT GTG GCT GTC ACG GTG GAA TAT GGT CCC AGT TTT GAG GAG    1788
Ala Lys Asn Val Ala Val Thr Val Glu Tyr Gly Pro Ser Phe Glu Glu
                    565                     570                575

TTG GGC TGC CCC AGC AAC TGG ACT TGG GTA GAA GGA TCT GGA AAA CTG    1836
Leu Gly Cys Pro Ser Asn Trp Thr Trp Val Glu Gly Ser Gly Lys Leu
                580                     585                590

TTT TCC TGT GAA GTT GAT GGG AAG CCG GAA CCA CGC GTG GAG TGC GTG    1884
Phe Ser Cys Glu Val Asp Gly Lys Pro Glu Pro Arg Val Glu Cys Val
            595                     600                 605

GGC TCG GAG GGT GCA AGC GAA GGG GTA GTG TTG CCC CTG GTG TCC TCG    1932
Gly Ser Glu Gly Ala Ser Glu Gly Val Val Leu Pro Leu Val Ser Ser
        610                     615                 620

AAC TCT GGT TCC AGA AAC TCT ATG ACT CCT GGT AAC CTG TCA CCG GGT    1980
Asn Ser Gly Ser Arg Asn Ser Met Thr Pro Gly Asn Leu Ser Pro Gly
625                     630                     635                640

ATT TAC CTC TGC AAC GCC ACC AAC CGG CAT GGC TCC ACA GTC AAA ACA    2028
Ile Tyr Leu Cys Asn Ala Thr Asn Arg His Gly Ser Thr Val Lys Thr
                    645                     650                655

GTC GTC GTG AGC GCG GAA TCA CCG CCA CAG ATG GAT GAA TCC AGT TGC    2076
Val Val Val Ser Ala Glu Ser Pro Pro Gln Met Asp Glu Ser Ser Cys
                660                     665                 670

CCG AGT CAC CAG ACA TGG CTG GAA GGA GCC GAG GCT ACT GCG CTG GCC    2124
Pro Ser His Gln Thr Trp Leu Glu Gly Ala Glu Ala Thr Ala Leu Ala
            675                     680                 685

TGC AGT GCC AGA GGC CGC CCC TCT CCA CGC GTG CGC TGT TCC AGG GAA    2172
Cys Ser Ala Arg Gly Arg Pro Ser Pro Arg Val Arg Cys Ser Arg Glu
690                     695                     700

GGT GCA GCC AGG CTG GAG AGG CTA CAG GTG TCC CGA GAG GAT GCG GGG    2220
Gly Ala Ala Arg Leu Glu Arg Leu Gln Val Ser Arg Glu Asp Ala Gly
705                     710                     715                720

ACC TAC CTG TGT GTG GCT ACC AAC GCG CAT GGC ACG GAT TCA CGG ACC    2268
Thr Tyr Leu Cys Val Ala Thr Asn Ala His Gly Thr Asp Ser Arg Thr
                    725                     730                735

GTC ACT GTG GGT GTG GAA TAC CGG CCT GTG GTG GCT GAG CTG GCA GCC    2316
Val Thr Val Gly Val Glu Tyr Arg Pro Val Val Ala Glu Leu Ala Ala
                740                     745                 750

TCG CCC CCA AGC GTG CGG CCT GGC GGA AAC TTC ACT CTG ACC TGC CGT    2364
Ser Pro Pro Ser Val Arg Pro Gly Gly Asn Phe Thr Leu Thr Cys Arg
            755                     760                 765

GCA GAG GCC TGG CCT CCA GCC CAG ATC AGC TGG CGC GCG CCC CCG GGA    2412
Ala Glu Ala Trp Pro Pro Ala Gln Ile Ser Trp Arg Ala Pro Pro Gly
770                     775                     780

GCT CTC AAC CTC GGT CTC TCC AGC AAC AAC AGC ACG CTG AGC GTG GCG    2460
Ala Leu Asn Leu Gly Leu Ser Ser Asn Asn Ser Thr Leu Ser Val Ala
785                     790                     795                800

GGT GCC ATG GGC AGC CAT GGT GGC GAG TAT GAG TGC GCA GCC ACC AAT    2508
Gly Ala Met Gly Ser His Gly Gly Glu Tyr Glu Cys Ala Ala Thr Asn
                    805                     810                815

GCG CAT GGG CGC CAC GCA CGG CGC ATC ACG GTG CGC GTG GCC GGT CCA    2556
Ala His Gly Arg His Ala Arg Arg Ile Thr Val Arg Val Ala Gly Pro
                820                     825                 830

TGG CTG TGG GTC GCT GTG GGC GGT GCG GCA GGG GGC GCG GCG CTG CTG    2604
Trp Leu Trp Val Ala Val Gly Gly Ala Ala Gly Gly Ala Ala Leu Leu
            835                     840                 845

GCC GCA GGG GCC GGC CTG GCC TTC TAC GTG CAG TCC ACC GCT TGC AAG    2652
Ala Ala Gly Ala Gly Leu Ala Phe Tyr Val Gln Ser Thr Ala Cys Lys
```

|  | 850 |  |  |  | 855 |  |  |  | 860 |  |  |  |  |  |
|---|---|---|---|---|---|---|---|---|---|---|---|---|---|---|
| AAG | GGA | GAG | TAC | AAC | GTC | CAG | GAG | GCT | GAG | AGC | TCA | GGC | GAG | GCG | GTG | 2700 |
| Lys | Gly | Glu | Tyr | Asn | Val | Gln | Glu | Ala | Glu | Ser | Ser | Gly | Glu | Ala | Val |
| 865 | | | | 870 | | | | 875 | | | | | | 880 |

```
AAG GGA GAG TAC AAC GTC CAG GAG GCT GAG AGC TCA GGC GAG GCG GTG     2700
Lys Gly Glu Tyr Asn Val Gln Glu Ala Glu Ser Ser Gly Glu Ala Val
865               870                 875                 880

TGT CTC AAT GGC GCG GGC GGG ACA CCG GGT GCA GAA GGC GGA GCA GAG     2748
Cys Leu Asn Gly Ala Gly Gly Thr Pro Gly Ala Glu Gly Gly Ala Glu
                885                 890                 895

ACC CCC GGC ACT GCC GAG TCA CCT GCA GAT GGC GAG GTT TTC GCC ATC     2796
Thr Pro Gly Thr Ala Glu Ser Pro Ala Asp Gly Glu Val Phe Ala Ile
            900                 905                 910

CAG CTG ACA TCT TCC TGAGCCTGTA TCCAGCTCCC CAGGGGCCT CGAAAGCACA      2851
Gln Leu Thr Ser Ser
            915

GGGGTGGACG TATGTATTGT TCACTCTCTA TTTATTCAAC TCCAGGGGCG TCGTCCCCGT   2911

TTTCTACCCA TTCCCTTAAT AAAGTTTTA TAGGAGAAAA AAAAAAAAAA AAAAAAAAA    2971

AAAAAAAAAA AAAAAA                                                   2988
```

( 2 ) INFORMATION FOR SEQ ID NO:2:

( i ) SEQUENCE CHARACTERISTICS:
       ( A ) LENGTH: 917 amino acids
       ( B ) TYPE: amino acid
       ( D ) TOPOLOGY: linear ( i i ) MOLECULE TYPE: protein ( x i ) SEQUENCE DESCRIPTION: SEQ ID NO:2:

```
Met Pro Gly Pro Ser Pro Gly Leu Arg Arg Thr Leu Leu Gly Leu Trp
 1               5                  10                 15

Ala Ala Leu Gly Leu Gly Ile Leu Gly Ile Ser Ala Val Ala Leu Glu
            20                  25                  30

Pro Phe Trp Ala Asp Leu Gln Pro Arg Val Ala Leu Val Glu Arg Gly
        35                  40                  45

Gly Ser Leu Trp Leu Asn Cys Ser Thr Asn Cys Pro Arg Pro Glu Arg
    50                  55                  60

Gly Gly Leu Glu Thr Ser Leu Arg Arg Asn Gly Thr Gln Arg Gly Leu
65                  70                  75                  80

Arg Trp Leu Ala Arg Gln Leu Val Asp Ile Arg Glu Pro Glu Thr Gln
                85                  90                  95

Pro Val Cys Phe Phe Arg Cys Ala Arg Arg Thr Leu Gln Ala Arg Gly
            100                 105                 110

Leu Ile Arg Thr Phe Gln Arg Pro Asp Arg Val Glu Leu Val Pro Leu
        115                 120                 125

Pro Pro Trp Gln Pro Val Gly Glu Asn Phe Thr Leu Ser Cys Arg Val
    130                 135                 140

Pro Gly Ala Gly Pro Arg Ala Ser Leu Thr Leu Thr Leu Leu Arg Gly
145                 150                 155                 160

Gly Gln Glu Leu Ile Arg Arg Ser Phe Val Gly Glu Pro Pro Arg Ala
                165                 170                 175

Arg Gly Ala Met Leu Thr Ala Thr Val Leu Ala Arg Arg Glu Asp His
            180                 185                 190

Arg Ala Asn Phe Ser Cys Leu Ala Glu Leu Asp Leu Arg Pro His Gly
        195                 200                 205

Leu Gly Leu Phe Ala Asn Ser Ser Ala Pro Arg Gln Leu Arg Thr Phe
    210                 215                 220

Ala Met Pro Pro Leu Ser Pro Ser Leu Ile Ala Pro Arg Phe Leu Glu
225                 230                 235                 240
```

```
Val Gly Ser Glu Arg Pro Val Thr Cys Thr Leu Asp Gly Leu Phe Pro
                245             250             255

Ala Pro Glu Ala Gly Val Tyr Leu Ser Leu Gly Asp Gln Arg Leu His
            260             265             270

Pro Asn Val Thr Leu Asp Gly Glu Ser Leu Val Ala Thr Ala Thr Ala
            275             280             285

Thr Ala Ser Glu Glu Gln Glu Gly Thr Lys Gln Leu Met Cys Ile Val
    290             295             300

Thr Leu Gly Gly Glu Ser Arg Glu Thr Gln Glu Asn Leu Thr Val Tyr
305             310             315                 320

Ser Phe Pro Ala Pro Leu Leu Thr Leu Ser Glu Pro Glu Ala Pro Glu
                325             330             335

Gly Lys Met Val Thr Val Ser Cys Trp Ala Gly Ala Arg Ala Leu Val
            340             345             350

Thr Leu Glu Gly Ile Pro Ala Ala Val Pro Gly Gln Pro Ala Glu Leu
            355             360             365

Gln Leu Asn Val Thr Lys Asn Asp Lys Arg Gly Phe Phe Cys Asp
    370             375             380

Ala Ala Leu Asp Val Asp Gly Glu Thr Leu Arg Lys Asn Gln Ser Ser
385             390             395                 400

Glu Leu Arg Val Leu Tyr Ala Pro Arg Leu Asp Asp Leu Asp Cys Pro
                405             410             415

Arg Ser Trp Thr Trp Pro Glu Gly Pro Glu Gln Thr Leu His Cys Glu
            420             425             430

Ala Arg Gly Asn Pro Glu Pro Ser Val His Cys Ala Arg Pro Asp Gly
            435             440             445

Gly Ala Val Leu Ala Leu Gly Leu Leu Gly Pro Val Thr Arg Ala Leu
    450             455             460

Ala Gly Thr Tyr Arg Cys Thr Ala Ile Asn Gly Gln Gly Gln Ala Val
465             470             475                 480

Lys Asp Val Thr Leu Thr Val Glu Tyr Ala Pro Ala Leu Asp Ser Val
            485             490             495

Gly Cys Pro Glu Arg Ile Thr Trp Leu Glu Gly Thr Glu Ala Ser Leu
            500             505             510

Ser Cys Val Ala His Gly Val Pro Pro Ser Val Ser Cys Val Arg
    515             520             525

Ser Gly Lys Glu Glu Val Met Glu Gly Pro Leu Arg Val Ala Arg Glu
530             535             540

His Ala Gly Thr Tyr Arg Cys Glu Ala Ile Asn Ala Arg Gly Ser Ala
545             550             555                 560

Ala Lys Asn Val Ala Val Thr Val Glu Tyr Gly Pro Ser Phe Glu Glu
            565             570             575

Leu Gly Cys Pro Ser Asn Trp Thr Trp Val Glu Gly Ser Gly Lys Leu
            580             585             590

Phe Ser Cys Glu Val Asp Gly Lys Pro Glu Pro Arg Val Glu Cys Val
            595             600             605

Gly Ser Glu Gly Ala Ser Glu Gly Val Val Leu Pro Leu Val Ser Ser
    610             615             620

Asn Ser Gly Ser Arg Asn Ser Met Thr Pro Gly Asn Leu Ser Pro Gly
625             630             635                 640

Ile Tyr Leu Cys Asn Ala Thr Asn Arg His Gly Ser Thr Val Lys Thr
            645             650             655

Val Val Val Ser Ala Glu Ser Pro Pro Gln Met Asp Glu Ser Ser Cys
```

|  | | | | | 660 | | | | 665 | | | | 670 | | |
|---|---|---|---|---|---|---|---|---|---|---|---|---|---|---|---|
| Pro | Ser | His 675 | Gln | Thr | Trp | Leu | Glu 680 | Gly | Ala | Glu | Ala | Thr 685 | Ala | Leu | Ala |
| Cys | Ser 690 | Ala | Arg | Gly | Arg | Pro 695 | Ser | Pro | Arg | Val | Arg 700 | Cys | Ser | Arg | Glu |
| Gly 705 | Ala | Ala | Arg | Leu | Glu 710 | Arg | Leu | Gln | Val | Ser 715 | Arg | Glu | Asp | Ala | Gly 720 |
| Thr | Tyr | Leu | Cys | Val 725 | Ala | Thr | Asn | Ala | His 730 | Gly | Thr | Asp | Ser | Arg 735 | Thr |
| Val | Thr | Val | Gly 740 | Val | Glu | Tyr | Arg | Pro 745 | Val | Val | Ala | Glu | Leu 750 | Ala | Ala |
| Ser | Pro | Pro 755 | Ser | Val | Arg | Pro | Gly 760 | Gly | Asn | Phe | Thr | Leu 765 | Thr | Cys | Arg |
| Ala | Glu 770 | Ala | Trp | Pro | Pro | Ala 775 | Gln | Ile | Ser | Trp | Arg 780 | Ala | Pro | Pro | Gly |
| Ala 785 | Leu | Asn | Leu | Gly | Leu 790 | Ser | Ser | Asn | Ser 795 | Thr | Leu | Ser | Val | Ala 800 | |
| Gly | Ala | Met | Gly | Ser 805 | His | Gly | Gly | Glu | Tyr 810 | Glu | Cys | Ala | Ala | Thr 815 | Asn |
| Ala | His | Gly | Arg 820 | His | Ala | Arg | Arg | Ile 825 | Thr | Val | Arg | Val | Ala 830 | Gly | Pro |
| Trp | Leu | Trp 835 | Val | Ala | Val | Gly | Gly 840 | Ala | Ala | Gly | Gly | Ala 845 | Ala | Leu | Leu |
| Ala | Ala 850 | Gly | Ala | Gly | Leu | Ala 855 | Phe | Tyr | Val | Gln | Ser 860 | Thr | Ala | Cys | Lys |
| Lys 865 | Gly | Glu | Tyr | Asn | Val 870 | Gln | Glu | Ala | Glu | Ser 875 | Ser | Gly | Glu | Ala | Val 880 |
| Cys | Leu | Asn | Gly | Ala 885 | Gly | Gly | Thr | Pro | Gly 890 | Ala | Glu | Gly | Gly | Ala 895 | Glu |
| Thr | Pro | Gly | Thr 900 | Ala | Glu | Ser | Pro | Ala 905 | Asp | Gly | Glu | Val | Phe 910 | Ala | Ile |
| Gln | Leu | Thr 915 | Ser | Ser | | | | | | | | | | | |

( 2 ) INFORMATION FOR SEQ ID NO:3:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..315

( x i ) SEQUENCE DESCRIPTION: SEQ ID NO:3:

| CCG | GAT | CGG | GTA | GAG | CTA | GTG | CCT | CTG | CCT | CCT | TGG | CAG | CCT | GTA | GGT | 48 |
|---|---|---|---|---|---|---|---|---|---|---|---|---|---|---|---|---|
| Pro 1 | Asp | Arg | Val | Glu 5 | Leu | Val | Pro | Leu | Pro 10 | Pro | Trp | Gln | Pro | Val 15 | Gly | |
| GAG | AAC | TTC | ACC | TTG | AGC | TGC | AGG | GTC | CCG | GGG | GCA | GGA | CCC | CGA | GCG | 96 |
| Glu | Asn | Phe | Thr 20 | Leu | Ser | Cys | Arg | Val 25 | Pro | Gly | Ala | Gly | Pro 30 | Arg | Ala | |
| AGC | CTC | ACA | TTG | ACC | TTG | CTG | CGA | GGC | GGA | CAG | GAG | CTG | ATT | CGC | CGA | 144 |
| Ser | Leu | Thr 35 | Leu | Thr | Leu | Leu | Arg 40 | Gly | Gly | Gln | Glu | Leu 45 | Ile | Arg | Arg | |
| AGT | TTC | GTA | GGC | GAG | CCA | CCC | CGA | GCT | CGG | TGT | GCG | ATG | CTC | ACC | GCC | 192 |

```
          Ser  Phe  Val  Gly  Glu  Pro  Pro  Arg  Ala  Arg  Cys  Ala  Met  Leu  Thr  Ala
               50                  55                       60

ACG  GTC  CTG  GCG  CGC  AGA  GAG  GAT  CAC  AGG  GAC  AAT  TTC  TCA  TGC  CTC           240
Thr  Val  Leu  Ala  Arg  Arg  Glu  Asp  His  Arg  Asp  Asn  Phe  Ser  Cys  Leu
65                       70                       75                       80

GCG  GAG  CTT  GAC  CTG  CGG  ACA  CAC  GGC  TTG  GGA  CTG  TTT  GCA  AAC  AGC           288
Ala  Glu  Leu  Asp  Leu  Arg  Thr  His  Gly  Leu  Gly  Leu  Phe  Ala  Asn  Ser
                    85                       90                       95

TCA  GCC  CCC  AGA  CAG  CTC  CGC  ACG  TTT                                              315
Ser  Ala  Pro  Arg  Gln  Leu  Arg  Thr  Phe
               100                      105
```

( 2 ) INFORMATION FOR SEQ ID NO:4:

( i ) SEQUENCE CHARACTERISTICS:
        ( A ) LENGTH: 1781 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 16..1659

( x i ) SEQUENCE DESCRIPTION: SEQ ID NO:4:

```
CAGCTCTCTG  TCAGA  ATG  GCC  ACC  ATG  GTA  CCA  TCC  GTG  TTG  TGG  CCC  AGG           51
                  Met  Ala  Thr  Met  Val  Pro  Ser  Val  Leu  Trp  Pro  Arg
                  1                   5                        10

GCC  TGC  TGG  ACT  CTG  CTG  GTC  TGC  TGT  CTG  CTG  ACC  CCA  GGT  GTC  CAG           99
Ala  Cys  Trp  Thr  Leu  Leu  Val  Cys  Cys  Leu  Leu  Thr  Pro  Gly  Val  Gln
               15                       20                       25

GGG  CAG  GAG  TTC  CTT  TTG  CGG  GTG  GAG  CCC  CAG  AAC  CCT  GTG  CTC  TCT           147
Gly  Gln  Glu  Phe  Leu  Leu  Arg  Val  Glu  Pro  Gln  Asn  Pro  Val  Leu  Ser
          30                       35                       40

GCT  GGA  GGG  TCC  CTG  TTT  GTG  AAC  TGC  AGT  ACT  GAT  TGT  CCC  AGC  TCT           195
Ala  Gly  Gly  Ser  Leu  Phe  Val  Asn  Cys  Ser  Thr  Asp  Cys  Pro  Ser  Ser
45                       50                       55                       60

GAG  AAA  ATC  GCC  TTG  GAG  ACG  TCC  CTA  TCA  AAG  GAG  CTG  GTG  GCC  AGT           243
Glu  Lys  Ile  Ala  Leu  Glu  Thr  Ser  Leu  Ser  Lys  Glu  Leu  Val  Ala  Ser
                    65                       70                       75

GGC  ATG  GGC  TGG  GCA  GCC  TTC  AAT  CTC  AGC  AAC  GTG  ACT  GGC  AAC  AGT           291
Gly  Met  Gly  Trp  Ala  Ala  Phe  Asn  Leu  Ser  Asn  Val  Thr  Gly  Asn  Ser
               80                       85                       90

CGG  ATC  CTC  TGC  TCA  GTG  TAC  TGC  AAT  GGC  TCC  CAG  ATA  ACA  GGC  TCC           339
Arg  Ile  Leu  Cys  Ser  Val  Tyr  Cys  Asn  Gly  Ser  Gln  Ile  Thr  Gly  Ser
          95                       100                      105

TCT  AAC  ATC  ACC  GTG  TAC  GGG  CTC  CCG  GAG  CGT  GTG  GAG  CTG  GCA  CCC           387
Ser  Asn  Ile  Thr  Val  Tyr  Gly  Leu  Pro  Glu  Arg  Val  Glu  Leu  Ala  Pro
     110                      115                      120

CTG  CCT  CCT  TGG  CAG  CCG  GTG  GGC  CAG  AAC  TTC  ACC  CTG  CGC  TGC  CAA           435
Leu  Pro  Pro  Trp  Gln  Pro  Val  Gly  Gln  Asn  Phe  Thr  Leu  Arg  Cys  Gln
125                      130                      135                      140

GTG  GAG  GGT  GGG  TCG  CCC  CGG  ACC  AGC  CTC  ACG  GTG  GTG  CTG  CTT  CGC           483
Val  Glu  Gly  Gly  Ser  Pro  Arg  Thr  Ser  Leu  Thr  Val  Val  Leu  Leu  Arg
               145                      150                      155

TGG  GAG  GAG  GAG  CTG  AGC  CGG  CAG  CCC  GCA  GTG  GAG  GAG  CCA  GCG  GAG           531
Trp  Glu  Glu  Glu  Leu  Ser  Arg  Gln  Pro  Ala  Val  Glu  Glu  Pro  Ala  Glu
          160                      165                      170

GTC  ACT  GCC  ACT  GTG  CTG  GCC  AGC  AGA  GAC  GAC  CAC  GGA  GCC  CCT  TTC           579
Val  Thr  Ala  Thr  Val  Leu  Ala  Ser  Arg  Asp  Asp  His  Gly  Ala  Pro  Phe
          175                      180                      185
```

-continued

| | | | | | | | | | | | | | | | | |
|---|---|---|---|---|---|---|---|---|---|---|---|---|---|---|---|---|
| TCA | TGC | CGC | ACA | GAA | CTG | GAC | ATG | CAG | CCC | CAG | GGG | CTG | GGA | CTG | TTC | 627 |
| Ser | Cys | Arg | Thr | Glu | Leu | Asp | Met | Gln | Pro | Gln | Gly | Leu | Gly | Leu | Phe | |
| | 190 | | | | 195 | | | | | 200 | | | | | | |
| GTG | AAC | ACC | TCA | GCC | CCC | CGC | CAG | CTC | CGA | ACC | TTT | GTC | CTG | CCC | GTG | 675 |
| Val | Asn | Thr | Ser | Ala | Pro | Arg | Gln | Leu | Arg | Thr | Phe | Val | Leu | Pro | Val | |
| 205 | | | | | 210 | | | | | 215 | | | | | 220 | |
| ACC | CCC | CCG | CGC | CTC | GTG | GCC | CCC | CGG | TTC | TTG | GAG | GTG | GAA | ACG | TCG | 723 |
| Thr | Pro | Pro | Arg | Leu | Val | Ala | Pro | Arg | Phe | Leu | Glu | Val | Glu | Thr | Ser | |
| | | | | 225 | | | | | 230 | | | | | 235 | | |
| TGG | CCG | GTG | GAC | TGC | ACC | CTA | GAC | GGG | CTT | TTT | CCA | GCC | TCA | GAG | GCC | 771 |
| Trp | Pro | Val | Asp | Cys | Thr | Leu | Asp | Gly | Leu | Phe | Pro | Ala | Ser | Glu | Ala | |
| | | | 240 | | | | | 245 | | | | | 250 | | | |
| CAG | GTC | TAC | CTG | GCG | CTG | GGG | GAC | CAG | ATG | CTG | AAT | GCG | ACA | GTC | ATG | 819 |
| Gln | Val | Tyr | Leu | Ala | Leu | Gly | Asp | Gln | Met | Leu | Asn | Ala | Thr | Val | Met | |
| | | 255 | | | | | 260 | | | | | 265 | | | | |
| AAC | CAC | GGG | GAC | ACG | CTA | ACG | GCC | ACA | GCC | ACA | GCC | ACG | GCG | CGC | GCG | 867 |
| Asn | His | Gly | Asp | Thr | Leu | Thr | Ala | Thr | Ala | Thr | Ala | Thr | Ala | Arg | Ala | |
| | 270 | | | | | 275 | | | | | 280 | | | | | |
| GAT | CAG | GAG | GGT | GCC | CGG | GAG | ATC | GTC | TGC | AAC | GTG | ACC | CTA | GGG | GGC | 915 |
| Asp | Gln | Glu | Gly | Ala | Arg | Glu | Ile | Val | Cys | Asn | Val | Thr | Leu | Gly | Gly | |
| 285 | | | | | 290 | | | | | 295 | | | | | 300 | |
| GAG | AGA | CGG | GAG | GCC | CGG | GAG | AAC | TTG | ACG | GTC | TTT | AGC | TTC | CTA | GGA | 963 |
| Glu | Arg | Arg | Glu | Ala | Arg | Glu | Asn | Leu | Thr | Val | Phe | Ser | Phe | Leu | Gly | |
| | | | | 305 | | | | | 310 | | | | | 315 | | |
| CCC | ATT | GTG | AAC | CTC | AGC | GAG | CCC | ACC | GCC | CAT | GAG | GGG | TCC | ACA | GTG | 1011 |
| Pro | Ile | Val | Asn | Leu | Ser | Glu | Pro | Thr | Ala | His | Glu | Gly | Ser | Thr | Val | |
| | | | 320 | | | | | 325 | | | | | 330 | | | |
| ACC | GTG | AGT | TGC | ATG | GCT | GGG | GCT | CGA | GTC | CAG | GTC | ACG | CTG | GAC | GGA | 1059 |
| Thr | Val | Ser | Cys | Met | Ala | Gly | Ala | Arg | Val | Gln | Val | Thr | Leu | Asp | Gly | |
| | | 335 | | | | | 340 | | | | | 345 | | | | |
| GTT | CCG | GCC | GCG | GCC | CCG | GGG | CAG | ACA | GCT | CAA | CTT | CAG | CTA | AAT | GCT | 1107 |
| Val | Pro | Ala | Ala | Ala | Pro | Gly | Gln | Thr | Ala | Gln | Leu | Gln | Leu | Asn | Ala | |
| | 350 | | | | | 355 | | | | | 360 | | | | | |
| ACC | GAG | AGT | GAC | GAC | GGA | CGC | AGC | TTC | TTC | TGC | AGT | GCC | ACT | CTC | GAG | 1155 |
| Thr | Glu | Ser | Asp | Asp | Gly | Arg | Ser | Phe | Phe | Cys | Ser | Ala | Thr | Leu | Glu | |
| 365 | | | | | 370 | | | | | 375 | | | | | 380 | |
| GTG | GAC | GGC | GAG | TTC | TTG | CAC | AGG | AAC | AGT | AGC | GTC | CAG | CTG | CGA | GTC | 1203 |
| Val | Asp | Gly | Glu | Phe | Leu | His | Arg | Asn | Ser | Ser | Val | Gln | Leu | Arg | Val | |
| | | | | 385 | | | | | 390 | | | | | 395 | | |
| CTG | TAT | GGT | CCC | AAA | ATT | GAC | CGA | GCC | ACA | TGC | CCC | CAG | CAC | TTG | AAA | 1251 |
| Leu | Tyr | Gly | Pro | Lys | Ile | Asp | Arg | Ala | Thr | Cys | Pro | Gln | His | Leu | Lys | |
| | | | 400 | | | | | 405 | | | | | 410 | | | |
| TGG | AAA | GAT | AAA | ACG | AGA | CAC | GTC | CTG | CAG | TGC | CAA | GCC | AGG | GGC | AAC | 1299 |
| Trp | Lys | Asp | Lys | Thr | Arg | His | Val | Leu | Gln | Cys | Gln | Ala | Arg | Gly | Asn | |
| | | 415 | | | | | 420 | | | | | 425 | | | | |
| CCG | TAC | CCC | GAG | CTG | CGG | TGT | TTG | AAG | GAA | GGC | TCC | AGC | CGG | GAG | GTG | 1347 |
| Pro | Tyr | Pro | Glu | Leu | Arg | Cys | Leu | Lys | Glu | Gly | Ser | Ser | Arg | Glu | Val | |
| | 430 | | | | | 435 | | | | | 440 | | | | | |
| CCG | GTG | GGG | ATC | CCG | TTC | TTC | GTC | AAC | GTA | ACA | CAT | AAT | GGT | ACT | TAT | 1395 |
| Pro | Val | Gly | Ile | Pro | Phe | Phe | Val | Asn | Val | Thr | His | Asn | Gly | Thr | Tyr | |
| 445 | | | | | 450 | | | | | 455 | | | | | 460 | |
| CAG | TGC | CAA | GCG | TCC | AGC | TCA | CGA | GGC | AAA | TAC | ACC | CTG | GTC | GTG | GTG | 1443 |
| Gln | Cys | Gln | Ala | Ser | Ser | Ser | Arg | Gly | Lys | Tyr | Thr | Leu | Val | Val | Val | |
| | | | | 465 | | | | | 470 | | | | | 475 | | |
| ATG | GAC | ATT | GAG | GCT | GGG | AGC | TCC | CAC | TTT | GTC | CCC | GTC | TTC | GTG | GCG | 1491 |
| Met | Asp | Ile | Glu | Ala | Gly | Ser | Ser | His | Phe | Val | Pro | Val | Phe | Val | Ala | |
| | | | 480 | | | | | 485 | | | | | 490 | | | |
| GTG | TTA | CTG | ACC | CTG | GGC | GTG | GTG | ACT | ATC | GTA | CTG | GCC | TTA | ATG | TAC | 1539 |
| Val | Leu | Leu | Thr | Leu | Gly | Val | Val | Thr | Ile | Val | Leu | Ala | Leu | Met | Tyr | |
| | | 495 | | | | | 500 | | | | | 505 | | | | |

| | | | | | | | | | | | | | | | | |
|---|---|---|---|---|---|---|---|---|---|---|---|---|---|---|---|---|
| GTC | TTC | AGG | GAG | CAC | CAA | CGG | AGC | GGC | AGT | TAC | CAT | GTT | AGG | GAG | GAG | 1587 |
| Val | Phe | Arg | Glu | His | Gln | Arg | Ser | Gly | Ser | Tyr | His | Val | Arg | Glu | Glu | |
| | 510 | | | | | 515 | | | | | 520 | | | | | |
| AGC | ACC | TAT | CTG | CCC | CTC | ACG | TCT | ATG | CAG | CCG | ACA | GAA | GCA | ATG | GGG | 1635 |
| Ser | Thr | Tyr | Leu | Pro | Leu | Thr | Ser | Met | Gln | Pro | Thr | Glu | Ala | Met | Gly | |
| 525 | | | | | 530 | | | | | 535 | | | | | 540 | |
| GAA | GAA | CCG | TCC | AGA | GCT | GAG | TGACGCTGGG | | ATCCGGGATC | | AAAGTTGGCG | | | | | 1686 |
| Glu | Glu | Pro | Ser | Arg | Ala | Glu | | | | | | | | | | |
| | | | | 545 | | | | | | | | | | | | |

GGGGCTTGGC TGTGCCCTCA GATTCCGCAC CAATAAAGCC TTCAAACTCC CAAAAAAAA 1746

AAAAAAAAAA AAAAAAAAAA AAAAAAAAAA AAAAA 1781

( 2 ) INFORMATION FOR SEQ ID NO:5:

( i ) SEQUENCE CHARACTERISTICS:
        ( A ) LENGTH: 4900 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

| | | | | | |
|---|---|---|---|---|---|
| CCGAACGCTC | CTCGGCCTCT | GGTCTNCTCT | GGNCCTGGGG | ATCCTAGGCA | TCTCAGGTAA | 60 |
| GAAGAGCCCG | CCCGTGGAGC | NAGGTGGATA | AGGCGGGGGC | GGAATTGAAG | GACCAGAGAG | 120 |
| GGCGGCCCGG | GTGTCCCCCT | CCAGGCTCCG | CCCTCTTCTA | GCTTCCCACG | CTTCTGTCAC | 180 |
| CACCTGGAGN | TCGGGGCTTC | TCCCCGTCCT | TCCTCCACCC | CAACACACCT | CAATCTTTCA | 240 |
| GANCTGAACC | CAGCACCTTT | TCTGGANTNG | GGGNNTTGCA | CCTAACCTGT | CTCAGGAGAN | 300 |
| ACTGTGGCTC | TCCTGTCCTC | TCCTGCTCTG | TNATGCCCTA | TGGTTCACAG | ACTGGCATCA | 360 |
| TCCCTATTCA | TGATCCTCAA | AGACNCCATC | TCCTCAACTG | TCATAACTCA | GAGCTCTATT | 420 |
| CCCCCTCCAC | CTGGAGCCCT | GGAAACCGGC | TTTCTAGGGC | TTTTCTCCGC | GGTTCTTTCC | 480 |
| CGGAGTTCAG | CGTTGTGGCT | TTTTGTCCAA | GTTACTCAAG | TTTGGGGACA | ATCTCCTTTA | 540 |
| AGCCTTTGAC | TCAGTCTCAT | TTCCACTTTG | CTTTTGCCCC | AAGCCTCTGT | GTCTCTCCCC | 600 |
| CATTTCCTGA | CGATCTGTCA | GAGTCTTAAG | AGTGATTTGG | TTCCCCATCC | CCCCTCCAAC | 660 |
| TGGAGTCTCC | TCCTCACTAT | TGATGTGTGC | ATCTGAGACC | CCCATCCCCG | CACCGAGTTT | 720 |
| CCCCATCTCT | GTCAGTAAAG | AGCAAGGCTT | CCAGAGACAA | CCCTCTAATA | GCGCGTCAGT | 780 |
| CCCGAATCTT | GAGTGGGATG | CGGGACTCCC | GTGCTATTTC | TTGGCGGAGG | TCTTTCCTGG | 840 |
| TCCTTATGGA | CACCCCTGGT | TTGGGATATG | GGGGCCGCTA | AGATTTCAGA | GATGGGGTCC | 900 |
| CTAGGCTGAG | NCCGCGTTTT | CCCGGGCAGC | GGTCGCGCTA | GAACCTTTCT | GGGCGGACCT | 960 |
| TCAGCCCCGC | GTGGCGCTCG | TGGAGCGCGG | GGGCTCGCTG | TGGCTCAACT | GCAGCACTAA | 1020 |
| CTGTCCGAGG | CCGGAGCGCG | GTGGCCTGGA | GACCTCGCTA | CGCCGAAACG | GGACCCAGAG | 1080 |
| GGGTCTGNAC | TGNCTGGCTC | GACAGCTGGT | GGACATCCGA | GANCCTGAAA | CCCAGCCGGT | 1140 |
| CTGCTTCTTC | CNCTGCGCGC | GCCGCACACT | CCAAGCGCGT | GGGCTCATCC | GAACTTTCCG | 1200 |
| TGAGTTCAGG | GTGGGCACNC | CCCTTGGGTC | TCTGGACCTC | CCCCTCAAGC | TCCTCCCACC | 1260 |
| CGCCCTCTGA | TCCTCCTGCT | TGTTCTGAAA | GTACTACAGC | TGGCTAGAGC | GGAGTTTTTG | 1320 |
| GTCCCTTGCA | GAGCGACCGG | ATCGGGTAGA | GCTAGTGCCT | CTGCCTCCTT | GGCAGCCTGT | 1380 |
| AGGTGAGAAC | TTCACCTTGA | GCTGCAGGGT | CCCGGGGGCA | GGACCCCGAG | CGAGCCTCAC | 1440 |
| ATTGACCTTG | CTGCGAGGCG | GCCAGGAGCT | GATTCGCCGA | AGTTTCGTAG | GCGAGCCACC | 1500 |
| CCGAGCTCGG | GGTGCGATGC | TCACCGCCAC | GGTCCTGGCG | CGCAGAGAGG | ATCACAGGGC | 1560 |

-continued

```
CAATTTCTCA TGCCTCGCGG AGCTTGACCT GCGNCCACAC GGCTTGGGAC TGTTTGCANA    1620
CAGCTCAGCC CCCAGACAGC TCCGCACGTT TGGTGAGTGT GGACCCTAAC TGACAGATTT    1680
TAAGAAGTTT AGGGCAGCCA GGCGTGGTGG CATGGTGTCG TAGGCCCTAA GTCCCAGCCC    1740
AAGCAGANCT AAGNCGGATC TCTTGTGAAT TAAAAGTCTA GCTCGTCTAC ATAACGAGGN    1800
CTGCATAGTT AAATCCCCCA AAAGTCTAAG CAGCTAGCCC TTACTTCCAA CACAAGTACT    1860
AGCTTAAGTA CTTTCTCCTG TGAGCTTTTT CCTTTATGTA TTTACTCGTT GAGAGAAAAA    1920
GAGAGTGTGT GTACGTGCCT TTATGCACAT GCCGCAGTGC TTGTATGGAA GTTAAAGAAT    1980
AAGGAGGCGT TCTGCCCTTC CATCCTGTGG GTCCTAGGGG TGGTATTAGC TCCTCAGGCT    2040
TTGTTAGTNA CAAGCGCCTA GGCTTGGGGA GCCATCTCGC CCGCTCCTCT GTATCTTTAG    2100
GGTGAAACCA GACAATGCAT GCAAATTGGT TGATCAACAC TGAATGTTTA GTTCGTAAAT    2160
TCAAGCTCTG TTCTTTGTCT TCCTCAGCCA TGCCTCCACT TTCCCCCGAG CCTTATTGCC    2220
CCACGATTCT TAGAAGTGGG CTCAGAAAGG CCGGTGACKT GCACTTTGGA TGGACTGTTT    2280
CCTGCCCCAG AAGCCGGGGT TTACTTCTCT CTGGGAGATC AGAGGCTTCA TCCTAATGTG    2340
ACCCTCGACG GGGAGAGCCT TGTGGCCACT GCCACAGCTA CAGCAAGTGA AGAACAGGAA    2400
GGCACCAAAC AGCTGATGTG CATCGTGACC CTCGGGGGCG AAAGCAGGGA GACCCAGGAA    2460
AACCTGACTG TCTACAGTAA GGGGAATCCA ACAAGACCTT CAATAGCTCA GACTGGGGCT    2520
GGGGCTGGGT CTGGGTCTGG GGCCAGAGTC TCACAAAGGC GGAGCCTATA AAGTGGGCGG    2580
GACCTCCACA CCAGAACAAG CCGGGCGGGA GAGTTCCAGG GCAGGAGCAG ATAGAAGTTG    2640
GAAATTAATA GATTGGGTTG AGTTCCCTGA GTGGGGAGTG AACCCCACCC AATTCTCTGT    2700
CCCCAGGCTT CCCGGCTCCT CTTCTGACTT TAAGTGAGCC AGAAGCCCCC GAGGGAAAGA    2760
TGGTGACCGT AAGCTGCTGG GCAGGGGCCC GAGCCCTTGT CACCTTGGAG GGAATTCCAA    2820
GGACCCTCTT ACCGGCCCCA TCTTTAACCT TATCGTATCC CCTCTGCCTC ATGCCCGCAG    2880
ACGCACCTCG GCTGGATGAC TTGGACTGTC CAGGAGCTG GACGTGGCCA GAGGGTCCAG    2940
AGCAGACCCT CCACTGCGAG GCCCGTGGAA ACCCTGAGCC CTCCGTGCAC TGTGCAAGGC    3000
CTGACGGTGG GGCGGTGCTA GCGCTGGGCC TGTTGGGTCC AGTGACCCGT GCCCTCGCGG    3060
GCACTTACCG ATGTACAGCA ATCAATGGGC AAGGCCAGGC GGTCAAGGAT GTGACCCTGA    3120
CTGTGGAATG TGAGTAGGGG GAGGTGGGCA TGCTTATCCC TTTAAGGTCA CGGAGTGTAC    3180
TGGGAGACTG GCTATACGGA AAGGAAAGAA GCCTAGGTTC AGCAGGGATT GGGAAAACAC    3240
TGAAGGAAAG TGGTGTGGTG TTTACAAACT TAACGGTGGT AACTGGGCAC GGTCTGGCAA    3300
AAACAGACAG CCAAGAGAGT GTGCCTGGGA AGCTGCAATG GGGGCTTTGT GGGAATTGGT    3360
CAACAGCACC CTGAGATCTC AGGAAAGGGG CCTGAAGTTA TCTCCAGAAC CCATGTGAAG    3420
GCAGGAAGAG AGAACGCCCA CCTTTTCCTG CTCCCCCAA CCCCCCCCA CATATCACAC    3480
GGAGTATATA AATAAATAAA ATGGCTCCTG CCGGAGGGAG TGAGAAGCTG TCTCCTGCAG    3540
GCTCAGAGCA GTGGTAGTGC ATGCCTTTAA TCCCAGCACT CGGTAGGCAA AGCAGGCAG    3600
ATCTCTGTGA ATGTGGGGCC AGCCTGGTCT GTACAGAGAA ATCCTGTCTC AAAACAAACC    3660
AGCAAAGAAA CAAAACCAAA ATCAATTCCA GATGCCCCAG CGCTGGACAG TGTAGGCTGC    3720
CCANGACGTA TTACTTGNCT GGAGGGGACA GAGGCATCGC TTAGCTGTGT GGCACACGGG    3780
GTCCCACCAC CTAGCGTGAG CTGTGTGCGC TCTGGAAAGG AGGAAGTCAT GGAAGGGCCC    3840
CTGCGTGTGG CCCGGGAGCA CGCTGGCACT TACCGATGCG AAGCCATCAA CGCCAGGGA    3900
TCAGCGGNCA AAAATGTGGC TGTCACGGTG GAATGTGAGT AGGGGTGGCT ACGGAAATGT    3960
```

```
CCACACCTGC  GTCCTCTGTC  CTCAGTGTGA  ACTCCTATTT  CCCTGCTTCC  TAGATGGTCC    4020
CAGTTNTGAG  GAGTTGGGCT  GCCCCAGCAA  CTGGACTTGG  GTAGAAGGAT  CTGGAAAACT    4080
GTTTCCTGT   GAAGTTGATG  GGAAGCCGGA  ACCACGCGTG  GAGTGCGTGG  GCTCGGAGGG    4140
TGCAAGCGAA  GGGGTAGTGT  TGCCCCTGGT  GTCCTCGAAC  TCTGGTTCCA  GAAACTCTAT    4200
GACTCCTGGT  AACCTGTCAC  CGGGTATTTA  CCTCTGCAAC  GCCACCAACC  GGCATGGCTC    4260
CACAGTCAAA  ACAGTCGTCG  TGAGCGCGGA  ATGTGAGCAG  GGGCCCAGGT  GGGCGGAGAG    4320
TACCGGGTGT  CCCAGGATCT  TTTCTTTCCC  TGATGCCCCT  CCTTATGGTG  GCTGATCTGC    4380
AGCACCGCCA  CAGATGGATG  AATCCAGTTG  CCCGAGTCAC  CAGACATGGC  TGGAAGGAGC    4440
CGAGGCTACT  GCGCTGGCCT  GCAGTGACAG  GGGNCGCCCC  TCTCCACGCG  TGCGCTGTTC    4500
CAGGGAAGGT  GCAGCCAGGC  TGGAGAGGCT  ACAGGTGTCC  CGAGAGGATG  CGGGGACCTA    4560
CCTGTGTGTG  GCTACCAACG  CGCATGGCAC  GGATTCACGG  ACCGTCACTG  TGGGTGTGGA    4620
ATGTGAGTGA  GGACAGCGCT  GAATGAAGAC  GACTCAGACC  GCCAGAAAAG  TGCCTTGAGG    4680
CCTGGGATGT  ATGATCCAGT  GGGTAGAGTG  CTCAATTAGC  ACTCACTAAA  ATGTATATTC    4740
TATTCCTAAT  ACTCTTTAAT  TTTANCCTTT  GGGAGGCAGA  GACAGGCAGA  TCTCTGTTCC    4800
GGGATAACCT  GCTCTCTGTC  TAGGACAGCT  TGGTCTACAG  AGGGGNTACA  GGCCCCCCCT    4860
CCCAAGATTG  NATAGCAACC  CTCTGGCTCC  CTGTCTCTCT                            4900
```

( 2 ) INFORMATION FOR SEQ ID NO:6:

( i ) SEQUENCE CHARACTERISTICS:
        ( A ) LENGTH: 1295 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
NGAATTCCGG  CGGATCGGGT  AGAGCTAGTG  CCTCTGCCTC  CTTGGCAGCC  TGTAGGTGAG      60
AACTTCACCT  TGAGCTGCAG  GGTCCCGGGG  GCAGGACCCC  GAGCGAGCCT  CACATTGACC     120
TTGCTGCGAG  GCGGCCAGGA  GCTGATTCGC  CGAAGTTTCG  TAGGCGAGCC  ACCCCGAGCT     180
CGGGGTGCGA  TGCTCACCGC  CACGGTCCTG  GCGCGCAGAG  AGGATCACAG  GCCAATTTC      240
TCATGCCTCG  CGGAGCTTGA  CCTGCGGCCA  CACGGCTTGG  GACTGTTTGC  AAACAGCTCA     300
GCCCCCAGAC  AGCTCCGCAC  GTTTGCCATG  CCTCCACTTT  CCCCGAGCCT  TATTGCCCCA     360
CGATTCTTAG  AAGTGGGCTC  AGAAAGGCCG  GTGACTTGCA  CTTTGGATGG  ACTGTTTCCT     420
GCCCCAGAAG  CCGGGGTTTA  CCTCTCTCTG  GGAGATCAGA  GGCTTCATCC  TAATGTGACC     480
CTCGACGGGG  AGAGCCTTGT  GGCCACTGCC  ACAGCTACAG  CAAGTGAAGA  ACAGGAAGGC     540
ACCAAACAGC  TGATGTGCAT  CGTGACCCTC  GGGGGCGAAA  GCAGGGAGAC  CCAGGAAAAC     600
CTGACTGTCT  ACAGCTTCCC  GGCTCCTCTT  CTGACTTTAA  GTGAGCCAGA  AGCCCCCGAG     660
GGAAAGATGG  TGACCGTAAG  CTGCTGGGCA  GGGGCCCGAG  CCCTTGTCAC  CTTGGAGGGA     720
ATTCCAAGGA  CCCTCTTACC  GGCCCCATCT  TTAACCTTAT  CGTATCCCCT  CTGCCTCATG     780
CCCGCAGACG  CACCTCGGCT  GGATGACTTG  GACTGTCCCA  GGAGCTGGAC  GTGGCCAGAG     840
GGTCCAGAGC  AGACCCTCCA  CTGCGAGGCC  CGTGGAAACC  CTGAGCCCTC  CGTGCACTGT     900
GCAAGGCCTG  ACGGTGGGGC  GGTGCTAGCG  CTGGGCCTGT  TGGGTCCAGT  GACCCGTGCC     960
CTCGCGGGCA  CTTACCGATG  TACAGCAATC  AATGGGCAAG  GCCAGGCGGT  CAAGGATGTG    1020
```

| | | | | | |
|---|---|---|---|---|---|
| ACCCTGACTG | TGGAATATGC | CCCAGCGCTG | GACAGTGTAG | GCTGCCCAGA | ACGTATTACT | 1080 |
| TGGCTGGAGG | GGACAGAGGC | ATCGCTTAGC | TGTGTGGCAC | ACGGGGTCCC | ACCACCTAGC | 1140 |
| GTGAGCTGTG | TGCGCTCTGG | AAAGGAGGAA | GTCATGGAAG | GGCCCCTGCG | TTTTGGCCGG | 1200 |
| GAGCACGCTG | GCACTTACCG | ATGCGAAGCC | ATCAACGCCA | GGGGATCAGC | GGCCAAAAAT | 1260 |
| GTGGCTGTCA | CGGTGGAATA | TGGTCCCCGG | AATTC | | | 1295 |

( 2 ) INFORMATION FOR SEQ ID NO:7:

( i ) SEQUENCE CHARACTERISTICS:
        ( A ) LENGTH: 2214 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

| | | | | | |
|---|---|---|---|---|---|
| CGAATCTTGA | GTGGGATGCG | GGACTCCCGT | GCTATTTCTT | GGCGGAGGTC | TTTCCTGGTC | 60 |
| CTTATGGACA | CCCCTGGTTT | GGGATATGGG | GGCCGCTAAG | ATTTCAGAGA | TGGGGTCCCT | 120 |
| AGGCTGAGCC | CGCGTTTTCC | CGGGCAGCGG | TCGCGCTAGA | ACCTTTCTGG | GCGGACCTTC | 180 |
| AGCCCCGCGT | GGCGCTCGTG | GAGCGCGGGG | GCTCGCTGTG | GCTCAACTGC | AGCACTAACT | 240 |
| GTCCGAGGCC | GGAGCGCGGT | GGYCTGGAGA | CCTCGCTACG | CCGAAACGGG | ACCCAGAGGG | 300 |
| GTCTGCGCTG | GCTGGCTCGA | CAGMTGGTGG | ACATCCGAGA | GCCTGAAACC | CAGTCGGTCT | 360 |
| GCTTCTTCCG | CTGGGCGCGC | CGCACACTCC | AAGNGAGTGG | GCTCATCCGA | ACTTTCCAGC | 420 |
| GACCGGATCG | GGTAGAGCTA | GTGCCTCTGN | CTCCTTGGCA | GCCTGTAGGT | GAGAACTTCA | 480 |
| CCTTGAGCTG | CAGGGTCCCG | GGGGCAGGAC | CCCGAGCGAG | CCTCACATTG | ACCTTGCTGC | 540 |
| GAGGCGGCCA | GGAGCTGATT | CGCCGAAGTT | TCGTAGGCGA | GCCACCCCGA | GCTCGGGGTG | 600 |
| CGATGCTCAC | CGCCACGGTC | CTGGCGCGCA | GAGAGGATCA | CAGGGCCAAT | TTCTCATGCC | 660 |
| TCGCGGAGCT | TGACCTGCGG | ACACACGGCT | TGGGACTGTT | TGCAAACAGC | TCAGCCCCCA | 720 |
| GACAGCTCCG | CACGTTTGGC | ATGCCTCCAC | TTTCCCCGAG | CCTTATTGNC | CCACGATTCT | 780 |
| TAGAAGTGGG | CTCAGAAAGG | CCGGTGACTT | GCACTTTGGA | TGGACTGTTT | CCTGCCCCAG | 840 |
| AAGCCGGGGT | TTACCTCTCT | CTGGGAGATC | AGAGGCTTCA | TCCTAATGTG | ACCCTCGACG | 900 |
| GGGAGAGCCT | TGTGGCCACT | GNCACAGMTA | CAGCAAGTGA | AGAACAGGAA | GGCACCAAAC | 960 |
| AGCTGATGTG | CATCGTGACC | CTCGGGGGCG | AAAGCAGGGA | GACCCAGGAA | AACCTGACTG | 1020 |
| TCTACAGCTT | CCCGGCTCCT | CTTCTGACTT | TAAGTGAGCC | AGAAGCCCCC | GAGGGAAAGA | 1080 |
| TGGTGACCGT | AAGCTGCTGG | GCAGGGGCCC | GAGCCCTTGT | CACCTTGGAG | GGAATTCCAG | 1140 |
| CTGCGGTCCC | TGGGCAGCCC | GCTGAGCTCC | AGTTAAATGT | CACAAAGAAT | GACGACAAGC | 1200 |
| GGGGCTTCTT | CTGCGACGCT | GCCCTCGATG | TGGACGGGGA | AACTCTGAGA | AAGAACCAGA | 1260 |
| GCTCTGAGCT | TCGTGTTCTG | TACGCACCTC | GGCTGGATGA | CTTGGACTGT | CCCAGGAGCT | 1320 |
| GGACGTGGCC | AGAGGGTCCA | GAGCAGACCC | TCCACTGCGA | GGCCCGTGGA | AACCCTGAGC | 1380 |
| CCTCCGTGCA | CTGTGCAAGG | CCTGACGGTG | GGCGGTGCT | AGCGCTGGGC | CTGTTGGGTC | 1440 |
| CAGTGACCCG | TGCCCTCGCG | GGAACTTACC | GATGTACAGC | AATCAATGGG | CAAGGCCAGG | 1500 |
| CGGTCAAGGA | TGTGACCCTG | ACTGTGGAAT | ATGCCCCAGC | GCTGGACAGT | GTAGGCTGCC | 1560 |
| CAGAACGTAT | TACTTGGCTG | GAGGGGACAG | AGGCATCGCT | TAGCTGTGTG | GCACACGGGG | 1620 |
| TCCCACCACC | TAGCGTGAGC | TGTGTGCGCT | CTGGAAAGGA | GGAAGTCATG | GAAGGGCCCC | 1680 |
| TGCGTGTGGC | CCGGGAGCAC | GCTGGCACTT | ACCGATGCGA | AGCCATCAAC | GNCAGGGGAT | 1740 |

| | | | | | |
|---|---|---|---|---|---|
| CAGCGGWCAA | AAATGTGGCT | GTCACGGTGG | AATATGGTCC | CAGTTTGGAG | GAGTTGGGCT | 1800 |
| GCCCCAGYAA | CTGGACTTGG | GTAGAAGGAT | CTGGAAAACT | GTTTTCCTGT | GAAGTTGATG | 1860 |
| GGAAGCCGGA | ACCACGCGTG | GAGTGCGTGG | GCTCGGAGGG | TGCAAGCGAA | GGGGTAGTGT | 1920 |
| TGCCCCTGGT | GTCCTCGAAC | TCTGGTTCCA | GAAACTCTAT | GACTCCTGGT | AACCTGTCAC | 1980 |
| CGGGTATTTA | CCTCTGCAAC | GCCACCAACC | GGMATGGNTC | CACAGTCAAA | ACAGTCGTCG | 2040 |
| TGAGCGCGGA | ATCACCGCCA | CAGATGGATG | AATCCAGTTG | CCCGAGTCAC | CAGACATGGN | 2100 |
| TGGAAGGAGC | CGAGGNTACT | GCGCTGGCCT | GCAGTGCCAG | AGGNCGCCCC | TCTCCACGCG | 2160 |
| TGCGCTGTTC | CAGGGAAGGT | GCAGMCAGGC | TGGAGAGGNT | ACAGGTGTCC | CGAG | 2214 |

( 2 ) INFORMATION FOR SEQ ID NO:8:

( i ) SEQUENCE CHARACTERISTICS:
        ( A ) LENGTH: 5077 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| | | | | | |
|---|---|---|---|---|---|
| CCGAACGCTC | CTCGGCCTCT | GGTCTNCTCT | GGNCCTGGGG | ATCCTAGGCA | TCTCAGGTAA | 60 |
| GAAGAGCCCG | CCCGTGGAGC | NAGGTGGATA | AGGCGGGGGC | GGAATTGAAG | GACCAGAGAG | 120 |
| GGCGGCCCGG | GTGTCCCCCT | CCAGGCTCCG | CCCTCTTCTA | GCTTCCACG | CTTCTGTCAC | 180 |
| CACCTGGAGN | TCGGGGCTTC | TCCCCGTCCT | TCCTCCACCC | CAACACACCT | CAATCTTTCA | 240 |
| GANCTGAACC | CAGCACCTTT | TCTGGANTNG | GGGNNTTGCA | CCTAACCTGT | CTCAGGAGAN | 300 |
| ACTGTGGCTC | TCCTGTCCTC | TCCTGCTCTG | TNATGCCCTA | TGGTTCACAG | ACTGGCATCA | 360 |
| TCCCTATTCA | TGATCCTCAA | AGACNCCATC | TCCTCAACTG | TCATAACTCA | GAGCTCTATT | 420 |
| CCCCCTCCAC | CTGGAGCCCT | GGAAACCGGC | TTTCTAGGGC | TTTTCTCCGC | GGTTCTTTCC | 480 |
| CGGAGTTCAG | CGTTGTGGCT | TTTTGTCCAA | GTTACTCAAG | TTTGGGGACA | ATCTCCTTTA | 540 |
| AGCCTTTGAC | TCAGTCTCAT | TTCCACTTTG | CTTTTGCCCC | AAGCCTCTGT | GTCTCTCCCC | 600 |
| CATTTCCTGA | CGATCTGTCA | GAGTCTTAAG | AGTGATTTGG | TTCCCCATCC | CCCTCCAAC | 660 |
| TGGAGTCTCC | TCCTCACTAT | TGATGTGTGC | ATCTGAGACC | CCCATCCCCG | CACCGAGTTT | 720 |
| CCCCATCTCT | GTCAGTAAAG | AGCAAGGCTT | CCAGAGACAA | CCCTCTAATA | GCGCGTCAGT | 780 |
| CCCGAATCTT | GAGTGGGATG | CGGGACTCCC | GTGCTATTTC | TTGGCGGAGG | TCTTTCCTGG | 840 |
| TCCTTATGGA | CACCCCTGGT | TTGGGATATG | GGGCCGCTA | AGATTTCAGA | GATGGGGTCC | 900 |
| CTAGGCTGAG | NCCGCGTTTT | CCCGGGCAGC | GGTCGCGCTA | GAACCTTTCT | GGGCGGACCT | 960 |
| TCAGCCCCGC | GTGGCGCTCG | TGGAGCGCGG | GGGCTCGCTG | TGGCTCAACT | GCAGCACTAA | 1020 |
| CTGTCCGAGG | CCGGAGCGCG | GTGGCCTGGA | GACCTCGCTA | CGCCGAAACG | GGACCCAGAG | 1080 |
| GGGTCTGNAC | TGNCTGGCTC | GACAGCTGGT | GGACATCCGA | GANCCTGAAA | CCCAGCCGGT | 1140 |
| CTGCTTCTTC | CNCTGCGCGC | GCCGCACACT | CCAAGCGCGT | GGGCTCATCC | GAACTTTCCG | 1200 |
| TGAGTTCAGG | GTGGGCACNC | CCCTTGGGTC | TCTGGACCTC | CCCCTCAAGC | TCCTCCCACC | 1260 |
| CGCCCTCTGA | TCCTCCTGCT | TGTTCTGAAA | GTACTACAGC | TGGCTAGAGC | GGAGTTTTTG | 1320 |
| GTCCCTTGCA | GAGCGACCGG | ATCGGGTAGA | GCTAGTGCCT | CTGCCTCCTT | GGCAGCCTGT | 1380 |
| AGGTGAGAAC | TTCACCTTGA | GCTGCAGGGT | CCCGGGGGCA | GGACCCCGAG | CGAGCCTCAC | 1440 |
| ATTGACCTTG | CTGCGAGGCG | GCCAGGAGCT | GATTCGCCGA | AGTTTCGTAG | GCGAGCCACC | 1500 |

| | | | | | |
|---|---|---|---|---|---|
| CCGAGCTCGG | GGTGCGATGC | TCACCGCCAC | GGTCCTGGCG | CGCAGAGAGG | ATCACAGGGC | 1560
| CAATTTCTCA | TGCCTCGCGG | AGCTTGACCT | GCGNCCACAC | GGCTTGGGAC | TGTTTGCANA | 1620
| CAGCTCAGCC | CCCAGACAGC | TCCGCACGTT | TGGTGAGTGT | GGACCCTAAC | TGACAGATTT | 1680
| TAAGAAGTTT | AGGGCAGCCA | GGCGTGGTGG | CATGGTGTCG | TAGGCCCTAA | GTCCCAGCCC | 1740
| AAGCAGANCT | AAGNCGGATC | TCTTGTGAAT | TAAAAGTCTA | GCTCGTCTAC | ATAACGAGGN | 1800
| CTGCATAGTT | AAATCCCCCA | AAAGTCTAAG | CAGCTAGCCC | TTACTTCCAA | CACAAGTACT | 1860
| AGCTTAAGTA | CTTTCTCCTG | TGAGCTTTTT | CCTTTATGTA | TTTACTCGTT | GAGAGAAAAA | 1920
| GAGAGTGTGT | GTACGTGCCT | TTATGCACAT | GCCGCAGTGC | TTGTATGGAA | GTTAAAGAAT | 1980
| AAGGAGGCGT | TCTGCCCTTC | CATCCTGTGG | GTCCTAGGGG | TGGTATTAGC | TCCTCAGGCT | 2040
| TTGTTAGTNA | CAAGCGCCTA | GGCTTGGGGA | GCCATCTCGC | CCGCTCCTCT | GTATCTTTAG | 2100
| GGTGAAACCA | GACAATGCAT | GCAAATTGGT | TGATCAACAC | TGAATGTTTA | GTTCGTAAAT | 2160
| TCAAGCTCTG | TTCTTTGTCT | TCCTCAGCCA | TGCCTCCACT | TTCCCCGAG | CCTTATTGCC | 2220
| CCACGATTCT | TAGAAGTGGG | CTCAGAAAGG | CCGGTGACKT | GCACTTTGGA | TGGACTGTTT | 2280
| CCTGCCCCAG | AAGCCGGGGT | TTACTTCTCT | CTGGGAGATC | AGAGGCTTCA | TCCTAATGTG | 2340
| ACCCTCGACG | GGGAGAGCCT | TGTGGCCACT | GCCACAGCTA | CAGCAAGTGA | AGAACAGGAA | 2400
| GGCACCAAAC | AGCTGATGTG | CATCGTGACC | CTCGGGGGCG | AAAGCAGGGA | GACCCAGGAA | 2460
| AACCTGACTG | TCTACAGTAA | GGGGAATCCA | ACAAGACCTT | CAATAGCTCA | GACTGGGGCT | 2520
| GGGGCTGGGT | CTGGGTCTGG | GGCCAGAGTC | TCACAAAGGC | GGAGCCTATA | AAGTGGGCGG | 2580
| GACCTCCACA | CCAGAACAAG | CCGGGCGGGA | GAGTTCCAGG | GCAGGAGCAG | ATAGAAGTTG | 2640
| GAAATTAATA | GATTGGGTTG | AGTTCCCTGA | GTGGGGAGTG | AACCCCACCC | AATTCTCTGT | 2700
| CCCCAGGCTT | CCCGGCTCCT | CTTCTGACTT | TAAGTGAGCC | AGAAGCCCCC | GAGGGAAAGA | 2760
| TGGTGACCGT | AAGCTGCTGG | GCAGGGGCCC | GAGCCCTTGT | CACCTTGGAG | GGAATTCCAG | 2820
| CTGCGGTCCC | TGGGCAGCCC | GCTGAGCTCC | AGTTAAATGT | CACAAAGAAT | GACGACAAGC | 2880
| GGGGCTTCTT | CTGCGACGCT | GCCCTCGATG | TGGACGGGGA | AACTCTGAGA | AAGAACCAGA | 2940
| GCTCTGAGCT | TCGTGTTCTG | TGTGAGTGGA | TGTTCACTTT | ATCTCTGTGA | ATTCCAAGGA | 3000
| CCCTCTTACC | GGCCCCATCT | TTAACCTTAT | CGTATCCCCT | CTGCCTCATG | CCCGCAGACG | 3060
| CACCTCGGCT | GGATGACTTG | GACTGTCCCA | GGAGCTGGAC | GTGGCCAGAG | GGTCCAGAGC | 3120
| AGACCCTCCA | CTGCGAGGCC | CGTGGAAACC | CTGAGCCCTC | CGTGCACTGT | GCAAGGCCTG | 3180
| ACGGTGGGGC | GGTGCTAGCG | CTGGGCCTGT | TGGGTCCAGT | GACCCGTGCC | CTCGCGGGCA | 3240
| CTTACCGATG | TACAGCAATC | AATGGGCAAG | GCCAGGCGGT | CAAGGATGTG | ACCCTGACTG | 3300
| TGGAATGTGA | GTAGGGGGAG | GTGGGCATGC | TTATCCCTTT | AAGGTCACGG | AGTGTACTGG | 3360
| GAGACTGGCT | ATACGGAAAG | GAAAGAAGCC | TAGGTTCAGC | AGGGATTGGG | AAAACACTGA | 3420
| AGGAAAGTGG | TGTGGTGTTT | ACAAACTTAA | CGGTGGTAAC | TGGGCACGGT | CTGGCAAAAA | 3480
| CAGACAGCCA | AGAGAGTGTG | CCTGGAAGC | TGCAATGGGG | GCTTTGTGGG | AATTGGTCAA | 3540
| CAGCACCCTG | AGATCTCAGG | AAAGGGGCCT | GAAGTTATCT | CCAGAACCCA | TGTGAAGGCA | 3600
| GGAAGAGAGA | ACGCCCACCT | TTTCCTGCTC | CCCCAACCC | CCCCCACAT | ATCACACGGA | 3660
| GTATATAAAT | AAATAAAATG | GCTCCTGCCG | GAGGGAGTGA | GAAGCTGTCT | CCTGCAGGCT | 3720
| CAGAGCAGTG | GTAGTGCATG | CCTTTAATCC | CAGCACTCGG | TAGGCAAAGG | CAGGCAGATC | 3780
| TCTGTGAATG | TGGGGCCAGC | CTGGTCTGTA | CAGAGAAATC | CTGTCTCAAA | ACAAACCAGC | 3840
| AAAGAAACAA | AACCAAAATC | AATTCCAGAT | GCCCCAGCGC | TGGACAGTGT | AGGCTGCCCA | 3900

-continued

| | | | | | |
|---|---|---|---|---|---|
| NGACGTATTA | CTTGNCTGGA | GGGGACAGAG | GCATCGCTTA | GCTGTGTGGC | ACACGGGTC | 3960 |
| CCACCACCTA | GCGTGAGCTG | TGTGCGCTCT | GGAAAGGAGG | AAGTCATGGA | AGGGCCCCTG | 4020 |
| CGTGTGGCCC | GGGAGCACGC | TGGCACTTAC | CGATGCGAAG | CCATCAACGC | CAGGGGATCA | 4080 |
| GCGGNCAAAA | ATGTGGCTGT | CACGGTGGAA | TGTGAGTAGG | GGTGGCTACG | GAAATGTCCA | 4140 |
| CACCTGCGTC | CTCTGTCCTC | AGTGTGAACT | CCTATTTCCC | TGCTTCCTAG | ATGGTCCCAG | 4200 |
| TTNTGAGGAG | TTGGGCTGCC | CCAGCAACTG | GACTTGGGTA | GAAGGATCTG | GAAAACTGTT | 4260 |
| TTCCTGTGAA | GTTGATGGGA | AGCCGGAACC | ACGCGTGGAG | TGCGTGGGCT | CGGAGGGTGC | 4320 |
| AAGCGAAGGG | GTAGTGTTGC | CCCTGGTGTC | CTCGAACTCT | GGTTCCAGAA | ACTCTATGAC | 4380 |
| TCCTGGTAAC | CTGTCACCGG | GTATTTACCT | CTGCAACGCC | ACCAACCGGC | ATGGCTCCAC | 4440 |
| AGTCAAAACA | GTCGTCGTGA | GCGCGGAATG | TGAGCAGGGG | CCCAGGTGGG | CGGAGAGTAC | 4500 |
| CGGGTGTCCC | AGGATCTTTT | CTTTCCCTGA | TGCCCCTCCT | TATGGTGGCT | GATCTGCAGC | 4560 |
| ACCGCCACAG | ATGGATGAAT | CCAGTTGCCC | GAGTCACCAG | ACATGGCTGG | AAGGAGCCGA | 4620 |
| GGCTACTGCG | CTGGCCTGCA | GTGACAGGGG | NCGCCCTCT | CCACGCGTGC | GCTGTTCCAG | 4680 |
| GGAAGGTGCA | GCCAGGCTGG | AGAGGCTACA | GGTGTCCCGA | GAGGATGCGG | GGACCTACCT | 4740 |
| GTGTGTGGCT | ACCAACGCGC | ATGGCACGGA | TTCACGGACC | GTCACTGTGG | GTGTGGAATG | 4800 |
| TGAGTGAGGA | CAGCGCTGAA | TGAAGACGAC | TCAGACCGCC | AGAAAGTGC | CTTGAGGCCT | 4860 |
| GGGATGTATG | ATCCAGTGGG | TAGAGTGCTC | AATTAGCACT | CACTAAAATG | TATATTCTAT | 4920 |
| TCCTAATACT | CTTTAATTTT | ANCCTTTGGG | AGGCAGAGAC | AGGCAGATCT | CTGTTCCGGG | 4980 |
| ATAACCTGCT | CTCTGTCTAG | GACAGCTTGG | TCTACAGAGG | GGNTACAGGC | CCCCCCTCCC | 5040 |
| AAGATTGNAT | AGCAACCCTC | TGGCTCCCTG | TCTCTCT | | | 5077 |

( 2 ) INFORMATION FOR SEQ ID NO:9:

( i ) SEQUENCE CHARACTERISTICS:
    ( A ) LENGTH: 1472 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:9:

| | | | | | |
|---|---|---|---|---|---|
| NGAATTCCGG | CGGATCGGGT | AGAGCTAGTG | CCTCTGCCTC | CTTGGCAGCC | TGTAGGTGAG | 60 |
| AACTTCACCT | TGAGCTGCAG | GGTCCCGGGG | GCAGGACCCC | GAGCGAGCCT | CACATTGACC | 120 |
| TTGCTGCGAG | GCGGCCAGGA | GCTGATTCGC | CGAAGTTTCG | TAGGCGAGCC | ACCCCGAGCT | 180 |
| CGGGGTGCGA | TGCTCACCGC | CACGGTCCTG | GCGCGCAGAG | AGGATCACAG | GCCAATTTC | 240 |
| TCATGCCTCG | CGGAGCTTGA | CCTGCGGCCA | CACGGCTTGG | GACTGTTTGC | AAACAGCTCA | 300 |
| GCCCCAGAC | AGCTCCGCAC | GTTGCCATG | CCTCCACTTT | CCCGAGCCT | TATTGCCCCA | 360 |
| CGATTCTTAG | AAGTGGGCTC | AGAAAGGCCG | GTGACTTGCA | CTTTGGATGG | ACTGTTTCCT | 420 |
| GCCCCAGAAG | CCGGGGTTTA | CCTCTCTCTG | GGAGATCAGA | GGCTTCATCC | TAATGTGACC | 480 |
| CTCGACGGGG | AGAGCCTTGT | GGCCACTGCC | ACAGCTACAG | CAAGTGAAGA | ACAGGAAGGC | 540 |
| ACCAAACAGC | TGATGTGCAT | CGTGACCCTC | GGGGGCGAAA | GCAGGGAGAC | CCAGGAAAAC | 600 |
| CTGACTGTCT | ACAGCTTCCC | GGCTCCTCTT | CTGACTTTAA | GTGAGCCAGA | AGCCCCGAG | 660 |
| GGAAAGATGG | TGACCGTAAG | CTGCTGGGCA | GGGGCCCGAG | CCCTTGTCAC | CTTGGAGGGA | 720 |
| ATTCCAGCTG | CGGTCCCTGG | GCAGCCGCT | GAGCTCCAGT | TAAATGTCAC | AAAGAATGAC | 780 |
| GACAAGCGGG | GCTTCTTCTG | CGACGCTGCC | CTCGATGTGG | ACGGGAAAC | TCTGAGAAAG | 840 |

| | | | | | |
|---|---|---|---|---|---|
| AACCAGAGCT | CTGAGCTTCG | TGTTCTGTGT | GAGTGGATGT | TCACTTTATC | TCTGTGAATT | 900 |
| CCAAGGACCC | TCTTACCGGC | CCCATCTTTA | ACCTTATCGT | ATCCCTCTG | CCTCATGCCC | 960 |
| GCAGACGCAC | CTCGGCTGGA | TGACTTGGAC | TGTCCCAGGA | GCTGGACGTG | GCCAGAGGGT | 1020 |
| CCAGAGCAGA | CCCTCCACTG | CGAGGCCCGT | GGAAACCCTG | AGCCCTCCGT | GCACTGTGCA | 1080 |
| AGGCCTGACG | GTGGGCGGT | GCTAGCGCTG | GGCCTGTTGG | GTCCAGTGAC | CCGTGCCCTC | 1140 |
| GCGGGCACTT | ACCGATGTAC | AGCAATCAAT | GGGCAAGGCC | AGGCGGTCAA | GGATGTGACC | 1200 |
| CTGACTGTGG | AATATGCCCC | AGCGCTGGAC | AGTGTAGGCT | GCCCAGAACG | TATTACTTGG | 1260 |
| CTGGAGGGGA | CAGAGGCATC | GCTTAGCTGT | GTGGCACACG | GGTCCCACC | ACCTAGCGTG | 1320 |
| AGCTGTGTGC | GCTCTGGAAA | GGAGGAAGTC | ATGGAAGGGC | CCCTGCGTTT | GGCCGGGAG | 1380 |
| CACGCTGGCA | CTTACCGATG | CGAAGCCATC | AACGCCAGGG | GATCAGCGGC | CAAAAATGTG | 1440 |
| GCTGTCACGG | TGGAATATGG | TCCCCGGAAT | TC | | | 1472 |

(2) INFORMATION FOR SEQ ID NO:10:

(i) SEQUENCE CHARACTERISTICS:
        (A) LENGTH: 2550 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

| | | | | | |
|---|---|---|---|---|---|
| CCTCTGCCTC | CTTGGCAGCC | TGTAGGTGAG | AACTTCACCT | TGAGCTGCAG | GGTCCCGGGG | 60 |
| GCAGGACCCC | GAGCGAGCCT | CACATTGACC | TTGCTGCGAG | GCGGCCAGGA | GCTGATTCGC | 120 |
| CGAAGTTTCG | TAGGCGAGCC | ACCCCGAGCT | CGGGGTGCGA | TGCTCACCGC | CACGGTCCTG | 180 |
| GCGCGCAGAG | AGGATCACAG | GGCCAATTTC | TCATGCCTCG | CGGAGCTTGA | CCTGCGGCCA | 240 |
| CACGGCTTGG | GACTGTTTGC | AAACAGCTCA | GCCCCAGAC | AGCTCCGCAC | GTTTGCCATG | 300 |
| CCTCCACTTT | CCCCGAGCCT | TATTGCCCCA | CGATTCTTAG | AAGTGGGCTC | AGAAAGGCCG | 360 |
| GTGACTTGCA | CTTTGGATGG | ACTGTTTCCT | GCCCCAGAAG | CCGGGGTTTA | CCTCTCTCTG | 420 |
| GGAGATCAGA | GGCTTCATCC | TAATGTGACC | CTCGACGGGG | AGAGCCTTGT | GGCCACTGCC | 480 |
| ACAGCTACAG | CAAGTGAAGA | ACAGGAAGGC | ACCAAACAGC | TGATGTGCAT | CGTGACCCTC | 540 |
| GGGGGCGAAA | GCAGGGAGAC | CCAGGAAAAC | CTGACTGTCT | ACAGCTTCCC | GGCTCCTCTT | 600 |
| CTGACTTTAA | GTGAGCCAGA | AGCCCCCGAG | GGAAAGATGG | TGACCGTAAG | CTGCTGGGCA | 660 |
| GGGCCCGAG | CCCTTGTCAC | CTTGGAGGGA | ATTCCAGCTG | CGGTCCCTGG | GCAGCCCGCT | 720 |
| GAGCTCCAGT | TAAATGTCAC | AAAGAATGAC | GACAAGCGGG | GCTTCTTCTG | CGACGCTGCC | 780 |
| CTCGATGTGG | ACGGGGAAAC | TCTGAGAAAG | AACCAGAGCT | CTGAGCTTCG | TGTTCTGTAC | 840 |
| GCACCTCGGC | TGGATGACTT | GGACTGTCCC | AGGAGCTGGA | CGTGGCCAGA | GGGTCCAGAG | 900 |
| CAGACCCTCC | ACTGCGAGGC | CCGTGGAAAC | CCTGAGCCCT | CCGTGCACTG | TGCAAGGCCT | 960 |
| GACGGTGGGG | CGGTGCTAGC | GCTGGGCCTG | TTGGGTCCAG | TGACCCGTGC | CCTCGCGGGC | 1020 |
| ACTTACCGAT | GTACAGCAAT | CAATGGGCAA | GGCCAGGCGG | TCAAGGATGT | GACCCTGACT | 1080 |
| GTGGAATATG | CCCCAGCGCT | GGACAGTGTA | GGCTGCCCAG | AACGTATTAC | TTGGCTGGAG | 1140 |
| GGGACAGAGG | CATCGCTTAG | CTGTGTGGCA | CACGGGTCC | CACCACCTAG | CGTGAGCTGT | 1200 |
| GTGCGCTCTG | GAAAGGAGGA | AGTCATGGAA | GGGCCCCTGC | GTGTGGCCCG | GGAGCACGCT | 1260 |
| GGCACTTACC | GATGCGAAGC | CATCAACGCC | AGGGGATCAG | CGGCCAAAAA | TGTGGCTGTC | 1320 |

```
ACGGTGGAAT ATGGTCCCAG TTTTGAGGAG TTGGGCTGCC CCAGCAACTG GACTTGGGTA        1380

GAAGGATCTG GAAAACTGTT TTCCTGTGAA GTTGATGGGA AGCCGGAACC ACGCGTGGAG        1440

TGCGTGGGCT CGGAGGGTGC AAGCGAAGGG GTAGTGTTGC CCCTGGTGTC CTCGAACTCT        1500

GGTTCCAGAA ACTCTATGAC TCCTGGTAAC CTGTCACCGG GTATTTACCT CTGCAACGCC        1560

ACCAACCGGC ATGGCTCCAC AGTCAAAACA GTCGTCGTGA GCGCGGAATC ACCGCCACAG        1620

ATGGATGAAT CCAGTTGCCC GAGTCACCAG ACATGGCTGG AAGGAGCCGA GGCTACTGCG        1680

CTGGCCTGCA GTGCCAGAGG CCGCCCCTCT CCACGCGTGC GCTGTTCCAG GGAAGGTGCA        1740

GCCAGGCTGG AGAGGCTACA GGTGTCCCGA GAGGATGCGG GGACCTACCT GTGTGTGGCT        1800

ACCAACGCGC ATGGCACGGA TTCACGGACC GTCACTGTGG GTGTGGAATA CCGGCCTGTG        1860

GTGGCTGAGC TGGCAGCCTC GCCCCCAAGC GTGCGGCCTG GCGGAAACTT CACTCTGACC        1920

TGCCGTGCAG AGGCCTGGCC TCCAGCCCAG ATCAGCTGGC GCGCGCCCCC GGGAGCTCTC        1980

AACCTCGGTC TCTCCAGCAA CAACAGCACG CTGAGCGTGG CGGGTGCCAT GGGCAGCCAT        2040

GGTGGCGAGT ATGAGTGCGC AGCCACCAAT GCGCATGGGC GCCACGCACG GCGCATCACG        2100

GTGCGCGTGG CCGGTCCATG GCTGTGGGTC GCTGTGGGCG GTGCGGCAGG GGGCGCGGCG        2160

CTGCTGGCCG CAGGGGCCGG CCTGGCCTTC TACGTGCAGT CCACCGCTTG CAAGAAGGGA        2220

GAGTACAACG TCCAGGAGGC TGAGAGCTCA GGCGAGGCGG TGTGTCTCAA TGGCGCGGGC        2280

GGGACACCGG GTGCAGAAGG CGGAGCAGAG ACCCCCGGCA CTGCCGAGTC ACCTGCAGAT        2340

GGCGAGGTTT TCGCCATCCA GCTGACATCT TCCTGAGCCT GTATCCAGCT CCCCCAGGGG        2400

CCTCGAAAGC ACAGGGGTGG ACGTATGTAT TGTTCACTCT CTATTTATTC AACTCCAGGG        2460

GCGTCGTCCC CGTTTCTAC CCATTCCCTT AATAAAGTTT TTATAGGAGA AAAAAAAAA        2520

AAAAAAAAAA AAAAAAAAA AAAAAAAAA                                         2550
```

( 2 ) INFORMATION FOR SEQ ID NO:11:

( i ) SEQUENCE CHARACTERISTICS:
        ( A ) LENGTH: 222 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
AATTCGATCA CTCGCGCTCC CCTCGCCTTC TGCGCTCTCC CCTCCCTGGC AGCGGCGGCA         60

ATGCCGGGGC CTTCACCAGG GCTGCGCCGA ACGCTCCTCG GCCTCTGGGC TGCCCTGGGC        120

CTGGGGATCC TAGGCATCTC AGCGGTCGCG CTAGAACCTT TCTGGGCGGA CCTTCAGCCC        180

CGCGTGGCGC TCGTGGAGCG CGGGGGCTCG CTGTGGCTCA AC                          222
```

( 2 ) INFORMATION FOR SEQ ID NO:12:

( i ) SEQUENCE CHARACTERISTICS:
        ( A ) LENGTH: 292 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

```
TGTGGAGCTG GCACCCCTGC CTCCTTGGCA GCCGGTGGGC CAGAACTTCA CCCTGCGCTG         60

CCAAGTGGAG GGTGGGTCGC CCCGGACCAG CCTCACGGTG GTGCTGCTTC GCTGGGAGGA        120
```

```
GGAGCTGAGC CGGCAGCCCG CAGTGGAGGA GCCAGCGGAG GTCACTGCCA CTGTGCTGGC      180

CAGCAGAGAC GACCACGGAG CCCCTTTCTC ATGCCGCACA GAACTGGACA TGCAGCCCCA      240

GGGGCTGGGA CTGTTCGTGA ACACCTCAGC CCCCCGCCAG CTCCGAACCT TT              292
```

( 2 ) INFORMATION FOR SEQ ID NO:13:

( i ) SEQUENCE CHARACTERISTICS:
        ( A ) LENGTH: 105 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

```
Pro  Asp  Arg  Val  Glu  Leu  Val  Pro  Leu  Pro  Pro  Trp  Gln  Pro  Val  Gly
 1              5                        10                       15

Glu  Asn  Phe  Thr  Leu  Ser  Cys  Arg  Val  Pro  Gly  Ala  Gly  Pro  Arg  Ala
              20                        25                       30

Ser  Leu  Thr  Leu  Thr  Leu  Leu  Arg  Gly  Gly  Gln  Glu  Leu  Ile  Arg  Arg
         35                        40                       45

Ser  Phe  Val  Gly  Glu  Pro  Pro  Arg  Ala  Arg  Cys  Ala  Met  Leu  Thr  Ala
    50                        55                       60

Thr  Val  Leu  Ala  Arg  Arg  Glu  Asp  His  Arg  Asp  Asn  Phe  Ser  Cys  Leu
65                       70                       75                        80

Ala  Glu  Leu  Asp  Leu  Arg  Thr  His  Gly  Leu  Gly  Leu  Phe  Ala  Asn  Ser
                   85                        90                       95

Ser  Ala  Pro  Arg  Gln  Leu  Arg  Thr  Phe
              100                      105
```

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

```
GAACTCGAGG CCATGCCTCC ACTTTCC                                           27
```

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

```
CCATAAGCTT TATTCCACCG TGACAGCCAC                                        30
```

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

AACGTGCGGA GCTGTCTG 18

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

ACGGAATTCG AAGCCATCAA CGCCAGG 27

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CATGAATTCC GAATCTTGAG TGGGATG 27

( 2 ) INFORMATION FOR SEQ ID NO:19:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

ATAGAATTCC TCGGGACACC TGTAGCC 27

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

CARGGTGACA AGGGCTCG 18

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

TATGAATTCA GTTGAGCCAC AGCGAGC 27

( 2 ) INFORMATION FOR SEQ ID NO:22:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:22:

| | | | |
|---|---|---|---|
| CCGGGTCCTA GAGGTGGACA CGCA | | | 24 |

( 2 ) INFORMATION FOR SEQ ID NO:23:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:23:

TGCAGTGTCT CCTGGCTCTG GTTC                                                      24

( 2 ) INFORMATION FOR SEQ ID NO:24:

( i ) SEQUENCE CHARACTERISTICS:
    ( A ) LENGTH: 992 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:24:

| | | | | | |
|---|---|---|---|---|---|
| GCGAAAACCG | GGAGACCCGG | GAGAACGTGA | CCATCTACAG | CTTCCCGGCA | CCACTCCTGA | 60 |
| CCCTGAGCGA | ACCCAGCGTC | TCCGAGGGGC | AGATGGTGAC | AGTAACCTGC | GCAGCTGGGG | 120 |
| CCCAAGCTCT | GGTCACACTG | GAGGGAGTTC | CAGCCGCGGT | CCCGGGGCAG | CCCGCCCAGC | 180 |
| TTCAGCTAAA | TGCCACCGAG | AACGACGACA | GACGCAGCTT | CTTCTGCGAC | GCCACCCTCG | 240 |
| ATGTGGACGG | GGAGACCCTG | ATCAAGAACA | GGAGCGCAGA | GCTTCGTGTC | CTATACGCTC | 300 |
| CCCGGCTAGA | CGATTCGGAC | TGCCCCAGGA | GTTGGACGTG | GCCCGAGGGC | CCAGAGCAGA | 360 |
| CGCTGCGCTG | CGAGGCCCGC | GGGAACCCAG | AACCCTCAGT | GCACTGTGCG | CGCTCCGACG | 420 |
| GCGGGGCCGT | GCTGGCTCTG | GGCCTGCTGG | GTCCAGTCAC | TCGGGCGCTC | TCAGGCACTT | 480 |
| ACCGCTGCAA | GGCGGCCAAT | GATCAAGGCG | AGGCGGTCAA | GGACGTAACG | CTAACGGTGG | 540 |
| AGTACGCACC | AGCGCTGGAC | AGCGTGGGCT | GCCCAGAACG | CATTACTTGG | CTGGAGGGAA | 600 |
| CAGAAGCCTC | GCTGAGCTGT | GTGGCGCACG | GGGTACCGCC | GCCTGATGTG | ATCTGCGTGC | 660 |
| GCTCTGGAGA | ACTCGGGGCC | GTCATCGAGG | GGCTGTTGCG | TGTGGCCCGG | GAGCATGCGG | 720 |
| GCACTTACCG | CTGCGAAGCC | ACCAACCCTC | GGGGCTCTGC | GGCCAAAAAT | GTGGCCGTCA | 780 |
| CGGTGGAATA | TGGCCCCAGG | TTTGAGGAGC | CGAGCTGCCC | CAGCAATTGG | ACATGGGTGG | 840 |
| AAGGATCTGG | GCGCCTGTTT | TCCTGTGAGG | TCGATGGGAA | GCCACAGCCA | AGCGTGAAGT | 900 |
| GCGTGGGCTC | CGGGGCACC | ACTGAGGGGG | TGCTGCTGCC | GCTGGCACCC | CCAGACCCTA | 960 |
| GTCCAGAGC | TCCCAGAATC | CCTAGAGTCC | TG | | | 992 |

( 2 ) INFORMATION FOR SEQ ID NO:25:

(i) SEQUENCE CHARACTERISTICS:
   (A) LENGTH: 2775 base pairs
   (B) TYPE: nucleic acid
   (C) STRANDEDNESS: single
   (D) TOPOLOGY: linear (ii) MOLECULE TYPE: cDNA (xi) SEQUENCE DESCRIPTION: SEQ ID NO:25:

```
GCAGCCTCGC GTGGCGTTCG TGGAGCGCGG GGGCTCGCTG TGGCTGAATT GCAGCACCAA      60
CTGCCCTCGG CCGGAGCGCG GTGGCCTGGA GACCTCGCTG CGCCGAAACG GGACCCAGAG     120
GGGTTTGCGT TGGTTGGCGC GGCAGCTGGT GGACATTCGC GAGCCGGAGA CTCAGCCCGT     180
CTGCTTCTTC CGCTGCGCGC GGCGCACACT ACAGGCGCGT GGGCTCATTC GCACTTTCCA     240
GCGACCAGAT CGCGTAGAGC TGATGCCGCT GCCTCCCTGG CAGCCGGTGG GCGAGAACTT     300
CACCCTGAGC TGTAGGGTCC CCGGCGCCGG GCCCCGTGCG AGCCTCACGC TGACCCTGCT     360
GCGGGGCGCC CAGGAGCTGA TCCGCCGCAG CTTCGCCGGT GAACCACCCC GAGCGCGGGG     420
CGCGGTGCTC ACAGCCACGG TACTGGCTCG GAGGGAGGAC CATGGAGCCA ATTTCTCGTG     480
TCGCGCCGAG CTGGACCTGC GGCCGCACGG ACTGGGACTG TTTGAAAACA GCTCGGCCCC     540
CAGAGAGCTC CGAACCTTCT CCCTGTCTCC GGATGCCCCG CGCCTCGCTG CTCCCCGGCT     600
CTTGGAAGTT GGCTCGGAAA GGCCCGTGAG CTGCACTCTG GACGGACTGT TCCAGCCTC     660
AGAGGCCAGG GTCTACCTCG CACTGGGGGA CCAGAATCTG AGTCCTGATG TCACCCTCGA     720
AGGGGACGCA TTCGTGGCCA CTGCCACAGC CACAGCTAGC GCAGAGCAGG AGGGTGCCAG     780
GCAGCTGGTC TGCAACGTCA CCCTGGGGGG CGAAAACCGG GAGACCCGGG AGAACGTGAC     840
CATCTACAGC TTCCCGGCAC CACTCCTGAC CCTGAGCGAA CCCAGCGTCT CCGAGGGGCA     900
GATGGTGACA GTAACCTGCG CAGCTGGGGC CCAAGCTCTG GTCACACTGG AGGGAGTTCC     960
AGCCGCGGTC CCGGGGCAGC CCGCCCAGCT TCAGCTAAAT GCCACCGAGA ACGACGACAG    1020
ACGCAGCTTC TTCTGCGACG CCACCCTCGA TGTGGACGGG GAGACCCTGA TCAAGAACAG    1080
GAGCGCAGAG CTTCGTGTCC TATACGCTCC CCGGCTAGAC GATTCGGACT GCCCCAGGAG    1140
TTGGACGTGG CCCGAGGGCC CAGAGCAGAC GCTGCGCTGC GAGGCCCGCG GAACCCAGA    1200
ACCCTCAGTG CACTGTGCGC GCTCCGACGG CGGGGCCGTG CTGGCTCTGG GCCTGCTGGG    1260
TCCAGTCACT CGGGCGCTCT CAGGCACTTA CCGCTGCAAG GCGGCCAATG ATCAAGGCGA    1320
GGCGGTCAAG GACGTAACGC TAACGGTGGA GTACGCACCA GCGCTGGACA GCGTGGGCTG    1380
CCCAGAACGC ATTACTTGGC TGGAGGGAAC AGAAGCCTCG CTGAGCTGTG TGGCGCACGG    1440
GGTACCGCCG CCTGATGTGA TCTGCGTGCG CTCTGGAGAA CTCGGGCCG TCATCGAGGG    1500
GCTGTTGCGT GTGGCCCGGG AGCATGCGGG CACTTACCGC TGCGAAGCCA CCAACCCTCG    1560
GGGCTCTGCG GCCAAAAATG TGGCCGTCAC GGTGGAATAT GGCCCCAGGT TTGAGGAGCC    1620
GAGCTGCCCC AGCAATTGGA CATGGGTGGA AGGATCTGGG CGCCTGTTTT CCTGTGAGGT    1680
CGATGGGAAG CCACAGCCAA GCGTGAAGTG CGTGGGCTCC GGGGCACCA CTGAGGGGT    1740
GCTGCTGCCG CTGGCACCCC CAGACCCTAG TCCAGAGCT CCCAGAATCC CTAGAGTCCT    1800
GGCACCCGGT ATCTACGTCT GCAACGCCAC CAACCGCCAC GGCTCCGTGG CCAAAACAGT    1860
CGTCGTGAGC GCGGAGTCGC CACCGGAGAT GGATGAATCT ACCTGCCCAA GTCACCAGAC    1920
GTGGCTGGAA GGGGCTGAGG CTTCCGCGCT GGCCTGCGCC GCCCGGGTC GCCCTTCCCC    1980
AGGAGTGCGC TGCTCTCGGG AAGGCATCCC ATGGCCTGAG CAGCAGCGCG TGTCCCGAGA    2040
GGACGCGGGC ACTTACCACT GTGTGGCCAC CAATGCGCAT GGCACGGACT CCCGGACCGT    2100
```

| | | | | | |
|---|---|---|---|---|---|
| CACTGTGGGC | GTGGAATACC | GGCCAGTGGT | GGCCGAACTT | GCTGCCTCGC | CCCCTGGAGG | 2160 |
| CGTGCGCCCA | GGAGGAAACT | TCACGTTGAC | CTGCCGCGCG | GAGGCCTGGC | CTCCAGCCCA | 2220 |
| GATCAGCTGG | CGCGCGCCCC | CGAGGGCCCT | CAACATCGGC | CTGTCGAGCA | ACAACAGCAC | 2280 |
| ACTGAGCGTG | GCAGGCGCCA | TGGGAAGCCA | CGGCGGCGAG | TACGAGTGCG | CACGCACCAA | 2340 |
| CGCGCACGGG | CGCCACGCGC | GGCGCATCAC | GGTGCGCGTG | GCCGGTCCGT | GGCTATGGGT | 2400 |
| CGCCGTGGGC | GGCGCGGCGG | GGGGCGCGGC | GCTGCTGGCC | GCGGGGCCG | GCCTGGCCTT | 2460 |
| CTACGTGCAG | TCCACCGCCT | GCAAGAAGGG | CGAGTACAAC | GTGCAGGAGG | CCGAGAGCTC | 2520 |
| AGGCGAGGCC | GTGTGTCTGA | ACGGAGCGGG | CGGCGGCGCT | GGCGGGGCGG | CAGGCGCGGA | 2580 |
| GGGCGGACCC | GAGGCGGCGG | GGGGCGCGGC | CGAGTCGCCG | GCGGAGGGCG | AGGTCTTCGC | 2640 |
| CATACAGCTG | ACATCGGCGT | GAGCCCGCTC | CCCTCTCCGC | GGGCCGGGAC | GCCCCCAGA | 2700 |
| CTCACACGGG | GGCTTATTTA | TTGCTTTATT | TATTTACTTA | TTCATTTATT | TATGTATTCA | 2760 |
| ACTCCAAGGG | AATTC | | | | | 2775 |

( 2 ) INFORMATION FOR SEQ ID NO:26:

( i ) SEQUENCE CHARACTERISTICS:
        ( A ) LENGTH: 1557 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

| | | | | | |
|---|---|---|---|---|---|
| CGCGCTCTCC | TCGCCTCCTG | TGCTTTCCCC | GCCGCGGCGA | TGCCAGGGCC | TTCGCCAGGG | 60 |
| CTGCGCCGGG | CGCTACTCGG | CCTCTGGGCT | GCTCTGGGCC | TGGGCTCTT | CGGCCTCTCA | 120 |
| GCGGTCTCGC | AGGAGCCCTT | CTGGGCGGAC | CTGCAGCCTC | GCGTGGCGTT | CGTGGAGCGC | 180 |
| GGGGGCTCGC | TGTGGCTGAA | TTGCAGCACC | AACTGCCCTC | GGCCGGAGCG | CGGTGGCCTG | 240 |
| GAGACCTCGC | TGCGCCGAAA | CGGGACCCAG | AGGGGTTTGC | GTTGGTTGGC | GCGGCAGCTG | 300 |
| GTGGACATTC | GCGAGCCGGA | GACTCAGCCC | GTCTGCTTCT | TCCGCTGCGC | GCGGCGCACA | 360 |
| CTACAGGCGC | GTGGGCTCAT | TCGCACTTTC | CAGCGACCAG | ATCGCGTAGA | GCTGATGCCG | 420 |
| CTGCCTCCCT | GGCAGCCGGT | GGGCGAGAAC | TTCACCCTGA | GCTGTAGGGT | CCCCGGCGCC | 480 |
| GGGCCCCGTG | CGAGCCTCAC | GCTGACCCTG | CTGCGGGGCG | CCCAGGAGCT | GATCCGCCGC | 540 |
| AGCTTCGCCG | GTGAACCACC | CCGAGCGCGG | GGCGCGGTGC | TCACAGCCAC | GGTACTGGCT | 600 |
| CGGAGGGAGG | ACCATGGAGC | CAATTTCTCG | TGTCGCGCCG | AGCTGGACCT | GCGGCCGCAC | 660 |
| GGACTGGGAC | TGTTTGAAAA | CAGCTCGGCC | CCCAGAGAGC | TCCGAACCTT | CTCCCTGTCT | 720 |
| CCGGATGCCC | CGCGCCTCGC | TGCTCCCCGG | CTCTTGGAAG | TTGGCTCGGA | AAGGCCCGTG | 780 |
| AGCTGCACTC | TGGACGGACT | GTTTCCAGCC | TCAGAGGCCA | GGGTCTACCT | CGCACTGGGG | 840 |
| GACCAGAATC | TGAGTCCTGA | TGTCACCCTC | GAAGGGACG | CATTCGTGGC | CACTGCCACA | 900 |
| GCCACAGCTA | GCGCAGAGCA | GGAGGGTGCC | AGGCAGCTGG | TCTGCAACGT | CACCCTGGGG | 960 |
| GGCGAAAACC | GGGAGACCCG | GGAGAACGTG | ACCATCTACA | GCTTCCCGGC | ACCACTCCTG | 1020 |
| ACCCTGAGCG | AACCCAGCGT | CTCCGAGGGG | CAGATGGTGA | CAGTAACCTG | CGCAGCTGGG | 1080 |
| GCCCAAGCTC | TGGTCACACT | GGAGGGAGTT | CCAGCCGCGG | TCCCGGGGCA | GCCCGCCCAG | 1140 |
| CTTCAGCTAA | ATGCCACCGA | GAACGACGAC | AGACGCAGCT | TCTTCTGCGA | CGCCACCCTC | 1200 |
| GATGTGGACG | GGGAGACCCT | GATCAAGAAC | AGGAGCGCAG | AGCTTCGTGT | CCTATACGCT | 1260 |
| CCCCGGCTAG | ACGATTCGGA | CTGCCCCAGG | AGTTGGACGT | GGCCCGAGGG | CCCAGAGCAG | 1320 |

| | | | | |
|---|---|---|---|---|
| ACGCTGCGCT | GCGAGGCCCG | CGGGAACCCA | GAACCCTCAG | TGCACTGTGC GCGCTCCGAC | 1380 |
| GGCGGGGCCG | TGCTGGCTCT | GGGCCTGCTG | GGTCCAGTCA | CTCGGGCGCT CTCAGGCACT | 1440 |
| TACCGCTGCA | AGGCGGCCAA | TGATCAAGGC | GAGGCGGTCA | AGGACGTAAC GCTAACGGTG | 1500 |
| GAGTACGCAC | CAGCGCTGGA | CAGCGTGGGC | TGCCCAGAAC | GCATTACTTG GCTGGAG | 1557 |

( 2 ) INFORMATION FOR SEQ ID NO:27:

( i ) SEQUENCE CHARACTERISTICS:
        ( A ) LENGTH: 2927 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 40..2814

( x i ) SEQUENCE DESCRIPTION: SEQ ID NO:27:

```
CGCGCTCTCC TCGCCTCCTG TGCTTTCCCC GCCGCGGCG ATG CCA GGG CCT TCG              54
                                          Met Pro Gly Pro Ser
                                          1               5

CCA GGG CTG CGC CGG GCG CTA CTC GGC CTC TGG GCT GCT CTG GGC CTG            102
Pro Gly Leu Arg Arg Ala Leu Leu Gly Leu Trp Ala Ala Leu Gly Leu
            10                  15                  20

GGG CTC TTC GGC CTC TCA GCG GTC TCG CAG GAG CCC TTC TGG GCG GAC            150
Gly Leu Phe Gly Leu Ser Ala Val Ser Gln Glu Pro Phe Trp Ala Asp
        25                  30                  35

CTG CAG CCT CGC GTG GCG TTC GTG GAG CGC GGG GGC TCG CTG TGG CTG            198
Leu Gln Pro Arg Val Ala Phe Val Glu Arg Gly Gly Ser Leu Trp Leu
    40                  45                  50

AAT TGC AGC ACC AAC TGC CCT CGG CCG GAG CGC GGT GGC CTG GAG ACC            246
Asn Cys Ser Thr Asn Cys Pro Arg Pro Glu Arg Gly Gly Leu Glu Thr
55                  60                  65

TCG CTG CGC CGA AAC GGG ACC CAG AGG GGT TTG CGT TGG TTG GCG CGG            294
Ser Leu Arg Arg Asn Gly Thr Gln Arg Gly Leu Arg Trp Leu Ala Arg
70                  75                  80                  85

CAG CTG GTG GAC ATT CGC GAG CCG GAG ACT CAG CCC GTC TGC TTC TTC            342
Gln Leu Val Asp Ile Arg Glu Pro Glu Thr Gln Pro Val Cys Phe Phe
            90                  95                  100

CGC TGC GCG CGG CGC ACA CTA CAG GCG CGT GGG CTC ATT CGC ACT TTC            390
Arg Cys Ala Arg Arg Thr Leu Gln Ala Arg Gly Leu Ile Arg Thr Phe
        105                 110                 115

CAG CGA CCA GAT CGC GTA GAG CTG ATG CCG CTG CCT CCC TGG CAG CCG            438
Gln Arg Pro Asp Arg Val Glu Leu Met Pro Leu Pro Pro Trp Gln Pro
    120                 125                 130

GTG GGC GAG AAC TTC ACC CTG AGC TGT AGG GTC CCC GGC GCC GGG CCC            486
Val Gly Glu Asn Phe Thr Leu Ser Cys Arg Val Pro Gly Ala Gly Pro
135                 140                 145

CGT GCG AGC CTC ACG CTG ACC CTG CTG CGG GGC GCC CAG GAG CTG ATC            534
Arg Ala Ser Leu Thr Leu Thr Leu Leu Arg Gly Ala Gln Glu Leu Ile
150                 155                 160                 165

CGC CGC AGC TTC GCC GGT GAA CCA CCC CGA GCG CGG GGC GCG GTG CTC            582
Arg Arg Ser Phe Ala Gly Glu Pro Pro Arg Ala Arg Gly Ala Val Leu
            170                 175                 180

ACA GCC ACG GTA CTG GCT CGG AGG GAG GAC CAT GGA GCC AAT TTC TCG            630
Thr Ala Thr Val Leu Ala Arg Arg Glu Asp His Gly Ala Asn Phe Ser
        185                 190                 195

TGT CGC GCC GAG CTG GAC CTG CGG CCG CAC GGA CTG GGA CTG TTT GAA            678
Cys Arg Ala Glu Leu Asp Leu Arg Pro His Gly Leu Gly Leu Phe Glu
```

```
     200                      205                        210
AAC AGC TCG GCC CCC AGA GAG CTC CGA ACC TTC TCC CTG TCT CCG GAT        726
Asn Ser Ser Ala Pro Arg Glu Leu Arg Thr Phe Ser Leu Ser Pro Asp
    215                     220                     225

GCC CCG CGC CTC GCT GCT CCC CGG CTC TTG GAA GTT GGC TCG GAA AGG        774
Ala Pro Arg Leu Ala Ala Pro Arg Leu Leu Glu Val Gly Ser Glu Arg
230                     235                     240                 245

CCC GTG AGC TGC ACT CTG GAC GGA CTG TTT CCA GCC TCA GAG GCC AGG        822
Pro Val Ser Cys Thr Leu Asp Gly Leu Phe Pro Ala Ser Glu Ala Arg
                250                     255                     260

GTC TAC CTC GCA CTG GGG GAC CAG AAT CTG AGT CCT GAT GTC ACC CTC        870
Val Tyr Leu Ala Leu Gly Asp Gln Asn Leu Ser Pro Asp Val Thr Leu
            265                     270                     275

GAA GGG GAC GCA TTC GTG GCC ACT GCC ACA GCC ACA GCT AGC GCA GAG        918
Glu Gly Asp Ala Phe Val Ala Thr Ala Thr Ala Thr Ala Ser Ala Glu
                280                     285                     290

CAG GAG GGT GCC AGG CAG CTG GTC TGC AAC GTC ACC CTG GGG GGC GAA        966
Gln Glu Gly Ala Arg Gln Leu Val Cys Asn Val Thr Leu Gly Gly Glu
        295                     300                     305

AAC CGG GAG ACC CGG GAG AAC GTG ACC ATC TAC AGC TTC CCG GCA CCA       1014
Asn Arg Glu Thr Arg Glu Asn Val Thr Ile Tyr Ser Phe Pro Ala Pro
310                     315                     320                 325

CTC CTG ACC CTG AGC GAA CCC AGC GTC TCC GAG GGG CAG ATG GTG ACA       1062
Leu Leu Thr Leu Ser Glu Pro Ser Val Ser Glu Gly Gln Met Val Thr
                330                     335                     340

GTA ACC TGC GCA GCT GGG GCC CAA GCT CTG GTC ACA CTG GAG GGA GTT       1110
Val Thr Cys Ala Ala Gly Ala Gln Ala Leu Val Thr Leu Glu Gly Val
            345                     350                     355

CCA GCC GCG GTC CCG GGG CAG CCC GCC CAG CTT CAG CTA AAT GCC ACC       1158
Pro Ala Ala Val Pro Gly Gln Pro Ala Gln Leu Gln Leu Asn Ala Thr
                360                     365                     370

GAG AAC GAC GAC AGA CGC AGC TTC TTC TGC GAC GCC ACC CTC GAT GTG       1206
Glu Asn Asp Asp Arg Arg Ser Phe Phe Cys Asp Ala Thr Leu Asp Val
        375                     380                     385

GAC GGG GAG ACC CTG ATC AAG AAC AGG AGC GCA GAG CTT CGT GTC CTA       1254
Asp Gly Glu Thr Leu Ile Lys Asn Arg Ser Ala Glu Leu Arg Val Leu
390                     395                     400                 405

TAC GCT CCC CGG CTA GAC GAT TCG GAC TGC CCC AGG AGT TGG ACG TGG       1302
Tyr Ala Pro Arg Leu Asp Asp Ser Asp Cys Pro Arg Ser Trp Thr Trp
                410                     415                     420

CCC GAG GGC CCA GAG CAG ACG CTG CGC TGC GAG GCC CGC GGG AAC CCA       1350
Pro Glu Gly Pro Glu Gln Thr Leu Arg Cys Glu Ala Arg Gly Asn Pro
            425                     430                     435

GAA CCC TCA GTG CAC TGT GCG CGC TCC GAC GGC GGG GCC GTG CTG GCT       1398
Glu Pro Ser Val His Cys Ala Arg Ser Asp Gly Gly Ala Val Leu Ala
        440                     445                     450

CTG GGC CTG CTG GGT CCA GTC ACT CGG GCG CTC TCA GGC ACT TAC CGC       1446
Leu Gly Leu Leu Gly Pro Val Thr Arg Ala Leu Ser Gly Thr Tyr Arg
455                     460                     465

TGC AAG GCG GCC AAT GAT CAA GGC GAG GCG GTC AAG GAC GTA ACG CTA       1494
Cys Lys Ala Ala Asn Asp Gln Gly Glu Ala Val Lys Asp Val Thr Leu
470                     475                     480                 485

ACG GTG GAG TAC GCA CCA GCG CTG GAC AGC GTG GGC TGC CCA GAA CGC       1542
Thr Val Glu Tyr Ala Pro Ala Leu Asp Ser Val Gly Cys Pro Glu Arg
                490                     495                     500

ATT ACT TGG CTG GAG GGA ACA GAA GCC TCG CTG AGC TGT GTG GCG CAC       1590
Ile Thr Trp Leu Glu Gly Thr Glu Ala Ser Leu Ser Cys Val Ala His
            505                     510                     515

GGG GTA CCG CCG CCT GAT GTG ATC TGC GTG CGC TCT GGA GAA CTC GGG       1638
Gly Val Pro Pro Pro Asp Val Ile Cys Val Arg Ser Gly Glu Leu Gly
```

|     |     |     |     |     |     |     |     |     |     |     |     |     |     |     |     |     |
|---|---|---|---|---|---|---|---|---|---|---|---|---|---|---|---|---|
|     |     |     | 520 |     |     |     |     |     | 525 |     |     |     |     |     | 530 |     |

| GCC | GTC | ATC | GAG | GGG | CTG | TTG | CGT | GTG | GCC | CGG | GAG | CAT | GCG | GGC | ACT | 1686 |
|---|---|---|---|---|---|---|---|---|---|---|---|---|---|---|---|---|
| Ala | Val | Ile | Glu | Gly | Leu | Leu | Arg | Val | Ala | Arg | Glu | His | Ala | Gly | Thr |  |
|  |  | 535 |  |  |  | 540 |  |  |  |  | 545 |  |  |  |  |  |
| TAC | CGC | TGC | GAA | GCC | ACC | AAC | CCT | CGG | GGC | TCT | GCG | GCC | AAA | AAT | GTG | 1734 |
| Tyr | Arg | Cys | Glu | Ala | Thr | Asn | Pro | Arg | Gly | Ser | Ala | Ala | Lys | Asn | Val |  |
| 550 |  |  |  |  | 555 |  |  |  |  | 560 |  |  |  |  | 565 |  |
| GCC | GTC | ACG | GTG | GAA | TAT | GGC | CCC | AGG | TTT | GAG | GAG | CCG | AGC | TGC | CCC | 1782 |
| Ala | Val | Thr | Val | Glu | Tyr | Gly | Pro | Arg | Phe | Glu | Glu | Pro | Ser | Cys | Pro |  |
|  |  |  |  | 570 |  |  |  |  | 575 |  |  |  |  | 580 |  |  |
| AGC | AAT | TGG | ACA | TGG | GTG | GAA | GGA | TCT | GGG | CGC | CTG | TTT | TCC | TGT | GAG | 1830 |
| Ser | Asn | Trp | Thr | Trp | Val | Glu | Gly | Ser | Gly | Arg | Leu | Phe | Ser | Cys | Glu |  |
|  |  |  | 585 |  |  |  |  | 590 |  |  |  |  | 595 |  |  |  |
| GTC | GAT | GGG | AAG | CCA | CAG | CCA | AGC | GTG | AAG | TGC | GTG | GGC | TCC | GGG | GGC | 1878 |
| Val | Asp | Gly | Lys | Pro | Gln | Pro | Ser | Val | Lys | Cys | Val | Gly | Ser | Gly | Gly |  |
|  |  | 600 |  |  |  | 605 |  |  |  |  | 610 |  |  |  |  |  |
| ACC | ACT | GAG | GGG | GTG | CTG | CTG | CCG | CTG | GCA | CCC | CCA | GAC | CCT | AGT | CCC | 1926 |
| Thr | Thr | Glu | Gly | Val | Leu | Leu | Pro | Leu | Ala | Pro | Pro | Asp | Pro | Ser | Pro |  |
|  | 615 |  |  |  |  | 620 |  |  |  |  | 625 |  |  |  |  |  |
| AGA | GCT | CCC | AGA | ATC | CCT | AGA | GTC | CTG | GCA | CCC | GGT | ATC | TAC | GTC | TGC | 1974 |
| Arg | Ala | Pro | Arg | Ile | Pro | Arg | Val | Leu | Ala | Pro | Gly | Ile | Tyr | Val | Cys |  |
| 630 |  |  |  |  | 635 |  |  |  |  | 640 |  |  |  |  | 645 |  |
| AAC | GCC | ACC | AAC | CGC | CAC | GGC | TCC | GTG | GCC | AAA | ACA | GTC | GTC | GTG | AGC | 2022 |
| Asn | Ala | Thr | Asn | Arg | His | Gly | Ser | Val | Ala | Lys | Thr | Val | Val | Val | Ser |  |
|  |  |  |  | 650 |  |  |  |  | 655 |  |  |  |  | 660 |  |  |
| GCG | GAG | TCG | CCA | CCG | GAG | ATG | GAT | GAA | TCT | ACC | TGC | CCA | AGT | CAC | CAG | 2070 |
| Ala | Glu | Ser | Pro | Pro | Glu | Met | Asp | Glu | Ser | Thr | Cys | Pro | Ser | His | Gln |  |
|  |  |  | 665 |  |  |  | 670 |  |  |  |  | 675 |  |  |  |  |
| ACG | TGG | CTG | GAA | GGG | GCT | GAG | GCT | TCC | GCG | CTG | GCC | TGC | GCC | GCC | CGG | 2118 |
| Thr | Trp | Leu | Glu | Gly | Ala | Glu | Ala | Ser | Ala | Leu | Ala | Cys | Ala | Ala | Arg |  |
|  |  | 680 |  |  |  |  | 685 |  |  |  |  | 690 |  |  |  |  |
| GGT | CGC | CCT | TCC | CCA | GGA | GTG | CGC | TGC | TCT | CGG | GAA | GGC | ATC | CCA | TGG | 2166 |
| Gly | Arg | Pro | Ser | Pro | Gly | Val | Arg | Cys | Ser | Arg | Glu | Gly | Ile | Pro | Trp |  |
| 695 |  |  |  |  |  | 700 |  |  |  |  | 705 |  |  |  |  |  |
| CCT | GAG | CAG | CAG | CGC | GTG | TCC | CGA | GAG | GAC | GCG | GGC | ACT | TAC | CAC | TGT | 2214 |
| Pro | Glu | Gln | Gln | Arg | Val | Ser | Arg | Glu | Asp | Ala | Gly | Thr | Tyr | His | Cys |  |
| 710 |  |  |  |  | 715 |  |  |  |  | 720 |  |  |  |  | 725 |  |
| GTG | GCC | ACC | AAT | GCG | CAT | GGC | ACG | GAC | TCC | CGG | ACC | GTC | ACT | GTG | GGC | 2262 |
| Val | Ala | Thr | Asn | Ala | His | Gly | Thr | Asp | Ser | Arg | Thr | Val | Thr | Val | Gly |  |
|  |  |  |  | 730 |  |  |  |  | 735 |  |  |  |  | 740 |  |  |
| GTG | GAA | TAC | CGG | CCA | GTG | GTG | GCC | GAA | CTT | GCT | GCC | TCG | CCC | CCT | GGA | 2310 |
| Val | Glu | Tyr | Arg | Pro | Val | Val | Ala | Glu | Leu | Ala | Ala | Ser | Pro | Pro | Gly |  |
|  |  |  | 745 |  |  |  |  | 750 |  |  |  |  | 755 |  |  |  |
| GGC | GTG | CGC | CCA | GGA | GGA | AAC | TTC | ACG | TTG | ACC | TGC | CGC | GCG | GAG | GCC | 2358 |
| Gly | Val | Arg | Pro | Gly | Gly | Asn | Phe | Thr | Leu | Thr | Cys | Arg | Ala | Glu | Ala |  |
|  |  | 760 |  |  |  |  | 765 |  |  |  |  | 770 |  |  |  |  |
| TGG | CCT | CCA | GCC | CAG | ATC | AGC | TGG | CGC | GCG | CCC | CGG | AGG | GCC | CTC | AAC | 2406 |
| Trp | Pro | Pro | Ala | Gln | Ile | Ser | Trp | Arg | Ala | Pro | Pro | Arg | Ala | Leu | Asn |  |
| 775 |  |  |  |  | 780 |  |  |  |  | 785 |  |  |  |  |  |  |
| ATC | GGC | CTG | TCG | AGC | AAC | AAC | AGC | ACA | CTG | AGC | GTG | GCA | GGC | GCC | ATG | 2454 |
| Ile | Gly | Leu | Ser | Ser | Asn | Asn | Ser | Thr | Leu | Ser | Val | Ala | Gly | Ala | Met |  |
| 790 |  |  |  |  | 795 |  |  |  |  | 800 |  |  |  |  | 805 |  |
| GGA | AGC | CAC | GGC | GGC | GAG | TAC | GAG | TGC | GCA | CGC | ACC | AAC | GCG | CAC | GGG | 2502 |
| Gly | Ser | His | Gly | Gly | Glu | Tyr | Glu | Cys | Ala | Arg | Thr | Asn | Ala | His | Gly |  |
|  |  |  |  | 810 |  |  |  |  | 815 |  |  |  |  | 820 |  |  |
| CGC | CAC | GCG | CGG | CGC | ATC | ACG | GTG | CGC | GTG | GCC | GGT | CCG | TGG | CTA | TGG | 2550 |
| Arg | His | Ala | Arg | Arg | Ile | Thr | Val | Arg | Val | Ala | Gly | Pro | Trp | Leu | Trp |  |
|  |  |  | 825 |  |  |  |  | 830 |  |  |  |  | 835 |  |  |  |
| GTC | GCC | GTG | GGC | GGC | GCG | GCG | GGG | GGC | GCG | GCG | CTG | CTG | GCC | GCG | GGG | 2598 |
| Val | Ala | Val | Gly | Gly | Ala | Ala | Gly | Gly | Ala | Ala | Leu | Leu | Ala | Ala | Gly |  |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 840 |     |     |     |     | 845 |     |     |     |     | 850 |     |     |      |
| GCC | GGC | CTG | GCC | TTC | TAC | GTG | CAG | TCC | ACC | GCC | TGC | AAG | AAG | GGC | GAG | 2646 |
| Ala | Gly | Leu | Ala | Phe | Tyr | Val | Gln | Ser | Thr | Ala | Cys | Lys | Lys | Gly | Glu |      |
|     | 855 |     |     |     | 860 |     |     |     |     | 865 |     |     |     |     |     |      |
| TAC | AAC | GTG | CAG | GAG | GCC | GAG | AGC | TCA | GGC | GAG | GCC | GTG | TGT | CTG | AAC | 2694 |
| Tyr | Asn | Val | Gln | Glu | Ala | Glu | Ser | Ser | Gly | Glu | Ala | Val | Cys | Leu | Asn |      |
| 870 |     |     |     |     | 875 |     |     |     | 880 |     |     |     |     |     | 885 |      |
| GGA | GCG | GGC | GGC | GGC | GCT | GGC | GGG | GCG | GCA | GGC | GCG | GAG | GGC | GGA | CCC | 2742 |
| Gly | Ala | Gly | Gly | Gly | Ala | Gly | Gly | Ala | Ala | Gly | Ala | Glu | Gly | Gly | Pro |      |
|     |     |     |     | 890 |     |     |     |     | 895 |     |     |     |     | 900 |     |      |
| GAG | GCG | GCG | GGG | GGC | GCG | GCC | GAG | TCG | CCG | GCG | GAG | GGC | GAG | GTC | TTC | 2790 |
| Glu | Ala | Ala | Gly | Gly | Ala | Ala | Glu | Ser | Pro | Ala | Glu | Gly | Glu | Val | Phe |      |
|     |     |     | 905 |     |     |     |     | 910 |     |     |     |     | 915 |     |     |      |
| GCC | ATA | CAG | CTG | ACA | TCG | GCG | TGAGCCCGCT | CCCCTCTCCG | CGGGCCGGGA |     |     |     |     |     |     | 2841 |
| Ala | Ile | Gln | Leu | Thr | Ser | Ala |     |     |     |     |     |     |     |     |     |      |
|     |     | 920 |     |     |     | 925 |     |     |     |     |     |     |     |     |     |      |

```
CGCCCCCCAG ACTCACACGG GGGCTTATTT ATTGCTTTAT TTATTTACTT ATTCATTTAT    2901

TTATGTATTC AACTCCAAGG GAATTC                                         2927
```

( 2 ) INFORMATION FOR SEQ ID NO:28:

( i ) SEQUENCE CHARACTERISTICS:
        ( A ) LENGTH: 924 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

|     |     |     |     |     |     |     |     |     |     |     |     |     |     |     |
| --- | --- | --- | --- | --- | --- | --- | --- | --- | --- | --- | --- | --- | --- | --- |
| Met | Pro | Gly | Pro | Ser | Pro | Gly | Leu | Arg | Arg | Ala | Leu | Leu | Gly | Leu | Trp |
| 1 |  |  |  | 5 |  |  |  |  | 10 |  |  |  |  | 15 |  |
| Ala | Ala | Leu | Gly | Leu | Gly | Leu | Phe | Gly | Leu | Ser | Ala | Val | Ser | Gln | Glu |
|  |  |  | 20 |  |  |  |  | 25 |  |  |  |  | 30 |  |  |
| Pro | Phe | Trp | Ala | Asp | Leu | Gln | Pro | Arg | Val | Ala | Phe | Val | Glu | Arg | Gly |
|  |  | 35 |  |  |  |  | 40 |  |  |  |  | 45 |  |  |  |
| Gly | Ser | Leu | Trp | Leu | Asn | Cys | Ser | Thr | Asn | Cys | Pro | Arg | Pro | Glu | Arg |
|  | 50 |  |  |  |  | 55 |  |  |  |  | 60 |  |  |  |  |
| Gly | Gly | Leu | Glu | Thr | Ser | Leu | Arg | Arg | Asn | Gly | Thr | Gln | Arg | Gly | Leu |
| 65 |  |  |  |  | 70 |  |  |  |  | 75 |  |  |  |  | 80 |
| Arg | Trp | Leu | Ala | Arg | Gln | Leu | Val | Asp | Ile | Arg | Glu | Pro | Glu | Thr | Gln |
|  |  |  |  | 85 |  |  |  |  | 90 |  |  |  |  | 95 |  |
| Pro | Val | Cys | Phe | Phe | Arg | Cys | Ala | Arg | Thr | Leu | Gln | Ala | Arg | Gly |  |
|  |  |  | 100 |  |  |  |  | 105 |  |  |  |  | 110 |  |  |
| Leu | Ile | Arg | Thr | Phe | Gln | Arg | Pro | Asp | Arg | Val | Glu | Leu | Met | Pro | Leu |
|  |  | 115 |  |  |  |  | 120 |  |  |  |  | 125 |  |  |  |
| Pro | Pro | Trp | Gln | Pro | Val | Gly | Glu | Asn | Phe | Thr | Leu | Ser | Cys | Arg | Val |
| 130 |  |  |  |  | 135 |  |  |  |  | 140 |  |  |  |  |  |
| Pro | Gly | Ala | Gly | Pro | Arg | Ala | Ser | Leu | Thr | Leu | Thr | Leu | Leu | Arg | Gly |
| 145 |  |  |  |  | 150 |  |  |  |  | 155 |  |  |  |  | 160 |
| Ala | Gln | Glu | Leu | Ile | Arg | Arg | Ser | Phe | Ala | Gly | Glu | Pro | Pro | Arg | Ala |
|  |  |  |  | 165 |  |  |  |  | 170 |  |  |  |  | 175 |  |
| Arg | Gly | Ala | Val | Leu | Thr | Ala | Thr | Val | Leu | Ala | Arg | Arg | Glu | Asp | His |
|  |  |  |  | 180 |  |  |  |  | 185 |  |  |  |  | 190 |  |
| Gly | Ala | Asn | Phe | Ser | Cys | Arg | Ala | Glu | Leu | Asp | Leu | Arg | Pro | His | Gly |
|  |  |  | 195 |  |  |  |  | 200 |  |  |  |  | 205 |  |  |
| Leu | Gly | Leu | Phe | Glu | Asn | Ser | Ser | Ala | Pro | Arg | Glu | Leu | Arg | Thr | Phe |
|  |  | 210 |  |  |  |  | 215 |  |  |  |  | 220 |  |  |  |

| | | | | | | | | | | | | | | |
|---|---|---|---|---|---|---|---|---|---|---|---|---|---|---|
| Ser 225 | Leu | Ser | Pro | Asp 230 | Ala | Pro | Arg | Leu | Ala 235 | Ala | Pro | Arg | Leu | Leu Glu 240 |
| Val | Gly | Ser | Glu | Arg 245 | Pro | Val | Ser | Cys | Thr 250 | Leu | Asp | Gly | Leu | Phe Pro 255 |
| Ala | Ser | Glu | Ala 260 | Arg | Val | Tyr | Leu 265 | Ala | Leu | Gly | Asp | Gln 270 | Asn | Leu Ser |
| Pro | Asp | Val 275 | Thr | Leu | Glu | Gly 280 | Asp | Ala | Phe | Val | Ala 285 | Thr | Ala | Thr Ala |
| Thr | Ala 290 | Ser | Ala | Glu | Gln 295 | Glu | Gly | Ala | Arg | Gln 300 | Leu | Val | Cys | Asn Val |
| Thr 305 | Leu | Gly | Gly | Glu 310 | Asn | Arg | Glu | Thr | Arg 315 | Glu | Asn | Val | Thr | Ile Tyr 320 |
| Ser | Phe | Pro | Ala | Pro 325 | Leu | Leu | Thr | Leu | Ser 330 | Glu | Pro | Ser | Val | Ser Glu 335 |
| Gly | Gln | Met | Val 340 | Thr | Val | Thr | Cys | Ala 345 | Ala | Gly | Ala | Gln 350 | Ala | Leu Val |
| Thr | Leu | Glu 355 | Gly | Val | Pro | Ala | Ala 360 | Val | Pro | Gly | Gln 365 | Pro | Ala | Gln Leu |
| Gln | Leu 370 | Asn | Ala | Thr | Glu | Asn 375 | Asp | Asp | Arg | Arg | Ser 380 | Phe | Phe | Cys Asp |
| Ala 385 | Thr | Leu | Asp | Val | Asp 390 | Gly | Glu | Thr | Leu | Ile 395 | Lys | Asn | Arg | Ser Ala 400 |
| Glu | Leu | Arg | Val | Leu 405 | Tyr | Ala | Pro | Arg | Leu 410 | Asp | Asp | Ser | Asp | Cys Pro 415 |
| Arg | Ser | Trp | Thr 420 | Trp | Pro | Glu | Gly | Pro 425 | Glu | Gln | Thr | Leu | Arg 430 | Cys Glu |
| Ala | Arg | Gly 435 | Asn | Pro | Glu | Pro | Ser 440 | Val | His | Cys | Ala | Arg 445 | Ser | Asp Gly |
| Gly | Ala 450 | Val | Leu | Ala | Leu | Gly 455 | Leu | Leu | Gly | Pro | Val 460 | Thr | Arg | Ala Leu |
| Ser 465 | Gly | Thr | Tyr | Arg | Cys 470 | Lys | Ala | Ala | Asn | Asp 475 | Gln | Gly | Glu | Ala Val 480 |
| Lys | Asp | Val | Thr | Leu 485 | Thr | Val | Glu | Tyr | Ala 490 | Pro | Ala | Leu | Asp | Ser Val 495 |
| Gly | Cys | Pro | Glu 500 | Arg | Ile | Thr | Trp | Leu 505 | Glu | Gly | Thr | Glu | Ala 510 | Ser Leu |
| Ser | Cys | Val 515 | Ala | His | Gly | Val | Pro 520 | Pro | Pro | Asp | Val | Ile 525 | Cys | Val Arg |
| Ser | Gly 530 | Glu | Leu | Gly | Ala | Val 535 | Ile | Glu | Gly | Leu | Leu 540 | Arg | Val | Ala Arg |
| Glu 545 | His | Ala | Gly | Thr | Tyr 550 | Arg | Cys | Glu | Ala | Thr 555 | Asn | Pro | Arg | Gly Ser 560 |
| Ala | Ala | Lys | Asn | Val 565 | Ala | Val | Thr | Val | Glu 570 | Tyr | Gly | Pro | Arg | Phe Glu 575 |
| Glu | Pro | Ser | Cys 580 | Pro | Ser | Asn | Trp | Thr 585 | Trp | Val | Glu | Gly | Ser 590 | Gly Arg |
| Leu | Phe | Ser 595 | Cys | Glu | Val | Asp | Gly 600 | Lys | Pro | Gln | Pro | Ser 605 | Val | Lys Cys |
| Val | Gly 610 | Ser | Gly | Gly | Thr | Thr 615 | Glu | Gly | Val | Leu | Leu 620 | Pro | Leu | Ala Pro |
| Pro 625 | Asp | Pro | Ser | Pro | Arg 630 | Ala | Pro | Arg | Ile | Pro 635 | Arg | Val | Leu | Ala Pro 640 |
| Gly | Ile | Tyr | Val | Cys 645 | Asn | Ala | Thr | Asn | Arg 650 | His | Gly | Ser | Val | Ala Lys 655 |

```
Thr  Val  Val  Val  Ser  Ala  Glu  Ser  Pro  Pro  Glu  Met  Asp  Glu  Ser  Thr
               660                      665                     670

Cys  Pro  Ser  His  Gln  Thr  Trp  Leu  Glu  Gly  Ala  Glu  Ala  Ser  Ala  Leu
               675                      680                     685

Ala  Cys  Ala  Ala  Arg  Gly  Arg  Pro  Ser  Pro  Gly  Val  Arg  Cys  Ser  Arg
     690                      695                     700

Glu  Gly  Ile  Pro  Trp  Pro  Glu  Gln  Gln  Arg  Val  Ser  Arg  Glu  Asp  Ala
705                      710                     715                         720

Gly  Thr  Tyr  His  Cys  Val  Ala  Thr  Asn  Ala  His  Gly  Thr  Asp  Ser  Arg
               725                      730                     735

Thr  Val  Thr  Val  Gly  Val  Glu  Tyr  Arg  Pro  Val  Val  Ala  Glu  Leu  Ala
               740                      745                     750

Ala  Ser  Pro  Pro  Gly  Gly  Val  Arg  Pro  Gly  Gly  Asn  Phe  Thr  Leu  Thr
          755                      760                     765

Cys  Arg  Ala  Glu  Ala  Trp  Pro  Pro  Ala  Gln  Ile  Ser  Trp  Arg  Ala  Pro
     770                      775                     780

Pro  Arg  Ala  Leu  Asn  Ile  Gly  Leu  Ser  Ser  Asn  Asn  Ser  Thr  Leu  Ser
785                      790                     795                         800

Val  Ala  Gly  Ala  Met  Gly  Ser  His  Gly  Gly  Glu  Tyr  Glu  Cys  Ala  Arg
                    805                      810                     815

Thr  Asn  Ala  His  Gly  Arg  His  Ala  Arg  Arg  Ile  Thr  Val  Arg  Val  Ala
               820                      825                     830

Gly  Pro  Trp  Leu  Trp  Val  Ala  Val  Gly  Gly  Ala  Ala  Gly  Gly  Ala  Ala
          835                      840                     845

Leu  Leu  Ala  Ala  Gly  Ala  Gly  Leu  Ala  Phe  Tyr  Val  Gln  Ser  Thr  Ala
     850                      855                     860

Cys  Lys  Lys  Gly  Glu  Tyr  Asn  Val  Gln  Glu  Ala  Glu  Ser  Ser  Gly  Glu
865                      870                     875                         880

Ala  Val  Cys  Leu  Asn  Gly  Ala  Gly  Gly  Ala  Gly  Gly  Ala  Ala  Gly
                    885                      890                     895

Ala  Glu  Gly  Gly  Pro  Glu  Ala  Ala  Gly  Gly  Ala  Ala  Glu  Ser  Pro  Ala
               900                      905                     910

Glu  Gly  Glu  Val  Phe  Ala  Ile  Gln  Leu  Thr  Ser  Ala
               915                      920
```

( 2 ) INFORMATION FOR SEQ ID NO:29:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

```
GTACTTACAG  GATCCGCGGT  CTCGCAGGAG  CCCTTCTGGG  CGGACCTACA  GCCTGCGTGG    60

CGTTC                                                                     65
```

( 2 ) INFORMATION FOR SEQ ID NO:30:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

ATTTCTCTCG AGGATGGTCA CGTTCTCCCG G  31

( 2 ) INFORMATION FOR SEQ ID NO:31:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

ATTTCTGGAT CCTACAGCTT CCCGGCACCA CTC  33

( 2 ) INFORMATION FOR SEQ ID NO:32:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

ATTTCTCTCG AGTTCCACGC CCACAGTGAC GG  32

( 2 ) INFORMATION FOR SEQ ID NO:33:

( i ) SEQUENCE CHARACTERISTICS:
        ( A ) LENGTH: 1687 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

```
GGATCCTTTG AGCCCTGAAA GTCGAGGTTG CAGTGAGCCT TGATCGTGCC ACTGCACTCC    60
AGCCTGGGGG ACAGAGCACG ACCCTGTCTC CAAAAATAAA ATAAAAATAA AATAAATAT    120
TGGCGGGGGA ACCCTCTGGA ATCAATAAAG CTTCCTTAA CCAGCCTCTG TCCTGTGACC    180
TAAGGGTCCG CATTACTGCC CTTCTTCGGA GGAACTGGTT TGTTTTTGTT GTTGTTGTTG    240
TTTTTGCGAT CACTTTCTCC AAGTTCCTTG TCTCCCTGAG GGCACCTGAG GTTTCCTCAC    300
TCAGGGCCCA CCTGGGGTCC CGAAGCCCCA GACTCTGTGT ATCCCCAGCG GGTGTCACAG    360
AAACCTCTCC TTCTGCTGGC CTTATCGAGT GGGATCAGCG CGGCCGGGGA GAGCCACGGG    420
CAGGGGCGGG GTGGGGTTCA TGGTATGGCT TTCCTGATTG GCGCCGCCGC CACCACGCGG    480
CAGCTCTGAT TGGATGTTAA GTTCCTATC CCAGCCCCAC CTTCAGACCC TGTGCTTTCC    540
TGGAGGCCAA ACAACTGTGG AGCGAGAACT CATCTCCAAA ATAACTTACC ACGCTGGAGT    600
GAGACCACGA ATGGTGGGGA GGGGAGGGTC CCACGGACAT ATTGAGGGAC GTGGATACGC    660
AGAAGAGGTA TCCATGTGGT GGCAGCCGGG AAGGGGTGAT CAGATGGTCC ACAGGGAATA    720
TCACAAACTC GAATTCTGAC GATGTTCTGG TAGTCACCCA GCCAGATGAG CGCATGGAGT    780
TGGCGGTGGG GGGTGTCAAA GCTTGGGGCC CGGAAGCGGA GTCAAAAGCA TCACCCTCGG    840
TCCCTTGTTC TCGCGTGGAT GTCAGGGCCT CCACCCACCG AGCAGAAGGC GGACTCAGGG    900
GCGCTCCAGG GTGGCTCGAG CTCACACACG CTGAGTAGAC ACGTGCCCGC TGCACCCTGG    960
GTAAATACAG ACCCGGAGCC GAGCGGATTC TAATTTAGAC GCCCGCGAAC GCTGCGCGCA    1020
```

| | | | | | |
|---|---|---|---|---|---|
| CGCACACGTG | TCCTCGGCTC | GCTGGCACTT | TCGTCCCGCC | CCCTCCGTCG | CGTGCCGGAG | 1080 |
| CTGACCCGGA | GGGGTGCTTA | GAGGTATGGC | TCCGCGGGGT | CAAAAGGAGA | AGGATCAGTG | 1140 |
| AGAGAGGATC | CCCACACCCT | CCCCTAGAAC | TGTCCTTTCC | CCATCCAGTG | CCTCCCAAAT | 1200 |
| CTCTCTTAGT | CCCCAAATGT | ATCCCCGCCC | TAAGGGGCGC | TGGTGGGAGG | AGCTAAATGT | 1260 |
| GGGGGCGGAG | CTCGGAGTCC | AGCTTATTAT | CATGGCATCT | CAGCCAGGGC | TGGGGTAGGG | 1320 |
| GTTTGGGAAG | GGCAACCCAG | CATCCCCCGA | TCCAGAGTC | GCGGCCGGGG | ATGACGCGAG | 1380 |
| AGAGCGTGGT | CGCCCCAGA | AGGCCCTGGG | CCATCATGCC | GGCCTCCACG | TAGACCCCAG | 1440 |
| GGGTCGCTCA | CTCCTGCCAG | CTCGCCTTCA | CCAAGGCCAG | GAGCTTAGCG | CACGCTCGCC | 1500 |
| TCCCGCCCCC | CCGCCGCCTC | TGCCGCCGCC | CCCTCCTTGG | AAACCAAGTT | ACCAACGTTA | 1560 |
| AACCAATCCC | CAAGCGCAAC | TCTGTCTCCC | CCACACCCCA | CCCGCCGCGC | CGCGCGGAGC | 1620 |
| CGTCCTCTAG | CCCAGCTCCT | CGGCTCGCGC | TCTCCTCGCC | TCCTGTGCTT | TCCCCGCCGC | 1680 |
| GGCGATG | | | | | | 1687 |

( 2 ) INFORMATION FOR SEQ ID NO:34:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

CAGAACTAAG CTTACAGGAG GCGAGGAGAG CGCGAG        36

( 2 ) INFORMATION FOR SEQ ID NO:35:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

CAACAATGCT AGCCAAGCGC AACTCTGTCT C        31

( 2 ) INFORMATION FOR SEQ ID NO:36:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:36:

CAACAATGCT AGCCTTGGAA ACCAAGTTAC C        31

( 2 ) INFORMATION FOR SEQ ID NO:37:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:37:

CAACAATGCT AGCAGGAGCT TAGCGCACGC TCG          33

( 2 ) INFORMATION FOR SEQ ID NO:38:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:38:

CAACAATGCT AGCCATGCCG GCCTCCACGT AG          32

( 2 ) INFORMATION FOR SEQ ID NO:39:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:39:

CAACAATGCT AGCGTCCAGC TTATTATCAT G          31

( 2 ) INFORMATION FOR SEQ ID NO:40:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

CAACAATGCT AGCCTTAGTC CCCAAATGTA TC          32

( 2 ) INFORMATION FOR SEQ ID NO:41:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

CAACAATGCT AGCGGAGAAG GATCAGTGAG          30

( 2 ) INFORMATION FOR SEQ ID NO:42:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

CAACAATGCT AGCCTCCACC CACCGAGCAG AAG          33